US009441042B2

(12) United States Patent
Ke et al.

(10) Patent No.: US 9,441,042 B2
(45) Date of Patent: Sep. 13, 2016

(54) ANTI-KDR ANTIBODIES AND METHODS OF USE

(71) Applicants: Yaohuang Ke, San Francisco, CA (US); Sum Wai Pierre Lee, San Francisco, CA (US); Yongke Zhang, Palo Alto, CA (US); Guo-Liang Yu, Hillsborough, CA (US); Weimin Zhu, Millbrae, CA (US)

(72) Inventors: Yaohuang Ke, San Francisco, CA (US); Sum Wai Pierre Lee, San Francisco, CA (US); Yongke Zhang, Palo Alto, CA (US); Guo-Liang Yu, Hillsborough, CA (US); Weimin Zhu, Millbrae, CA (US)

(73) Assignee: Apexigen, Inc., Burlingame, CA (US)

( * ) Notice: Subject to any disclaimer, the term of this patent is extended or adjusted under 35 U.S.C. 154(b) by 21 days.

(21) Appl. No.: 14/356,120

(22) PCT Filed: Nov. 1, 2012

(86) PCT No.: PCT/US2012/062929
§ 371 (c)(1),
(2) Date: May 2, 2014

(87) PCT Pub. No.: WO2013/067098
PCT Pub. Date: May 10, 2013

(65) Prior Publication Data
US 2014/0377282 A1 Dec. 25, 2014

Related U.S. Application Data

(60) Provisional application No. 61/609,581, filed on Mar. 12, 2012, provisional application No. 61/554,758, filed on Nov. 2, 2011.

(51) Int. Cl.
*C07K 16/28* (2006.01)
*C07K 14/71* (2006.01)
*A61K 39/00* (2006.01)

(52) U.S. Cl.
CPC ........... *C07K 16/2863* (2013.01); *C07K 14/71* (2013.01); *A61K 2039/505* (2013.01); *C07K 2317/24* (2013.01); *C07K 2317/565* (2013.01); *C07K 2317/73* (2013.01); *C07K 2317/76* (2013.01); *C07K 2317/92* (2013.01); *C07K 2319/30* (2013.01)

(58) Field of Classification Search
CPC .................. C07K 16/2863; C07K 2317/565; C07K 2317/73; C07K 2317/92; C07K 2317/24; C07K 2317/76; C07K 2319/30; A61K 2039/505
USPC ........................ 424/143.1; 530/387.1, 388.22
See application file for complete search history.

(56) References Cited

U.S. PATENT DOCUMENTS 7,498,414 B2  3/2009 Zhu
8,293,483 B2 * 10/2012 Yu .......................... C07K 16/00
435/7.1

2005/0214860 A1  9/2005 Zhu
2010/0260765 A1 10/2010 Barry
2010/0317539 A1 12/2010 Yu
2011/0065112 A1  3/2011 Yu
2011/0065176 A1  3/2011 Yoo et al.

FOREIGN PATENT DOCUMENTS

EP         1438340        9/2010
EP         2785742       10/2014
WO      WO 01/74296      10/2001
WO     WO 2013/067098    5/2013

OTHER PUBLICATIONS

Winkler et al., J. Imm., 265:4505-4514, 2000.*
Rudikoff et al., Proc. Natl. Acad. Sci. USA 79: 1979-1983, Mar. 1982.*
Piatesi et al., ChemBio Chem 5: 460-466, 2004.*
Wu et al., J. Mol. Biol. 294: 151-162, 1999.*
International Search Report and Written Opinion of PCT/US2012/062929, mailing date Mar. 18, 2013, 15 Pages.
International Preliminary Report on Patentability of PCT/US2012/062929, mailed on May 6, 2014, 8 pages.
Zhu, et al., "Inhibition of vascular endothelial growth factor induced mitogenesis of human endothelial cells by a chimeric anti-kinase insert domain-containing receptor antibody," Cancer Letters, 136(2):203-213; 1999.
"Alignment KDR/VEGFR2 Human/Mouse," Uniprot, 3 pages, 2015, URL http://www.uniprot.org/align/A201510152IPF4Z9KXO.
Anonymous, et al., "Immunglobulin heavy chain variable region—Oryctolagus cuniculus (Rabbit)," Uniprot, 3 Pages, 2016, URL http://www.uniprot.org/uniprot/Q6B775.
Avery RL, et al., "Intravitreal bevacizumab (Avastin) for neovascular age-related macular degeneration." Ophthalmology 2006;113(3):363-72.
Boocock CA, et al., "Expression of vascular endothelial growth factor and its receptors flt and KDR in ovarian carcinoma." J Natl Cancer Inst. Apr. 5, 1995;87(7):506-16.
Brown, et al., "Expression of vascular permeability factor (vascular endothelial growth factor) and its receptors in breast cancer." Hum. Pathol., 6: 86-91, 1995.
Brown, et al., "Expression of vascular permeability factor (vascular endothelial growth factor) and its receptors in adenocarcinomas of the gastrointestinal tract." Cancer Res., 53: 4727-4735, 1993.
Dvorak, et al., "Distribution of vascular permeability factor (vascular endothelial growth factor) in tumors: concentration in tumor blood vessels." J. Exp. Med., 174: 1275-1278, 1991.
Dvorak, et al., "Vascular permeability factor/vascular endothelial growth factor and the significance of microvascular hyperpermeability in angiogenesis." Curr. Top. Microbiol. Immunol., 237:97-132, 1999.

(Continued)

*Primary Examiner* — Phuong Huynh
(74) *Attorney, Agent, or Firm* — Cooley LLP

(57) ABSTRACT

The present invention provides anti-KDR monoclonal antibodies and related compositions, which may be used in any of a variety of therapeutic methods for the treatment of a variety of cancers, rheumatoid arthritis, diabetic retinopathy and other diseases associated with aberrant VEGF or KDR expression and/or activity.

20 Claims, 12 Drawing Sheets

(56) References Cited

OTHER PUBLICATIONS

Ellis, et al., "Down-regulation of vascular endothelial growth factor in a human colon carcinoma cell line transfected with an antisense expression vector specific for c-src." J. Biol. Chem., 273: 1052-1057, 1998.
Extended European Search Report for EP Application No. 12846470.8, mailed on Jan. 1, 2016, 22 pages.
Ferrara, et al., "Discovery and development of bevacizumab, an anti-VEGF antibody for treating cancer." Nat Rev Drug Discov 2004;3(5):391-400.
Ferrara, et al., "Heterozygous embryonic lethality induced by targeted inactivation of the VEGF gene." Nature (Lond.), 380: 439-442, 1996.
Ferrara, et al., "The regulation of blood vessel growth by vascular endothelial growth factor." Ann. NY Acad. Sci., 752: 246-256, 1995.
Folkman, et al., "Angiogenesis." J. Bio. Chem., 267. 10931-10934, 1992.
Fong, et al., "Role of the Flt-1 receptor tyrosine kinase in regulating the assembly of vascular endothelium." Nature (Lond.), 376: 66-70, 1995.
Fong, et al., "SU5416 is a potent and selective inhibitor of the vascular endothelial growth factor anti-VEGF receptor antibody inhibits tumor growth receptor (Flk-1/KDR) that inhibits tyrosine kinase catalysis, tumor vascularization, and growth of multiple tumor types." Cancer Res., 59: 99-106, 1999.
Garcia JA, et al., "Phase II study of IMC-1121B in patients with metastatic renal cancer (mRCC) following VEGFR-2 tyrosine kinase inhibitor (TKI) therapy (IMCL CP12-0605/NCT00515697)." Am Soc Clin Oncol annual meeting 2010:326.
Hanahan, et al., "Patterns and emerging mechanisms of the angiogenic switch during tumorigenesis." Cell, 86: 353-64, 1996.
Im, et al., "Anti-angiogenesis treatment for gliomas: transfer of antisense-vascular endothelial growth factor inhibits tumor growth in vivo." Cancer Res., 59: 895-900, 1999.
Kendell, et al., "Inhibition of vascular endothelial growth factor activity by endogenously encoded soluble receptor." Proc. Natl. Acad. Sci. USA, 90: 10705-10709, 1993.
Kendrew J, et al., "An antibody targetted to VEGFR-2 Ig domains 4-7 inhibits VEGFR-2 activation and VEGFR-2 dependent angiogenesis without affecting ligand binding." Mol Cancer Ther. 10(5):770-83. 2011.
Klagsbrun, et al., "Regulators of angiogenesis." Annun. Rev. Physiol., 53: 217-239, 1991.
Klagsbrun, et al., "Vascular endothelial growth factor and its receptors." Cytokine Growth Factor Rev., 7: 259-270, 1996.
Leung, et al., "Vascular endothelial growth factor is a secreted angiogenic mitogen." Science (Washington DC), 246: 1306-1309, 1989.
Lin, et al., "Inhibition of tumor growth by targeting tumor endothelium using a soluble vascular endothelial growth factor receptor." Cell Growth Differ., 9: 49-58, 1998.
Liu B, et al., "Melanoma cell lines express VEGF receptor KDR and respond to exogenously added VEGF." Biochem Biophys Res Commun 1995 217:721-727.
Matthews, et al., "A receptor tyrosine kinase cDNA isolated from a population of enriched primitive hematopoietic cells and exhibiting close genetic linkage to c-kit." Proc. Natl. Acad. Sci. USA, 88: 9026-9030, 1991.
Millauer, et al., "Glioblastoma growth inhibited in vivo by a dominant-negative Flk-1 mutant." Nature (Lond.), 367: 576-579, 1994.
Nagy, et al., "Pathogenesis of tumor stroma generation: a critical role for leaky blood vessels and fibrin deposition." Biochim. Biophys. Acta. 948: 305-326, 1988.
Neufeld, et al., "Vascular endothelial growth factor (VEGF) and its receptors." FASEB J., 13: 9-22, 1999.
Nguyen QD, et al., "Inhibition of vascular endothelial growth factor (VEGF)-165 and semaphorin 3A-mediated cellular invasion in tumor growth by the VEGF signaling inhibitor AD 4190 in human: cancer cells and xenografts." Mol Cancer Ther. 2006 5:2070-2077.
O'Brien, et al., "Different angiogenic pathways characterize superficial and invasive bladder cancer." Cancer Res., 55: 510-513, 1995.
Peters, et al., "Vascular endothelial growth factor receptor expression during embryogenesis and tissue repair suggests a role in endothelial differentiation and blood vessel growth." Proc. Natl. Acad. Sci. USA, 90: 8915-8919, 1993.
Plate, et al., "Molecular mechanisms of developmental and tumor angiogenesis." Brain Pathol., 4: 207-218, 1994.
Plate, et al., "Vascular endothelial growth factor and glioma angiogenesis: coordinate induction of VEGF receptors, distribution of VEGF protein and possible in vivo regulatory mechanisms." Int. J. Cancer, 59: 520-529, 1994.
Plate, et al., "Vascular endothelial growth factor is a potential tumor angiogenesis factor in human gliomas in vivo." Nature (Lond.), 359: 845-848, 1992.
Posey, et al., "A Phase 1 Study of Anti-Kinase Insert Domain-containing Receptor Antibody, IMC-1C11, in Patients with Liver Metastases from Colorectal Carcinoma," Clinical Cancer Research, 9:1323-1332 (2003).
Rossler, et al., "Vascular endothelial growth factor expression in human neuroblastoma: up-regulation by hypoxia." Int. J. Cancer, 81: 113-117, 1999.
Rudikoff, et al., "Single amino acid substitution altering antigen-binding specificity," Proc. Natl. Acad. Sci. USA, 79:1979-1983 (1982).
Seetharam, L. et al. "A unique signal transduction from FLT tyrosine kinase, a receptor for vascular endothelial growth factor VEGF." Oncogene 10, 135-147 (1995).
Senger, et al., "A highly conserved vascular permeability factor secreted by a variety of human and rodent tumor cell lines." Cancer Res., 46: 5629-5632, 1986.
Shalaby, et al., "Failure of blood-island formation and vasculogenesis in Flk-1 deficient mice." Nature (Lond.), 376: 62-66, 1995.
Shweiki, et al., Vascular endothelial growth factor induced by hypoxia may mediate hypoxia-initiated angiogenesis. Nature (Lond.), 359: 843-845, 1992.
Stitt, et al., "Expression of vascular endothelial growth factor (VEGF) and its receptors is regulated in eyes with intra-ocular tumours." J. Pathol., 186: 306-312, 1998.
Takahashi, et al., "Expression of vascular endothelial growth factor and its receptor, KDR, correlates with vascularity, metastasis, and proliferation of human colon cancer." Cancer Res., 55: 3964-8968, 1995.
Terman, et al., "Identification of the KDR tyrosine kinase as a receptor for vascular endothelial cell growth factor." Biochem. Biophys. Res. Commun., 187: 1579-1586, 1992.
Van Kooten C, et al., "CD40-CD40 ligand." J Leukoc Biol 2000; 67(1):2-17.
Waltenberger, et al., "Different signal transduction properties of KDR and Flt1, two receptors for vascular endothelial growth factor." J. Biol. Chem. 269,26988-26995 (1994).
Witte L, et al., "Monoclonal antibodies targeting the VEGF receptor-2 (Flk1/KDR) as an anti-angiogenic therapeutic strategy." Cancer Metastasis Rev. Jun. 1998;17(2):155-61.
Yiqing, et al., "Effect of Anti-KDR Antibody on the Proliferation of Hemangioma Vascular Endothelial Cells in vitro," Journal of Huazhong University of Science and Techology, 27(5):551-553 (2007).
Yoshiji, et al., "Expression of vascular endothelial growth factor, its receptor, and other angiogenic factors in human breast cancer." Cancer Res., 56: 2013-2016, 1996.
Zhu Z, et al., "Inhibition of human leukemia in an animal model with human antibodies directed against vascular endothelial growth factor receptor 2. Correlation between antibody affinity and biological activity." Leukemia. Mar. 2003;17(3):604-11.
Ziebold, et al. "Differential effects of CD40 stimulation on normal and neoplastic cell growth." Arch Immunol Ther Exp (Warsz) 2000; 48: 225-33.

\* cited by examiner

FIG. 11A1

Alignment: Anti-KDR antibodies, VH

```
                 110       120       130       140
KDR-4H   KFTSPTTEDTATYFCAR--VLWPGDIAYAYHNIWGPGSLVTVSSGQ
KDR-5H   RIPSPTTEDTGTYFCAR--TENSY---FLYFTIWGPGTLVTVSSGQ
KDR-6H   KFTSPTTEDTATYFCAR--VLWPGDIAYAYHNIWGPGTLVTVSSGQ
KDR-13H  QMPSLTAADTATYFCAR--D--DSARNWFYFYLWGPGTLVTVSSGQ
KDR-14H  KFTSPTTEDTATYFCAR--VLWAGYVAYAYHNIWGPGTLVTVSSGQ
KDR-15H  QMTSLTAADTATYFCAR-------SSGYPYYFTLWGPGTLVTVSSGQ
KDR-17H  KMTSLTTEDTATYFCAR-----------PFNIWGPGTLVTVSSGQ
KDR-23H  KMTSLTAADTATYFCAR--GDDDVSDYFYYFPIWGPGTLVTVSSGQ
KDR-24H  KMTSLTAADTATYFCAR--GDDDVSDYFYYFPIWGPGTLVTVSSGQ
KDR-25H  KVTSPTTEDTATYFCAR--GTTIWS---DYLDIWGPGTLVTISSGQ
KDR-27H  KFTSPTTEDTATYFCAR--VLWPGYIAYAYHNIWGPGTLVTVSSGQ
KDR-30H  KFTSPTTEDTATYFCAR--VLWPGDIAYAYHNIWGPGTLVTVSSGQ
KDR-36H  KFTSLTTEDTATYFCAR--VLWAGSVAYAYHNIWGPGTLVTVSSGQ
KDR-40H  KITSPTTEDTATYFCAN--NYDDYGDFLHYFNIWGPGTLVTVSSGQ
KDR-42H  KFTSPTTEDTATYFCAR--ALWAGYIAYVYHNIWGPGTLVTVSSGQ
KDR-43H  KFTSPTTEDTATYFCAR--VLWPGDIAYAYHNIWGPGTLVTVSSGQ
KDR-50H  KFTSPTTEDTATYFCAR--VLWPGDIAYAYHNIWGPGTLVTVSSGQ
KDR-68H  KFTSPTTEDTATYFCAR--VLWPGDIAYAYHNIWGPGTLVTVSSGQ
KDR-69H  RFASPTTEDTATYFCAR--VLWPGSVAYAYHNIWGPGTLVTVSSGQ
KDR-71H  KFTSPTTEDTATYFCAR--VLWPGDIAYAYHNIWGPGTLVTVSAGQ
KDR-77H  KFTSPTTEDTATYFCAR--VLWAGSVAYAYHNIWGPGTLVTVSSGQ
KDR-81H  KFTSPTTEDTATYFCAR--VLWPGDIAYAYHNIWGPGTLVTVSSGQ
KDR-83H  KMTSPTTEDTATYFCAR--VLWPGEIAYAYHNIWGPGTLVTVSSGQ
KDR-91H  KMTSLTAADTATYFCAR--GDDDVSDYFYYFPIWGPGTLVTVSSGQ
KDR-92H  KMTSLTAADTATYFCAR--GDDDVSDYFYYFPIWGPGTLVTVSSGQ
KDR-93H  KMTSLTAADTATYFCAR--GDDDVSDYFYYFPIWGPGTLVTVSSGQ
KDR-95H  KFTSPTPEDTATYFCAR--VLWAGDVAYAYHNIWGPGTLVTVSSGQ
```

*FIG. 11A2*

Alignment: Anti-KDR antibodies, VL

```
             ....|....|....|....|....|....|....|....|....|....|....|....|....|....|
                      10        20        30        40        50        60        70
KDR-4L   MDTRAPTQLLGLLLLWLPGARCDLVMT--QTPSPVSAAVGGTVTINCQASEEIGG--NLAWYQQKPGQPP
KDR-5L   MDTRAPTQLLGLLLLWLPGARCAVVLT--QTPSSVSAAVGGTVTINCQASENIYS--NLAWYQQKPGQPP
KDR-6L   MDTRAPTQLLGLLLLWLPGARCDLVMT--QTPSPVSAAVGGTVTINCQASEEIGG--NLAWYQQKPGQPP
KDR-13L  MDTRAPTQLLGLLLLWLPGARCAVVLT--QTASPVSGAVGGTVTINCQASQNIYS--NLAWYQHKPGQPP
KDR-14L  MDTRAPTQLLGLLLLWLPGVICGPVMT--QTPASVSEPVGGTVTIKCQASEDIGS--NLAWYQQKPGQPP
KDR-15L  MDTRAPTQLLGLLLLWLPGARCAVVLT--QTTSSVSADVGGTVTIKCQASENIYS--LLAWYQQKPGQPP
KDR-17L  MDTRAPTQLLGLLLLWLPGAIFAQVLT--QSPSPVSAAVGGTVTINCQASQSVYNGDWLGWYQQKPGQPP
KDR-23L  MDTRAPTQLLGLLLLWLPGARCAVVLT--QTASFVSGAVGGTVTINCQASQNIYN--NLAWYRQKPGQPP
KDR-24L  MDTRAPTQLLGLLLLWLPGARCALVMT--QTASPVSAAVGGTVTISCQASQSIHS--MVSWYQQKPGQRP
KDR-25L  MDTRAPTQLLGLLLLWLPGARCDPVLT--QTPASVSAAVGGTVTINCQTSEDIAS--NLAWYQQKSGQRP
KDR-27L  MDTRAPTQLLGLLLLWLPGARCDLVMT--QTPSPVSAAVGGTVTINCQASEEIGG--NLAWYQQKPGQPP
KDR-30L  MDTRAPTQLLGLLLLWLPGVICDPVMT--QTPASVSEPVGGTVTINCQASQHIYS--NLAWYQQKPGQRP
KDR-36L  MDTRAPTQLLGLLLLWLPGARCAVVLT--QTPASVSGAVGGTVTIKCQASEDIGS--NLAWYQQKPGQPP
KDR-40L  MDTRAPTQLLGLLLLWLPGVICGPVMT--QTPASVSEPVGGTVTMKCQASEEIGG--NLAWYQQKPGQPP
KDR-42L  MDTRAPTQLLGLLLLWLPGARCDLVMT--QTPASVSEPVGGTVTINCQASEEIGG--NLAWYQQKPGQPP
KDR-43L  MDTRAPTQLLGLLLLWLPGARCDLVMT--QTPSPVSAAVGGTVTINCQASEEIGG--NLAWLQKPGQPP
KDR-50L  MDTRAPTQLLGLLLLWLPGARCDLVMT--QTPSPVSAAVGGTVTINCQASEEIGD--NLAWYQQKPGQPP
KDR-68L  MDTRAPTQLLGLLLLWLPGARCDPVLT--QTPASVSEPVGGTVTIKCQASEDLGS--NLAWYQQKPGQPP
KDR-69L  MDTRAPTQLIGLLLLWLPGARCDLVMT--QTPSPVSAPVGGTVTINCQASEEIGG--NLAWYQQKPGQPP
KDR-71L  MDTRAPTQLLGLLLLWLPGARCDLVMT--QTPSPVSAVSEPVGGTVTINCQASEEIGS--NLAWYQQKPGQPP
KDR-77L  MDTRAPTQLLGLLLLWLPGARCDVVMT--QTPSPVSAAVGGTVTINCQASEEIGG--NLAWYQQKPGQPP
KDR-81L  MDTRAPTQLLGLLLLWLPGARCDVVMT--QTPSPVSVSEPVGGTVTINCQASEEIGG--NLAWYQQKPGQPP
KDR-83L  MDTRAPTQLLGLLLLWLPGARCAVVLT--QTASPVSGAVGGTVTINCQASQNIYN--NLAWYRQKPGQPP
KDR-91L  MDTRAPTQLLGLLLLWLPGARCAVVLT--QTASPVSGAVGGTVTIKCQASQNIYN--NLAWYRQKPGQPP
KDR-92L  MDTRAPTQLLGLLLLWLPGARCAVVLT--QTASPVSGAVGGTVTIKCQASQNIYN--NLAWYQQKPGQPP
KDR-93L  MDTRAPTQLLGLLLLWLPGARCDVVMETTQTPASVSEPVGGTVTINCQASEEIAS--NLAWYQQKPGQPP
KDR-95L  MDTRAPTQLLGLLLLWLPGARCAVVLT--QTASPVSGAVGGTVTIKCQASQNIYN--NLAWYRQKPGQPP
```

*FIG. 11B1*

Alignment: Anti-KDR antibodies, VL

```
              ....|....|....|....|....|....|....|....|....|....|....|....|
                  60        70        80        90        100       110
KDR-4L   KLLIYSASTLTSGVPSRFKGSGFGTEYTLTISDLECDDAATYYCQYTYY-GFT-YVGPFGGGTEVVVK
KDR-5L   KLLIYGASALPSGVPSRFSGSRSGTQFTLTISDLECADAATYYCQSYFYSSNDDN-PFGGGTEVAVK
KDR-6L   KLLIYSASTLASGVPSRFKGSGSGTEYSLSISDLECADAATYYCQYTYY-GFS-YVGPFGGTEVVVK
KDR-13L  KLLIYKASTLASGVPSRFKGSGSGTEYILTISDLECADAATYYCQTNYY-SINGGEVTFGGGTEVVVK
KDR-14L  NLLVYSASTLTSGVPSRFKGSGSGTEYTLTISDLECADAATYYCQDTYY-GNT-YLGAFGGGTEVVVK
KDR-15L  KLLIYSASDLASGVPSRFSGSGFGTEFTLTISDLECADAATHCQSYYYSGSSADTGAFGGGTEVVVK
KDR-17L  KLLIYDASTLASGVSSLINCNGSGTQWTLTISGVQCDDAATYYCQGEFS-CSSADCVAFGGGTEVVVK
KDR-23L  KLLIYAASKLASGVPSRFSGSRSGTQFTLSISDLECADAATYYCQSYIFDSSSTDA-AFGGGTEVVVK
KDR-24L  KLLIYAASKLASGVPSRFSGSRSGTQFTLTISDLECADAATYYCQSYIFDSSSTDA-AFGGGTEVVVA
KDR-25L  KLLIYAATLASGVPSRFKGSGSGKQFTLTISDLECDDAATYYCQQDFG-GSD-VDNTFGGGTEVVVK
KDR-27L  KLLIYBASKLASGVPSRFKGSGSGTEYTLTISDLECADAATYYCQYTYY-GSS-YLGAFGGGTEVVVK
KDR-30L  QLLIYSASTLASGVPSRFKGSGFGTEYTLTISDLECADAATYYCQYTYY-GFT-YVGPFGGTEVVVK
KDR-36L  KLLIYSASTLTSGVPSRFKGSGSGTEYTLTISDLECADAATYYCQYTYF-GSS-YLGAFGGGTEVVVK
KDR-40L  KLLIYAASKLASGVPSRFAGSGSGTEYTLTISDLECADAATYYCQSYYY-GNS-YLGAFGGGTEVVVK
KDR-42L  NLLVFSASTLTSGVPSRFKGSGFGTEYTLTISDLECADAATYYCQSYYYSSDSTDN-TFGGGTEVVVK
KDR-43L  KLLIYSASTLTSGVPSRFKGSGSGTEYTLTITISDLECADAATYYCQYTYY-GFS-YVGPFGGTEVVVK
KDR-50L  QLLIYSASTLTSGVPSRFKGSGSGTEYTLTISDLECADAATYYCQYTYY-GFS-YVGPFGGTEVVVK
KDR-68L  KLLIYSASTLTSGVPSRFKGSGSGTEYTLTISDLECADAATYYCQYTYY-GFS-YVGPFGGTEVVVK
KDR-69L  KLLIYSASTLTSGVPSRFKGSGSGTEYTLTISGVQCDDAATYYCQDTYY-GNT-YLGAFGGGTEVVVR
KDR-71L  KLLIYSASTLASGVPSRFKGSGSGTEYTLTISGVQCDDAATYYCQDTYY-GNT-YLGAFGGGTEVVVK
KDR-77L  KLLIYSASTLASGVPSRFKGSGSGFGT-----ECADAATYYCQYTYY-GFS-YVGPFGGGTEVVVK
KDR-81L  KLLIYSASTLTSGVPSRFSGSGSGTQFTLSISDLECADAATYYCQSYIFDSSSTDA-AFGGGTEVVVK
KDR-83L  KLLIYAASSLASGVPSRFSGSGSGTEYTLTINDLECADAATYYCQIPYY-GFS-YVGPFGGTEVVVK
KDR-91L  KLLIYAASKLASGVPSRFSGSRSGTQFTLSISDLECADAATYYCQSYY-GFN-YVGPFGGGTEVVVK
KDR-92L  KLLIYAASKLASGVPSRFSGSGSGTEYTLTISDLECADAATYYCQSYIFDSSSTDA-AFGGGTEVVVK
KDR-93L  KLLIYAASKLASGVPSRFSGSGSGTEYTLTISDLECADAATYYCQYTYY-GFN-YVGPFGGTEVVVK
KDR-95L  KLLIYAASKLASGVPSRFSGSRSGTQFTLSISDLECADAATYYCQSYYIFDSSSTDA-AFGGGTEVVVK
```

*FIG. 11B2*

ANTI-KDR ANTIBODIES AND METHODS OF USE

CROSS REFERENCES TO RELATED APPLICATIONS

This application is a U.S. National phase application of International PCT Patent Application No. PCT/US2012/062929 filed on Nov. 1, 2012, which claims priority to U.S. Provisional Application No. 61/554,758, filed Nov. 2, 2011, and U.S. Provisional Application No. 61/609,581, filed Mar. 12, 2012, both of which are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is APEX_015_02US_ST25.txt. The text file is 103 KB, was created on Jan. 29, 2016, and is being submitted electronically via EFS-Web.

BACKGROUND

1. Technical Field

The present invention relates generally to anti-VEGF Receptor 2 (VEGFR2; aka kinase insert domain-containing receptor, or KDR) antibodies, compositions and methods of using same. Such antibodies are useful, for example, in methods for treating and inhibiting a variety of disorders including age-related macular degeneration (AMD), diabetes and ischemic retinopathies, rheumatoid arthritis, psoriasis and a variety of oncological diseases including renal cell carcinoma, metastatic gastric or gastro-esophageal junction adenocarcinoma, breast cancer, hepatocellular carcinoma, colorectal cancer, prostate cancer, non-small cell lung cancer, ovarian cancers, melanoma, and recurrent glioblastoma multiforme, leukemias and solid tumors.

2. Description of the Related Art

VEGFR2/KDR is the primary angiogenic receptor and binds VEGF isoforms A, C, D and E, and is important for endothelial cell differentiation, as well as the mitogenic, angiogenic and permeability-enhancing effects of VEGF. An anti-KDR antibody may prevent all known VEGF isoforms from binding to VEGFR2/KDR and initiating signaling. In addition, because tumors secrete many more molecules of VEGF while the number of receptors remains relatively constant, targeting the receptor increases the probability of completely suppressing signaling even in the presence of very high levels of VEGF isoforms.

Angiogenesis

Angiogenesis, the formation of new blood vessels from existing vasculature, is a tightly regulated event and plays an important role in normal physiology such as embryonic development, follicular growth, wound healing, as well as in pathological conditions such as tumor growth and progression (1, 2).

Growth and metastasis of primary tumors is dependent on formation of new blood vessels. In the absence of neovascularization, tumors become necrotic or apoptotic and/or fail to grow beyond 2-3 mm$^3$ in size (3). Tumor angiogenesis involves several processes, including endothelial cell activation, proliferation, migration, and tissue infiltration from preexisting blood vessels that are triggered by specific angiogenic growth factors produced by tumor cells and the surrounding stroma (1-4).

VEGF and VEGF Receptors

Several growth factors have been identified as possible regulators of angiogenesis (5). Among these factors, vascular endothelial growth factor (VEGF) and its receptors have been shown to play a key role in tumor angiogenesis (6-9).

VEGF is a homodimeric 34-42 kDa heparin-binding glycoprotein with potent angiogenic, mitogenic, and vascular permeability-enhancing activities (10, 11). VEGF regulates vasculogenesis during embryonic development and angiogenic processes during adult life (12, 13). VEGF family members include VEGF-A, VEGF-B, VEGF-C, VEGF-D, and VEGF-E. VEGFs bind to and mediate activity through the VEGF receptors (VEGFRs). There are 3 VEGFRs including VEGFR1 (Flt-1), VEGFR2 (Flk-1/KDR) and VEGFR3 (14-16).

The physiological importance of VEGF and the VEGF receptors in blood vessel formation has been clearly demonstrated in gene knockout experiments (17-18). The VEGFR1 tyrosine kinase exhibits all the conserved motifs that are required for kinase activity. However, the level of phosphorylation of VEGFR1 in response to VEGF-A is low (37, 38). The function of VEGFR-1 is less well defined, it may act as a dummy/decoy receptor to sequester VEGF from VEGFR-2 binding and modulate VEGFR-2 signaling. It has been shown that VEGFR-3 may mediate lymphangiogenesis in response to VEGF-C and VEGF-D. VEGFR2/KDR is the primary angiogenic receptor and binds VEGF isoforms A, C, D and E, and is important for endothelial cell differentiation and mitogenesis.

Structure and Biology of KDR

The VEGFRs are receptor tyrosine kinases and belong to the same family of receptors as the PDGFs and fibroblast growth factors (FGFs). VEGFR2/KDR is a 200 kDa glycoprotein that consists of 7 Ig-like loops in the extracellular domain, a transmembrane domain, and two intracellular tyrosine kinase domains split by a kinase insert. The second and third Ig-like loops are high-affinity ligand-binding domains for VEGF while the first and fourth Ig-like loops regulate ligand binding and receptor dimerization, respectively. VEGF binds KDR with a Kd of 75-250 pM as compared to a Kd of 25 pM for VEGFR1.

KDR is primarily expressed on the cell surface of vascular endothelial cells. KDR is also found on the cell surface of hematopoietic cells, vascular smooth muscle cells (VSMCs), and some malignant cells.

KDR is the primary receptor in developmental angiogenesis and hematopoiesis and is the major mediator of the mitogenic, angiogenic and permeability-enhancing effects of VEGF. VEGFR2$^{-/-}$ knockout mice showed embryonic lethality at E8.5-9.5 with defective blood-island formation and vasculogenesis (41). Physiologically, the binding of VEGF to KDR results in endothelial cell activation, proliferation, migration, invasion and survival. Upon binding to VEGF, KDR receptors dimerize, leading to activation of kinase domains and transduction of KDR receptor signaling. Like many other receptor tyrosine kinases, the major intracellular signaling pathways that lead to angiogenesis include MAPK and PI3 kinase activation.

KDR as Molecular Target for Antibody Therapy

VEGFR2/VEGF axis is a predominant pathway in tumor angiogenesis. Numerous studies have shown that overexpression of VEGF and KDR are strongly associated with invasion and metastasis in human malignancies (6). VEGF receptors have been implicated in angiogenesis that occurs in many human solid tumors, including bladder (21), breast (22, 23), colon (24, 25), gastrointestinal (26), glioma (12, 27), renal (28), melanoma (29), and neuroblastoma (30).

The important role for KDR in tumor angiogenesis was directly demonstrated in studies in which expression of a dominant-negative KDR receptor resulted in decreased endothelial cell mitogenesis and growth inhibition of subcutaneous glioma tumors in athymic mice (31). Other studies confirmed this role using neutralizing soluble VEGF receptor (34, 35) as well as using KDR inhibitors including small molecule tyrosine kinase inhibitor (TKI) and KDR-specific Abs.

In addition to its effect on tumor angiogenesis, KDR is also found on some tumor cells such as leukemia cells and may directly mediate tumorigenesis through an autocrine loop that stimulates leukemia growth (42, 43).

Inhibition of KDR signaling can reduce angiogenesis and retards tumor growth (35, 36). The vast majority of current treatments targeting KDR are small-molecule tyrosine tered around VEGF-producing tumor cells (12). VEGF expression is strongly up-regulated under hypoxic conditions, such as those associated with rapidly growing tumors (20). Neutralizing VEGF by an antibody such as Avastin (33, 34) is a clinically approved therapy to inhibit cancer or other angiogenesis diseases such AMD. However, resistance to VEGF blockade has been found even when given in combination with chemotherapy. This resistance may be associated with remodeled vasculature and with increased expression of other angiogenic factors.

In contrast to Avastin® which binds one of the ligands (VEGF-A) only, an anti-KDR antibody is expected to prevent all known VEGFs from binding to VEGFR2/KDR. This may have a more profound inhibitory effect on tumor angiogenesis than just blocking VEGF-A. It is possible that therapy with an anti-KDR antibody may be effective in cases of Avastin® resistance. The potential advantage of targeting KDR over VEGF is summarized in Table 1.

TABLE 1

Advantages of antibody therapy targeting KDR over VEGF

| Advantages over anti-VEGF antibodies | Mechanism/Reasons |
| --- | --- |
| Fewer antibodies are needed to achieve effective inhibition of VEGF-KDR pathway | 1) Overexpression/abundant production of VEGF in tumors<br>2) KDR expression on endothelial cells is more constant than VEGF from tumor and cancer-related stroma |
| Specifically blocks KDR pathway from activation by several VEGF ligands | An anti-KDR antibody selectively blocks KDR signalling from activation by related ligands (VEGF-A, E, C, D) |
| Provides an option for combination therapy with anti-VEGF for more efficient inhibition | Combination therapy may overcome the acquired resistance by anti-VEGF therapy | kinase inhibitors (TKIs). TKIs interfere with the binding of ATP or other substrates to the tyrosine kinases and disrupt the kinase catalytic activity. All of the TKIs developed to date (like Sunitinib) bind reversibly to the ATP binding site of the KDR kinase domain.

VEGF is expressed at high levels in various types of tumors (12, 19), and newly sprouting capillaries are clustered around VEGF-producing tumor cells (12). VEGF expression is strongly up-regulated under hypoxic conditions, such as those associated with rapidly growing tumors (20). Neutralizing VEGF by an antibody such as Avastin® (33, 34) is a clinically approved therapy to inhibit cancer or other angiogenesis diseases such AMD. However, resistance to VEGF blockade has been found even when given in combination with chemotherapy. This resistance may be associated with remodeled vasculature and with increased expression of other angiogenic factors. As such, there remains a need in the art for improved compositions and methods for inhibiting cancer and other diseases associated with angiogenesis.

Although both TKI and anti-KDR antibodies can inhibit KDR-mediated angiogenesis, the antibody approach has advantages over TKIs. In contrast to TKIs, an anti-KDR antibody is a more specific KDR targeting agent (i.e., it does not inhibit other VEGF receptors). Because of its high specificity, an anti-KDR antibody may be able to limit and/or avoid the off-target effects and toxicities caused by the less specific TKIs (44).

VEGF is expressed at high levels in various types of tumors (12, 19), and newly sprouting capillaries are clus- Therefore, an antibody that targets KDR and blocks KDR signaling may have higher specificity and more complete target inhibition and therefore may have broad applications in both solid and liquid tumors as well as have the potential to overcome Avastin® resistance.

Anti-KDR Therapeutic Antibodies in Development

Ramucirumab (IMC-1121B)

Ramucirumab, which is being developed by ImClone Systems/Eli Lilly, is a fully human IgG1 mAb that binds human KDR (KD X50 pM) and blocks VEGF binding, thus inhibiting angiogenesis. Because Ramucirumab does not cross react with mouse KDR, a surrogate anti-mouse KDR antibody (DC-101) was generated and used for POC preclinical studies.

In phase I clinical trials in patients with advanced cancers, ramucirumab was well tolerated on weekly dosing schedules. Mechanism-related dose limiting toxicities were hypertension and deep vein thrombosis. Data from a phase II trial as a monotherapy in patients with metastatic renal cell carcinoma following KDR tyrosine kinase inhibitor therapy was reported recently (39). Patients with progressive disease or intolerance to either sorafenib, sunitinib or both were administered 8 mg/kg ramucirumab IV biweekly. Tumor assessments were performed every six weeks. A total of 40 patients were enrolled and 39 were treated. Nineteen patients (49%) had stable disease that lasted for more than 5 months; preliminary median progression free survival was 6 months. More phase II trials are ongoing in combination with dacarbazine in melanoma, with mitoxantrone/prednisone in patients with prostate cancer, with carboplatin/paclitaxel in patients with NSCLC and with oxaliplatin/folinic acid/5-fluorouracil in patients with colorectal cancer.

Ramucirumab is currently being evaluated in patients with breast cancer, gastric cancer or gastroesophageal junction adenocarcinoma and hepatocellular carcinoma in 3 Phase III studies. Three additional Phase 3 studies of ramucirumab with or without paclitaxel in metastatic gastric adenocarcinoma, in second line metastatic colorectal cancer and in second line non-small cell lung cancer are ongoing.

33C3

33C3 developed by AstraZeneca is a fully human anti-KDR antibody generated using XenoMouse™ technology. 33C3 binds the Ig domains 4-7 of KDR, and so has no impact on VEGF-A binding to KDR. It does not compete with antibody that interacts at the ligand binding site. 33C3 has high affinity for KDR (KD<1 nM) and inhibits VEGF-A induced phosphorylation of KDR. In vitro, 33C3 potently inhibits both tube length and number of branch points in a 2D angiogenesis assay and endothelial tube formation in a 3D assay. In vivo, 33C3 is a very effective inhibitor of angiogenesis in both a human endothelial angiogenesis assay and in a human skin chimera model (40). 33C3 is now at the early preclinical stage of development. 33C3 has not been tested in in vivo tumor models, due to lack of cross reactivity to mouse KDR.

TTAC-0001

TTAC-0001, a fully human anti-KDR antibody generated by phage display, is now in the preclinical stage of developed by PharmAbcine. The antibody showed potent anti-angiogenic efficacy against various cancer mouse models (45).

BRIEF SUMMARY

One aspect of the present disclosure provides an isolated antibody, or an antigen-binding fragment thereof, that binds to KDR, comprising (i) a heavy chain variable region comprising the VHCDR1 region set forth in SEQ ID NO:3 or 11, the VHCDR2 region set forth in SEQ ID NO:4 or 12, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO: 8; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment, an isolated antibody, or antigen-binding fragment thereof as disclosed herein comprises the heavy chain variable region comprising the amino acid sequence set forth in SEQ ID NO:1. In another embodiment, an isolated antibody, or antigen-binding fragment thereof as disclosed herein comprises the light chain variable region comprising the amino the amino acid sequence set forth in SEQ ID NO:2. In one embodiment, the anti-KDR antibodies disclosed herein bind to human KDR and crossreact with mouse or monkey KDR.

Another aspect of the present disclosure provides an isolated antibody, or an antigen-binding fragment thereof, that binds to KDR, comprising (i) a heavy chain variable region comprising a VHCDR1, a VHCDR2, and a VHCDR3 of an antibody as set forth in FIG. 11; and (ii) a corresponding light chain variable region comprising a VLCDR1, a VLCDR2 and a VLCDR3 of an antibody as set forth in FIG. 11; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment, the isolated antibody, or antigen-binding fragment thereof, comprises a heavy chain variable region comprising any one of the amino acid sequences set forth in SEQ ID NOs:17-42. In another embodiment, the isolated antibody, or antigen-binding fragment thereof, comprises a light chain variable region comprising any one of the amino acid sequences set forth in SEQ ID NO:43-68.

Another aspect of the present disclosure provides an isolated antibody, or an antigen-binding fragment thereof, that binds to KDR, comprising a heavy chain variable region comprising the amino acid sequence set forth in SEQ ID NO:1. In one embodiment, the isolated antibody comprises a heavy chain variable region comprising the amino acid sequence set forth in SEQ ID NO:1 and comprises a light chain variable region which comprises an amino acid sequence having at least 90% identity to the amino acid sequence set forth in SEQ ID NO:2. In one embodiment, such an antibody comprises a light chain variable region which comprises the amino acid sequence set forth in SEQ ID NO:2.

Yet another aspect of the present disclosure provides an isolated antibody, or an antigen-binding fragment thereof, that binds to KDR, comprising a light chain variable region comprising the amino acid sequence set forth in SEQ ID NO:2. In one embodiment, the isolated antibody, or an antigen-binding fragment thereof, that binds to KDR, comprises a light chain variable region comprising the amino acid sequence set forth in SEQ ID NO:2 and comprises a heavy chain variable region which comprises an amino acid sequence having at least 90% identity to the amino acid sequence set forth in SEQ ID NO:1.

In certain embodiments of the present disclosure, the anti-KDR antibodies described herein are humanized. Illustrative VH and VL regions of the humanized antibodies that bind KDR as described herein are set forth in SEQ ID NOs:9 and 10.

In another embodiment of the anti-KDR antibodies described herein, the antibody may comprise a single chain antibody, a ScFv, a univalent antibody lacking a hinge region, a minibody, a Fab, a Fab' fragment, a F(ab')$_2$ fragment or a whole antibody.

In certain embodiments, the isolated antibodies described herein comprise a human IgG constant domain. In this regard, the IgG constant domain may comprise an IgG1 CH1 domain, such as the IgG1 CH1 domain amino acid sequence as set forth in SEQ ID NO:16. In certain embodiments, the antibodies described herein comprise an IgG constant domain which comprises an IgG1 Fc region.

Another aspect of the present disclosure provides an isolated antibody, or an antigen-binding fragment thereof, that competes with an anti-KDR antibody as described herein for binding to human KDR.

Yet another aspect of the present disclosure provides an isolated antibody, or antigen-binding fragment thereof, that binds KDR with a high affinity, such as an affinity of a KD of $5.3 \times 10^{-11}$ M or lower. In this regard, the affinity of an anti-KDR antibody as disclosed herein may be about 3.5, 4, 4.5, 5, or $5.5 \times 10^{-11}$ M. In certain embodiments, the isolated antibodies of the present disclosure crossreact with murine KDR or non-human primate KDR.

Another aspect of the present disclosure provides an isolated antibody, or antigen-binding fragment thereof wherein the isolated antibody or antigen-binding fragment thereof blocks VEGF binding to KDR; inhibits KDR signaling; inhibits endothelial cell proliferation; inhibits tumor angiogenesis; inhibits tumor cell growth; or a combination of any one or more of the afforementioned fuctions. In one embodiment, the isolated antibody or antigen-binding fragment thereof, blocks VEGF binding to KDR, inhibits KDR signaling, inhibits endothelial cell proliferation, inhibits tumor angiogenesis, and inhibits tumor cell growth.

In one aspect of the invention, an isolated antibody or antigen-binding fragment thereof directly inhibits tumor growth.

The present disclosure also provides isolated polynucleotides encoding the anti-KDR antibodies as described herein and expression vectors comprising such isolated polynucleotides and isolated host cells comprising such vectors.

Another aspect of the present disclosure provides a composition comprising a physiologically acceptable carrier and a therapeutically effective amount of the isolated antibody or antigen-binding fragment thereof as described herein.

Yet another aspect of the present disclosure provides a method for treating a patient having a cancer associated with aberrant VEGF or KDR expression or activity, comprising administering to the patient a composition comprising a physiologically acceptable carrier and a therapeutically effective amount of an isolated antibody or antigen-binding fragment thereof as described herein, thereby treating the cancer associated with aberrant VEGF or KDR expression or activity. In this regard, the antibodies described herein may be useful for the treatment of cancers including, but not limited to, angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancer, melanoma, recurrent glioblastoma multiforme, and leukemia.

Another aspect of the present invention provides a method for treating a patient afflicted by an inflammatory disease, comprising administering to the patient a therapeutically effective amount of a composition comprising any one or more of the antibodies disclosed herein, thereby treating the patient afflicted with the inflammatory disease.

Another aspect of the present disclosure provides a method for treating a patient having rheumatoid arthritis comprising administering to the patient a composition comprising a physiologically acceptable carrier and a therapeutically effective amount of an isolated antibody or antigen-binding fragment thereof as described herein, thereby treating the patient having rheumatoid arthritis.

Another aspect of the present disclosure provides a method for treating a patient having psoriasis comprising administering to the patient a composition comprising a physiologically acceptable carrier and a therapeutically effective amount of an isolated antibody or antigen-binding fragment thereof as described herein, thereby treating the patient having psoriasis.

A further aspect of the present disclosure provides a method for treating a patient afflicted by an angiogenesis mediated disease, comprising administering to the patient a therapeutically effective amount of a composition comprising any one or more of the antibodies disclosed herein, thereby treating the patient afflicted with the angiogenesis mediated disease. In this regard in certain embodiments the patient is afflicted by age related macular degeneration.

BRIEF DESCRIPTION OF THE DRAWINGS

FIG. 11 is an alignment of the VH and VL regions of the anti-KDR antibodies identified in Example 1. FIG. 11A1 shows amino acids 1-100 of the VH region. FIG. 11A2 shows the remaining amino acids of the VH. FIG. 11B1 shows the alignment of amino acids 1-70 of the VL region. FIG. 11B2 shows the alignment of the remaining amino acids of the VL region. SEQ ID Nos for the VH regions shown in the alignment are provided in SEQ ID Nos:1 and 17-42; the SEQ ID Nos for the VL regions shown in the alignment are provided in SEQ ID Nos:2 and 43-68, as summarized in the "Brief Description of the Sequences" section below and in Table 3. The CDRs are underlined.

BRIEF DESCRIPTION OF THE SEQUENCES

Figure 1:
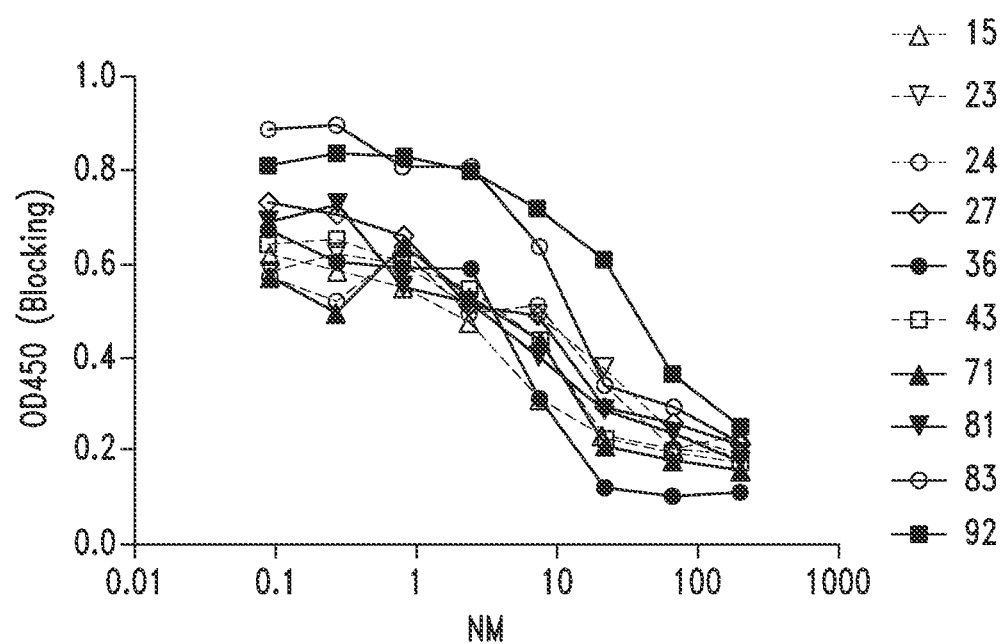
FIG. 1: shows a graph of the screening results for most potent antibodies that block KDR binding to VEGF.

SEQ ID NO:1 is the amino acid sequence of the VH region of the clone 36 rabbit anti-KDR antibody.

SEQ ID NO:2 is the amino acid sequence of the VL region of the clone 36 rabbit anti-KDR antibody.

SEQ ID NO:3 is the amino acid sequence of the VHCDR1 region of the clone 36 rabbit anti-KDR antibody.

SEQ ID NO:4 is the amino acid sequence of the VHCDR2 region of the clone 36 rabbit anti-KDR antibody.

SEQ ID NO:5 is the amino acid sequence of the VHCDR3 region of the clone 36 rabbit anti-KDR antibody.

SEQ ID NO:6 is the amino acid sequence of the VLCDR1 region of the clone 36 rabbit anti-KDR antibody.

SEQ ID NO:7 is the amino acid sequence of the VLCDR2 region of the clone 36 rabbit anti-KDR antibody.

SEQ ID NO:8 is the amino acid sequence of the VLCDR3 region of the clone 36 rabbit anti-KDR antibody.

SEQ ID NO:9 is the amino acid sequence of the humanized sequence of the VH region of the clone 36 rabbit anti-KDR antibody.

SEQ ID NO:10 is the amino acid sequence of the humanized sequence of the VL region of the clone 36 rabbit anti-KDR antibody.

SEQ ID NO:11 is the amino acid sequence of the VHCDR1 region of the humanized clone 36 anti-KDR antibody (APX004).

SEQ ID NO:12 is the amino acid sequence of the VHCDR2 region of the humanized clone 36 anti-KDR antibody (APX004).

SEQ ID NO:13 is the polynucleotide sequence encoding the human CK region.

SEQ ID NO:14 is the amino acid sequence of human CK.

SEQ ID NO:15 is the polynucleotide sequence encoding the human IgG1 CH1 region.

SEQ ID NO:16 is the amino acid sequence of the human IgG1 CH1 region.

SEQ ID NOs:17-42 are the amino acid sequences of the VH of rabbit anti-KDR antibody clones as summarized in Table 3.

SEQ ID NOs:43-68 are the amino acid sequences of the VL of rabbit anti-KDR antibody clones as summarized in Table 3.

SEQ ID Nos:69-95 are the amino acid sequences of the VHCDR1 for the rabbit anti-KDR antibody clones as shown in FIG. 11.

SEQ ID Nos:96-122 are the amino acid sequences of the VHCDR2 for the rabbit anti-KDR antibody clones as shown in FIG. 11.

SEQ ID Nos:123-149 are the amino acid sequences of the VHCDR3 for the rabbit anti-KDR antibody clones as shown in FIG. 11.

SEQ ID Nos:150-176 are the amino acid sequences of the VLCDR1 for the rabbit anti-KDR antibody clones as shown in FIG. 11.

SEQ ID Nos:177-203 are the amino acid sequences of the VLCDR2 for the rabbit anti-KDR antibody clones as shown in FIG. 11.

SEQ ID Nos:204-230 are the amino acid sequences of the VLCDR3 for the rabbit anti-KDR antibody clones as shown in FIG. 11.

DETAILED DESCRIPTION

The anti-KDR antibodies described herein have high binding affinity (53 pM) and selectivity to KDR. The antibodies described herein block the interaction of KDR with VEGF and inhibit VEGF-induced KDR phosphorylation and endothelial cell proliferation. In certain embodiments, the antibodies described herein cross-react with mouse KDR, thus enabling the antibodies to be tested in in vivo animal models without a need for a surrogate antibody. The antibodies described herein demonstrate potent activity at inhibiting tumor growth in human tumor xenograft models. Because of cross-reactivity, the anti-KDR antibodies described herein can be fully evaluated and characterized in vivo in terms of PK, PD, biomarker development even potential toxicities in preclinical mouse models before testing it in non-human primates and humans.

The present disclosure relates to antibodies and antigen-binding fragments thereof the specifically bind to KDR, in particular antibodies having specific epitopic specificity and functional properties. One embodiment of the invention encompasses specific humanized antibodies and fragments thereof capable of binding to KDR, blocking KDR binding with VEGF and inhibiting VEGF induced downstream cell signaling and biological effects. In more specific embodiments of the invention, the antibodies described herein specifically bind to KDR with affinity of about $5.3 \times 10^{-11}$ M and block KDR binding to VEGF.

In further embodiments, the antibodies described herein directly inhibit tumor growth. In this regard, certain tumors express KDR and may use the VEGF-KDR pathway as an autocrine loop to grow. Thus, in certain embodiments, the anti-tumor effect mediated by the antibodies described herein may include (i) anti-angiogenesis and/or (ii) direct inhibition of tumor growth.

Embodiments of the invention pertain to the use of anti-KDR antibodies or antigen-binding fragments thereof for the diagnosis, assessment and treatment of diseases and disorders associated with VEGF or aberrant expression thereof. The subject antibodies are used in the treatment or prevention of disorders associated with VEGF or KDR expression and/or activity, including but not limited to, rheumatoid arthritis, diabetes and ischemic retinopathies, age-related macular degeneration, psoriasis and glomerular hypertrophy associate with proteinuria and a variety of oncological diseases including angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors, among other diseases.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to the KDR. In particular, the antibodies described herein specifically bind to KDR with unexpectedly high affinity, block VEGF binding to the KDR, block VEGF activity and have therapeutic utility for the treatment of diseases associated with aberrant expression or activity of VEGF. The antibodies described herein also have advantageous properties such as the ability to inhibit a variety of VEGF/KDR-mediated biological effects (e.g., phosphorylation of KDR, angiogenesis, endothelial cell proliferation, and other VEGF/KDR-mediated effects known to the skilled person). The antibodies described herein may also have effects on KDR receptor internalisation.

Sequences of illustrative antibodies, or antigen-binding fragments, or complementarity determining regions (CDRs) thereof, are set forth in SEQ ID NOs:1-12 and 17-230.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to the KDR. In this regard, an antigen-binding fragment of the herein described antibodies may comprise 1, 2, 3, 4, 5, or all 6 CDRs of a VH and VL sequence set forth herein from antibodies that bind KDR. An antigen-binding fragment of the KDR-specific antibodies described herein is capable of binding to KDR. In certain embodiments, an antigen-binding fragment or an antibody comprising an antigen-binding fragment, prevents or inhibits VEGF binding to the KDR and subsequent signalling events. In certain embodiments, the antigen-binding fragment binds specifically to and/or inhibits or modulates the biological activity of human KDR.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $0^{-7}$ or $10^{-8}$ M. In some embodiments, the equilibrium dissociation constant may be $0^{-9}$ M or $10^{-1o}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (Ill et al., *Prot. Eng.* 10: 949-57 (1997); minibodies (Martin et al., *EMBO J* 13: 5305-9 (1994); diabodies (Holliger et al., *PNAS* 90: 6444-8 (1993); or Janusins (Traunecker et al., *EMBO J* 10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to KDR through one binding domain and to a second molecule through a second binding domain. These antibodies may be produced through recombinant molecular biological techniques or may be physically conjugated together.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, a KDR binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a VH domain (Ward, E. S. et al., Nature 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.,* 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts, e.g., E. coli (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of nanobodies have been produced. Nanobodies may be formulated as a ready-to-use solution having a long shelf life. The Nanoclone method (see, e.g., WO 06/079372) is a proprietary method for generating Nanobodies against a desired target, based on automated high-throughput selection of B-cells.

In certain embodiments, the anti-KDR antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., PNAS (1988) 86:10029-10033; Riechmann et al., *Nature* (1988) 332:323-327). Illustrative methods for humanization of the anti-KDR antibodies disclosed herein include the methods described in U.S. Pat. No. 7,462,697. Illustrative humanized antibodies according to certain embodiments of the present invention comprise the humanized sequences provided in SEQ ID NOs:9, 10, 19 and 20.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-KDR antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-KDR antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, a KDR-binding antibody comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds KDR. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for KDR. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to KDR. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for KDR antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for KDR and optionally with one or more desired properties. The VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a KDR epitope is an antibody that binds one KDR epitope with greater affinity, avidity, more readily, and/or with greater duration than it binds to other KDR epitopes or non-KDR epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

In certain embodiments, the anti-KDR antibodies described herein have an affinity of about 100, 150, 155, 160, 170, 175, 180, 185, 190, 191, 192, 193, 194, 195, 196, 197, 198 or 199 picomolar, and in some embodiments, the antibodies may have even higher affinity for KDR.

The term "immunologically active", with reference to an epitope being or "remaining immunologically active", refers to the ability of an antibody (e.g., anti-KDR antibody) to bind to the epitope under different conditions, for example, after the epitope has been subjected to reducing and denaturing conditions.

An antibody or antigen-binding fragment thereof according to certain preferred embodiments of the present application may be one that competes for binding to KDR with any antibody described herein which both (i) specifically binds to the antigen and (ii) comprises a VH and/or VL domain disclosed herein, or comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Thus, there is provided herein a specific antibody or antigen-binding fragment thereof, comprising a human antibody antigen-binding site which competes with an antibody described herein that binds to KDR.

In this regard, as used herein, the terms "competes with", "inhibits binding" and "blocks binding" (e.g., referring to inhibition/blocking of binding of VEGF to KDR or referring to inhibition/blocking of binding of an anti-KDR antibody to KDR) are used interchangeably and encompass both partial and complete inhibition/blocking. The inhibition/blocking of VEGF binding to KDR preferably reduces or alters the normal level or type of cell signaling that occurs when VEGF binds to KDR without inhibition or blocking. Inhibition and blocking are also intended to include any measurable decrease in the binding of VEGF to KDR when in contact with an anti-KDR antibody as disclosed herein as compared to the ligand not in contact with an anti-KDR antibody, e.g., the blocking of VEGF to KDR by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1 E4K) (Sondermann et al., 2000, Nature 406:267-273) (pdb accession codes 1 IIS and 1 IIX)(Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of DEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758). Thus 80-90% of humans are poor responders; that is they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of an KDR-specific antibody as described herein to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-KDR antibodies having a modified Fc region with altered functional properties, such as reduced or enhanced CDC, ADCC, or ADCP activity, or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

Thus, in certain embodiments, antibody variable domains with the desired binding specificities are fused to immunoglobulin constant domain sequences. In certain embodiments, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020, or EP Patent 0 425 235 B1, and Chari et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

In another contemplated embodiment, a KDR-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforemention therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda K, et al., The Prostate 70:1286-1294 (2010); Lip, W L. et al., 2007 Molecular Pharmaceutics 4:241-251; Quadros E V., et al., 2010 Mol Cancer Ther; 9(11); 3033-40; Polito L., et al. 2009 British Journal of Haematology, 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, gelonin, *Pseudomonas* exotoxin (PE40), *Shigella* toxin, *Clostridium perfringens* toxin, and pokeweed antiviral protein.

In one embodiment, an antibody or antigen-binding fragment thereof of the disclosure is conjugated to one or more maytansinoid molecules. Maytansinoids are mitotic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

Another conjugate of interest comprises an antibody conjugated to one or more calicheamicin molecules. The calicheamicin family of antibiotics is capable of producing double-stranded DNA breaks at sub-picomolar concentrations. Structural analogues of calicheamicin that may also be used (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264,586; U.S. Pat. No. 5,773,001). Dolastatin 10 analogs such as auristatin E (AE) and monomethylauristatin E (MMAE) may find use as conjugates for the presently disclosed antibodies, or variants thereof (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, PCT WO 93/21232. The present disclosure further contemplates embodiments in which a conjugate or fusion is formed between an KDR-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies.

Examples include, but are not limited to $^{90}$Y, $^{123}$I, $^{125}$I, $^{131}$I, $^{186}$Re, $^{188}$Re, $^{211}$At, and $^{212}$Bi.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. One preferred exemplary cytotoxin is saporin (available from Advanced Targeting Systems, San Diego, Calif.). Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and antimitotic agents (e.g., vincristine and vinblastine).

Moreover, a KDR-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, Nature 328: 457-458). Antibody-abzyme conjugates can be prepared for delivery of the abzyme to a tumor cell population.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

Other modifications of the antibodies (and polypeptides) of the invention are also contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

The desired functional properties of anti-KDR antibodies may be assessed using a variety of methods known to the skilled person affinity/binding assays (for example, surface plasmon resonance, competitive inhibition assays); cytotoxicity assays, cell viability assays, cell proliferation or differentiation assays in response to VEGF (e.g., phosphorylation assays), cancer cell and/or tumor growth inhibition using in vitro or in vivo models. Other assays may test the ability of antibodies described herein to block normal VEGF/KDR-mediated responses, such as, but not limited to, phosphorylation of KDR, angiogenesis, and endothelial cell proliferation. The antibodies described herein may also be tested for effects on KDR receptor internalisation, in vitro and in vivo efficacy, etc. In further embodiments, the antibodies herein may be tested in vivo using appropriate animal models. The antibodies described herein may be tested in vitro or in vivo for their ability to inhibit tumor growth. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies that bind KDR as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasm id-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-KDR antibodies described herein. In certain embodiments, polynucleotides are provided that comprise some or all of a polynucleotide sequence encoding an antibody as described herein and complements of such polynucleotides.

In other related embodiments, polynucleotide variants may have substantial identity to a polynucleotide sequence encoding an anti-KDR antibody described herein. For example, a polynucleotide may be a polynucleotide comprising at least 70% sequence identity, preferably at least 75%; 80%, 85%, 90%, 95%, 96%, 97%, 98%, or 99% or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an antibody as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody, or antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody described herein or at both ends of a polynucleotide encoding an antibody described herein.

In another embodiment, polynucleotides are provided that are capable of hybridizing under moderate to high stringency conditions to a polynucleotide sequence encoding an antibody, or antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies that bind KDR, or antigen-binding fragments thereof. In other embodiments, such polynucleotides encode antibodies or antigen-binding fragments, or CDRs thereof, that bind to KDR at least about 50%, at least about 70%, and in certain embodiments, at least about 90% as well as an antibody sequence specifically set forth herein. In further embodiments, such polynucleotides encode antibodies or antigen-binding fragments, or CDRs thereof, that bind to KDR with greater affinity than the antibodies set forth herein, for example, that bind quantitatively at least about 105%, 106%, 107%, 108%, 109%, or 110% as well as an antibody sequence specifically set forth herein.

As described elsewhere herein, determination of the three-dimensional structures of representative polypeptides (e.g., variant KDR-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequences that encode antibodies that bind to KDR. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In many embodiments, the nucleic acids encoding a subject monoclonal antibody are introduced directly into a host cell, and the cell incubated under conditions sufficient to induce expression of the encoded antibody. The antibodies of this disclosure are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antigen-binding fragments in prokaryotic cells such as E. coli is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as a KDR-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS 1N MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to KDR of the present disclosure, or sequences that have deletions from, additions to, and/or substitutions of one or more amino acid of an anti-KDR antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-KDR antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support.

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., Gene 40:39 46 (1985); Murphy et al., *Proc. Natl. Acad. Sci. USA* 83:8258 8262 (1986); U.S. Pat. No. 4,935,233 and U.S. Pat. No. 4,751,180.

Other illustrative spacers may include, for example, Glu-Gly-Lys-Ser-Ser-Gly-Ser-Gly-Ser-Glu-Ser-Lys-Val-Asp (SEQ ID NO:231) (Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (SEQ ID NO:232) (Bird et al., 1988, Science 242:423-426).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO:233) repeated 1 to 3 times. Such a spacer has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide spacer, in certain embodiments, is designed to enable the correct interaction between two beta-sheets forming the variable region of the single chain antibody.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to KDR). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies disclosed herein. In certain embodiments, such variant antibodies or antigen-binding fragments, or CDRs thereof, bind to KDR at least about 50%, at least about 70%, and in certain embodiments, at least about 90% as well as an antibody sequence specifically set forth herein. In further embodiments, such variant antibodies or antigen-binding fragments, or CDRs thereof, bind to KDR with greater affinity than the antibodies set forth herein, for example, that bind quantitatively at least about 105%, 106%, 107%, 108%, 109%, or 110% as well as an antibody sequence specifically set forth herein.

In particular embodiments, a subject antibody may have: a) a heavy chain variable region having an amino acid sequence that is at least 80% identical, at least 95% identical, at least 90%, at least 95% or at least 98% or 99% identical, to the heavy chain variable region of an anti-KDR antibody described herein; and b) a light chain variable region having an amino acid sequence that is at least 80% identical, at least 85%, at least 90%, at least 95% or at least 98% or 99% identical, to the light chain variable region of an anti-KDR antibody described herein. The amino acid sequence of illustrative heavy and light chain regions are set forth in SEQ ID NOs:1, 2, 9 and 10).

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., KDR). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167).

Determination of the three-dimensional structures of representative polypeptides (e.g., variant KDR-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. Science 327:1014-1018 (2010). Some additional non-limiting examples of computer algorithms that may be used for these and related embodiments, such as for rational design of KDR-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

In another embodiment of invention, the anti-KDR antibodies and humanized versions thereof are derived from rabbit monoclonal antibodies, and in particular are generated using RabMAb® technology. These antibodies are advantageous as they require minimal sequence modifications, thereby facilitating retention of functional properties after humanization using mutational lineage guided (MLG) humanization technology (see e.g., U.S. Pat. No. 7,462,697). Thus, illustrative methods for making the anti-KDR antibodies of the present disclosure include the RabMab® rabbit monoclonal antibody technology described, for example, in U.S. Pat. Nos. 5,675,063 and 7,429,487. In this regard, in certain embodiments, the anti-KDR antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions and Methods of Use

The present disclosure provides compositions comprising the KDR-specific antibodies, antigen-binding fragments thereof and administration of such composition in a variety of therapeutic settings.

Administration of the KDR-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in symptoms of disorders associated with VEGF or KDR expression and/or activity, including but not limited to any of a variety of oncological diseases, inflammatory diseases, and angiogenesis-related diseases. Thus, a therapeutically effective amount of one or more of the antibodies described herein is administered to result in clinically relevant reduction in symptoms of disorders including, but not limited to, rheumatoid arthritis, diabetes and ischemic retinopathies, age-related macular degeneration, psoriasis and glomerular hypertrophy associate with proteinuria and a variety of oncological diseases including angiosarcoma, renal cell carcinoma, gastrointestinal cancer, metastatic gastric or gastroesophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors. Such clinically relevant symptoms are known to the skilled clinician and will vary depending on the disease indication being treated.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The KDR-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described KDR-specific antibody in aerosol form may hold a plurality of dosage units. Actual methods of preparing such dosage forms are known, or will be apparent, to those skilled in this art; for example, see

*Remington: The Science and Practice of Pharmacy*, 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an KDR-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an KDR-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., KDR-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g). As would be recognized by the skilled person, in certain embodiments, it may be preferable to use doses expressed as milligrams per meter squared (i.e., mg/m$^2$). For example, to express a mg/kg dose in any given species as the equivalent mg/m$^2$ dose, multiply the dose by the appropriate km factor. In adult humans, 100 mg/kg is equivalent to 100 mg/kg×37 kg/m$^2$=3700 mg/m$^2$. See e.g., FDA guidelines for Industry and Reviewers; see also Freireich, E J, et al. Quantitative comparison of toxicity of anticancer agents in mouse, rat, dog, monkey and man. *Cancer Chemother Rep.* 1966; 50(4):219-244.

Compositions comprising the KDR-specific antibodies of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Similarly, an antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of anti-KDR antibody compositions of this disclosure in combination with one or more other therapeutic agents. Such therapeutic agents may be accepted in the art as a standard treatment for a particular disease state as described herein, such as inflammatory disease (e.g., rheumatoid arthritis, or other inflammatory disorder), any of a variety of oncological diseases, and angiogenesis-mediated diseases (such as, but not limited to age-related macular degeneration). Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the anti-KDR antibodies disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; am inopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the anti-KDR antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

The compositions comprising herein described KDR-specific antibodies may be administered to an individual afflicted with a disease as described herein, including, but not limited to disorders associated with VEGF or KDR expression and/or activity, including but not limited to, rheumatoid arthritis, diabetes and ischemic retinopathies, age-related macular degeneration, psoriasis and glomerular hypertrophy associate with proteinuria and a variety of oncological diseases including angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors. For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising KDR-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Provided herein are methods of treatment using the antibodies that bind KDR. In one embodiment, an antibody of the present invention is administered to a patient having a disease involving inappropriate expression of KDR, which is meant in the context of the present disclosure to include diseases and disorders characterized by aberrant KDR expression or activity, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of KDR relative to that which is normally detectable. Such an overabundance of KDR can be measured relative to normal expression, appearance, or activity of KDR signalling events, and said measurement may play an important role in the development and/or clinical testing of the antibodies described herein.

In particular, the present antibodies are useful for the treatment of a variety of cancers associated with the expression of KDR. For example, one embodiment of the invention provides a method for the treatment of a cancer including, but not limited to, disorders associated with VEGF or KDR expression and/or activity, including but not limited to, a variety of oncological diseases including angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors, by administering to a cancer patient a therapeutically effective amount of a herein disclosed KDR-specific antibody. An amount that, following administration, inhibits, prevents or delays the progression and/or metastasis of a cancer in a statistically significant manner (i.e., relative to an appropriate control as will be known to those skilled in the art) is considered effective.

Another embodiment provides a method for preventing metastasis of a cancer including, but not limited to, cancers including, but not limited to, a variety of oncological diseases including angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors, by administering to a cancer patient a therapeutically effective amount of a herein disclosed KDR-specific antibody (e.g., an amount that, following administration, inhibits, prevents or delays metastasis of a cancer in a statistically significant manner, i.e., relative to an appropriate control as will be known to those skilled in the art).

Another embodiment provides a method for preventing a cancer including, but not limited to, cancers including, but not limited to, a variety of oncological diseases including angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors, by administering to a cancer patient a therapeutically effective amount of a herein disclosed KDR-specific antibody.

Another embodiment provides a method for treating, inhibiting the progression of or prevention of cancers including, but not limited to, a variety of oncological diseases such as angiosarcoma, renal cell carcinoma, gastrointestinal cancer, metastatic gastric or gastro-esophageal junction adenocarcinoma, breast cancer, bladder cancer, hepatocellular carcinoma, colorectal cancer, prostate cancer, non-small cell lung cancer, neuroblastoma, ovarian cancers, melanoma, and recurrent glioblastoma multiforme, leukemias and solid tumors, and other disorders associated with VEGF or KDR expression and/or activity, including but not limited to, rheumatoid arthritis, diabetes and ischemic retinopathies, age-related macular degeneration, psoriasis and glomerular hypertrophy associate with proteinuria, by administering to a patient afflicted by one or more of these diseases a therapeutically effective amount of a herein disclosed KDR-specific antibody.

In further embodiments, the present antibodies are useful for the treatment of a variety of inflammatory diseases. For example, one embodiment of the invention provides a method for the treatment of an inflammatory disease including, but not limited to, inflammatory disorders associated with VEGF or KDR expression and/or activity, including but not limited to, rheumatoid arthritis, diabetes, gout, cryopyrin-associated periodic syndrome, chronic obstructive pulmonary disorder and various cardiovascular diseases such as atherosclerosis and vasculitis. The present antibodies are useful for the treatment of inflammatory syndromes characterized by attacks of sterile inflammation of joints, serositis, fever, and skin lesions. Inflammatory diseases include, but are not limited to, Crohn's disease, colitis, dermatitis, psoriasis, diverticulitis, hepatitis, irritable bowel syndrom (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In one embodiment, the present disclosure provides a method of treating, reducing the severity of or preventing inflammation or an inflammatory disease by administering to a patient in need thereof a therapeutically effective amount of a herein disclosed composition.

In another embodiment, anti-KDR antibodies of the present invention are used to determine the structure of bound antigen, e.g., conformational epitopes, which structure may then be used to develop compounds having or mimicking this structure, e.g., through chemical modeling and SAR methods.

Various other embodiments of the present invention relate, in part, to diagnostic applications for detecting the presence of cells or tissues expressing KDR. Thus, the present disclosure provides methods of detecting KDR in a sample, such as detection of cells or tissues expressing KDR. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA).

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies described herein are conjugated to a detectable label that may be detected directly or indirectly. In this regard, an antibody "conjugate" refers to an anti-KDR antibody that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting KDR or cells or tissues expressing KDR in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

EXAMPLES

Example 1

Production and Humanization of Anti-Kdr Antibodies

Anti-KDR Antibody Generation

New Zealand white rabbits were immunized with recombinant KDR-rabbit Fc fusion protein. The rabbit with the highest serum titers of specific binding to human KDR was chosen for hybridoma generation. A total of 230 hybridomas were identified as positive for binding to soluble KDR-Fc. Of these 230, 100 clones were also found positive for binding to cell surface KDR through the use of KDR-transfectant 293 cells. The double positive hybridomas were selected for further functional characterization.

Functional Screening of Hybridomas

Screening for functional antibodies that block binding of KDR to VEGF: The double positive anti-KDR antibodies (100 clones) that bind both soluble KDR and cell surface KDR were assessed for their ability to inhibit the binding of KDR to VEGF. Out of 100 anti-KDR clones, 41 were found to exhibit inhibition and were recombinantly expressed and purified for further characterization. The potency of the top 10 anti-KDR antibodies that inhibited the binding of KDR to VEGF is summarized in Table 2 below and is shown in FIG. 1.

TABLE 2

| IC50 of Anti-KDR Antibodies | |
|---|---|
| Antibody | IC50 (nM) |
| 15 | 17.48 |
| 23 | 21.37 |
| 24 | 19.83 |
| 27 | 5.95 |
| 36 | 6.25 |
| 43 | 7.54 |
| 71 | 9.94 |
| 81 | 4.56 |
| 83 | 9.77 |
| 92 | 32.94 |

Figure 2A:
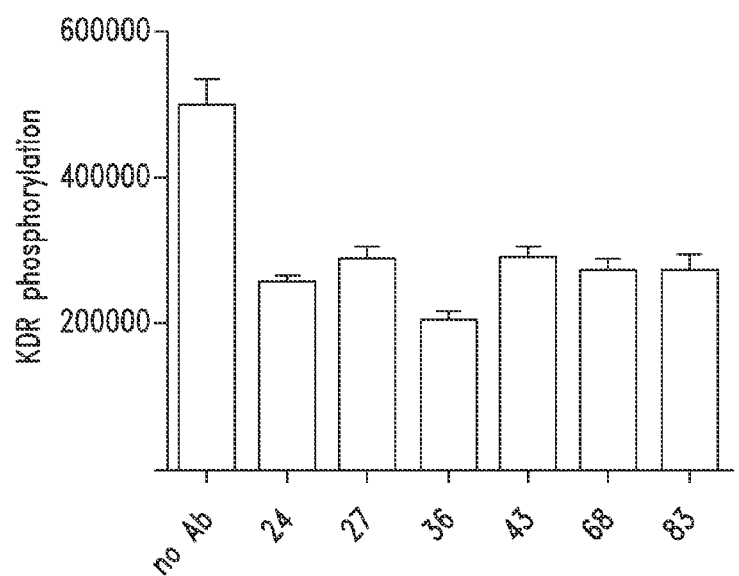
FIG. 2: Screening for antibodies that inhibit the phosphorylation of KDR. (A) Inhibition of KDR phosphorylation in ELISA assay; (B) Inhibition of KDR phosphorylation in Western blot. Ab9530 is a control KDR neutralizing antibody from Abcam (Cambridge, Mass., USA).
Figure 2B:
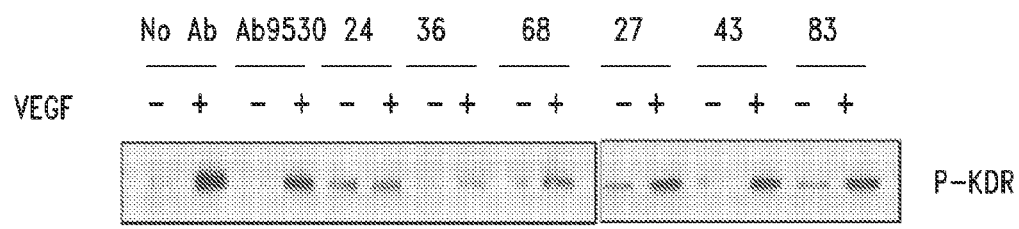

Screening for antibodies that inhibit KDR phosphorylation: The top 10 anti-KDR antibodies selected based on the ligand receptor binding assay were further tested in a cell-based KDR phosphorylation assay using HUVEC cells. Cultured HUVEC cells were treated with anti-KDR antibodies at 5 µg/ml (a relatively saturated dose) for 1 hour at 37° C. before adding 20 ng/ml (an optimal stimulation dose) of human VEGF (R&D System). The harvested cell lysates were quantified by protein concentration. The phosphorylation of KDR was determined using a phosphor ELISA assay using a rabbit anti-KDR YK-5 (a non-functional anti-KDR clone) as the capture antibody and a mouse anti-phosphotyrosine, P-Tyr-100 (Cell Signaling Technology) as the detection antibody. The top 6 clones that inhibit KDR phosphorylation are shown in FIG. 2. Of the top 6 clones, clone 36 exhibited the strongest inhibition of VEGF-stimulated KDR phosphorylation (FIG. 2A). The phosphor ELISA result of clone 36 was further confirmed by Western blot (FIG. 2B) using anti-phosphor-KDR Y996 polyclonal antibody (Epitomics, Burlingame, Calif.).

Screening for Cross Species Anti-KDR Antibodies:

In order to evaluate the efficacy of blocking KDR therapy in in vivo animal studies, in which KDR is only expressed on endothelial cells of the host, the top 6 anti-KDR antibodies were screened for cross reactivity with mouse KDR. Antibodies #27, #36, #43, #68, #83 were found to be cross-reactive with both human and mouse KDR (data not shown). Table 3 below summarizes three groups of rabbit antibodies identified in the screen as follows: 1) Anti-human KDR antibodies that block KDR phosphorylation, and also cross react with mouse KDR, including clones 4, 6, 14, 27, 30, 36, 68, 69, 81, 83, 91 and 95; 2) Anti-human KDR antibodies that block KDR phosphorylation but do not cross-react with mouse KDR, including clones 5, 13, 15, 17, 23, 24, 25, 43, 71, 77, 92 and 93; 3) Anti-human KDR antibodies that cross-react with mouse KDR but do not block KDR phosphorylation, including clones 40, 42 and 50.

TABLE 3

Anti-KDR Rabbit Antibodies Summary

| Anti-KDR clone | Mouse reactive | Blocking KDR phosphorylation | VH amino acid SEQ ID NO | VL amino acid SEQ ID NO |
|---|---|---|---|---|
| 4 | + | + | 17 | 43 |
| 5 | − | ++ | 18 | 44 |
| 6 | + | + | 19 | 45 |
| 13 | − | +++ | 20 | 46 |
| 14 | + | ++ | 21 | 47 |
| 15 | − | + | 22 | 48 |
| 17 | − | + | 23 | 49 |
| 23 | − | ++ | 24 | 50 |
| 24 | − | +++ | 25 | 51 |
| 25 | − | +++ | 26 | 52 |
| 27 | + | ++ | 27 | 53 |
| 30 | + | ++ | 28 | 54 |
| 36 | + | +++ | 1 | 2 |
| 40 | + | − | 29 | 55 |
| 42 | + | − | 30 | 56 |
| 43 | − | +++ | 31 | 57 |
| 50 | + | − | 32 | 58 |
| 68 | + | ++ | 33 | 59 |
| 69 | + | +++ | 34 | 60 |
| 71 | − | + | 35 | 61 |
| 77 | − | ++ | 36 | 62 |
| 81 | + | + | 37 | 63 |
| 83 | + | ++ | 38 | 64 |
| 91 | + | + | 39 | 65 |
| 92 | − | +++ | 40 | 66 |
| 93 | − | +++ | 41 | 67 |
| 95 | + | ++ | 42 | 68 |

FIG. 11 shows an alignment of the VH and VL regions of the anti-KDR antibodies. The CDRs are underlined. The VHCDR1 amino acid sequences are provided in SEQ ID Nos:69-95; the VHCDR2 amino acid sequences are provided in SEQ ID Nos:96-122; he VHCDR3 amino acid sequences are provided in SEQ ID Nos:123-149; the VLCDR1 amino acid sequences are provided in SEQ ID Nos:150-176; the VLCDR2 amino acid sequences are provided in SEQ ID Nos:177-203; the VLCDR3 amino acid sequences are provided in SEQ ID Nos:204-230.

Based on the potency of anti-phosphorylation of human KDR and cross reactivity to mouse KDR, clone 36 was selected as the first candidate anti-KDR antibody.

Recombinant Anti-KDR Antibody Clone 36

DNA fragments of L chains and the variable region (VH) of H chains of rabbit IgG from clone 36 were amplified by PCR. The L chain fragment was cloned into pTT5 vector at Hind III and Not I sites and the VH fragment into the constant region of H chain built-in pTT5 vector at Hind III and Kpn I sites. For each hybridoma, three DNA clones of L or H chain were sequenced and the plasmid with a consensus sequence was identified and used for recombinant expression. To express the recombinant antibody, the L and H chain plasm ids were co-transfected into 293-6E cells (National Research Council Canada). The supernatants were harvested 5 days later and quantified using an ELISA assay to measure the IgG concentration before functional assays.

Humanization Design

Mutational lineage guided (MLG) humanization technology was used to humanize the lead clone 36. First, the heavy chain (VH) and light chain (VK) variable region sequences of clone 36 were blasted against the human germline VH and VK database. The closest human germline sequences were identified as the template for humanization. Secondly, the rabbit residues in the framework regions potentially involved in CDR contacts or inter-chain contacts were identified based on knowledge from human and rabbit antibodies. Residues considered not critical to the structural activity of the antibodies were identified based on knowledge from previous humanized rabbit antibodies.

The light and heavy chain frameworks of the humanized 36 (APX004) are 93% identical to the human germline sequences. In addition to humanization of the frameworks, the MLG method allowed us to further humanize both CDR1 and CDR2 of the heavy chain from 47% to 58% homology to human germline sequences. The binding potency of APX004 to KDR was found to be similar to its parental rabbit monoclonal antibody 36 (See FIG. 4). The amino acid sequences of the humanized VH and VL regions for clone 36 are set forth in SEQ ID NOs:9 and 10, respectively. The amino acid sequence of the VHCDR1 and VHCDR2 of the humanized clone 36 are set forth in SEQ ID NOs:11 and 12. The amino acid sequence of the VHCDR3 of the humanized clone 36 anti-KDR antibody (APX004) is the same as the parental VHCDR3 as set forth in SEQ ID NO:5. The amino acid sequences of the VLCDR1, VLCDR2 and VLCDR3 of the humanized clone 36 anti-KDR antibody (APX004) are the same as the rabbit parental VLCDR sequences as set forth in SEQ ID NOs:6-8.

Expression of Humanized Clone(s)

DNA encoding humanized VK and VH of clone R-36 was synthesized by MCLab (South San Francisco, Calif., USA). The DNA fragments include signal peptide and a Kozak sequence at the 5' end. To express the humanized version of clone 36, the humanized VK fragment was cloned into human CK built-in pTT5 vector at Hind III and Nhe I. The humanized VH was cloned into human IgG1 CH1 built-in pTT5 vector at Hind III and BsiW I site. DNA and amino acid sequences of human CK (SEQ ID NOs:13 and 14, respectively) and IgG1 CH1 (SEQ ID NOs:15 and 16, respectively) were chosen for the constant region. Humanized versions of clone 36 were expressed in 293-6E cells, purified through a protein A column and quantified by UV280 after dialyzing against PBS buffer.

Example 2

Binding Selectivity of APX004

APX004 is a humanized IgG1 antibody against KDR (VEGFR2). It binds with high affinity (Kd=$5.3 \times 10^{-11}$ M) and specificity to human KDR. APX004 cross reacts with monkey and mouse KDR. APX004 blocks the binding of KDR to VEGF and inhibits KDR phosphorylation, resulting in inhibition KDR downstream signaling and biologic functions, such as endothelial cell proliferation and angiogenesis.

Binding selectivity of APX004 was assessed by direct ELISA to VEGFR family proteins. A total of 1 µg/ml of rabbit Fc-fusion protein of human KDR, mouse KDR, human VEGFR1, human VEGFR3, human OX40L and human VEGF were coated on ELISA plates followed by incubation with 1 µg/ml of APX004. Bound APX004 was detected using goat anti-human HRP-conjugated IgG.

Figure 3:
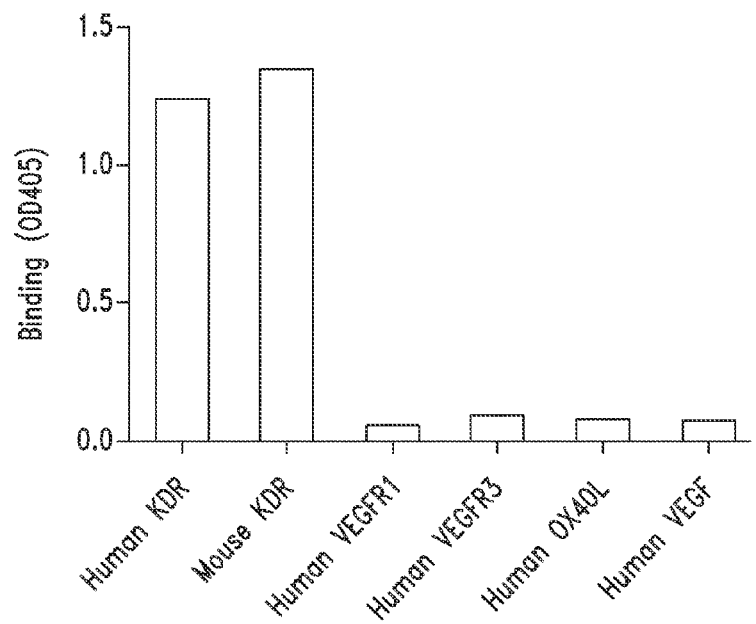
FIG. 3: APX004 binds selectively to human and mouse KDR but not to other human VEGFR family proteins or VEGF.

As shown in FIG. 3, APX004 binds selectively to human and mouse KDR but not to other human VEGFR family proteins or VEGF. Thus APX004 can be tested in mouse tumor models for in vivo efficacy and PK studies. Since monkey KDR shares 99.9% sequence identity (only a conserved amino acid difference in the non-ligand binding domain) to human KDR in the extra cellular domain, APX004 should be able to recognize monkey KDR.

Example 3

APX004 Blocks Binding of Kdr to Vegf

An ELISA-based KDR-VEGF binding assay was developed and used to assess the potency of APX004 at blocking KDR binding to VEGF. A total of 2 µg/ml VEGF was coated on ELISA plates. APX004, the parental rabbit antibody R-36 or IgG1 isotype control antibody were pre-incubated with 5 µg/ml recombinant human KDR before being transferred to the VEGF-A coated ELISA plates. KDR bound to immobilized VEGF was detected by a mouse anti-KDR monoclonal antibody, followed by the addition of goat anti-mouse IgG conjugated with alkaline phosphatase (Fisher Scientific/Pierce Biotechnology, Rockford, Ill.). ELISA plates were developed with p-nitrophenyl phosphate substrate and absorbance at 405 nm was recorded. All experiments were performed in triplicate.

Figure 4:
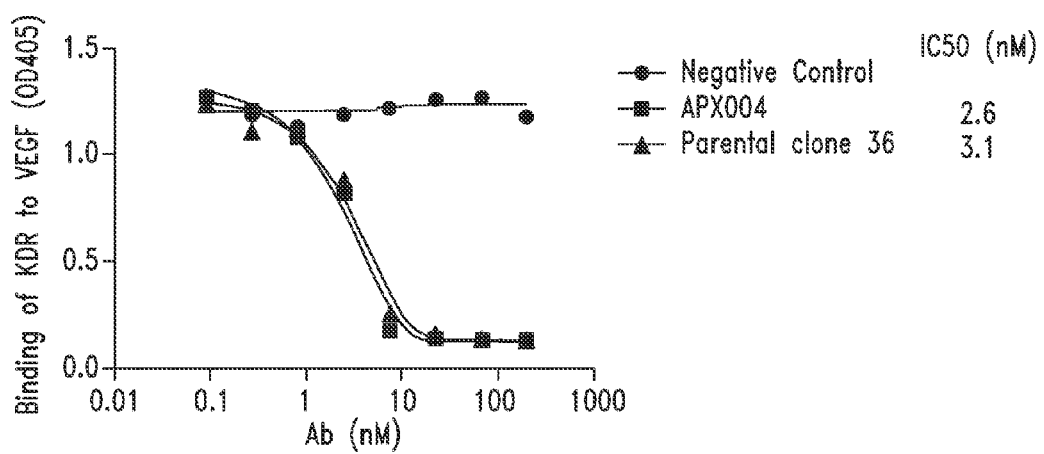
FIG. 4: APX004 potently blocks the binding of KDR to VEGF with IC50 of 2.6 nM.

As shown in FIG. 4, APX004 potently blocks the binding of KDR to VEGF with IC50 of 2.6 nM. Humanization of R-36 did not affect its potency to inhibit KDR binding to VEGF.

Example 3

Inhibition of KDR Phosphorylation by APX004

Figure 5:
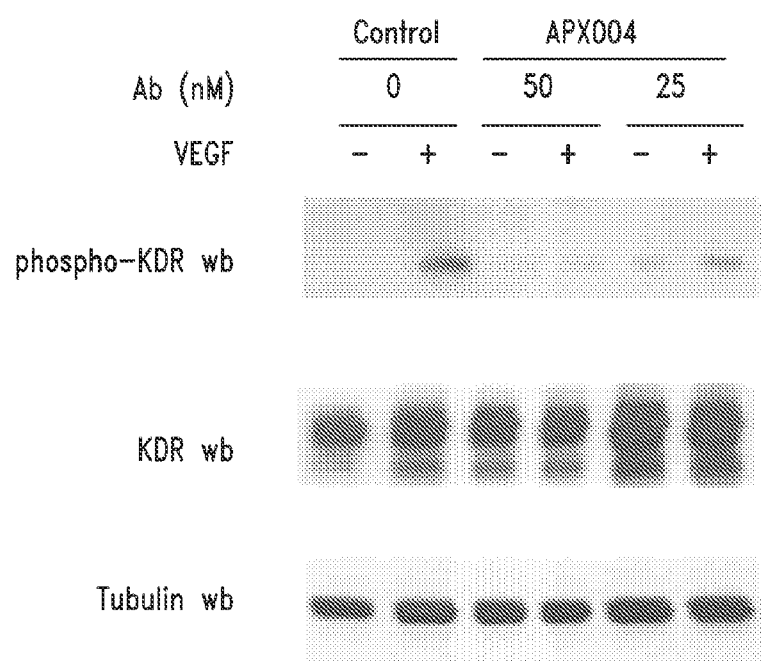
FIG. 5: APX004 inhibited the KDR phosphorylation induced by VEGF.

To assess the inhibitory effect of APX004 on VEGF-induced KDR phosphorylation, antibodies at various concentrations were pre-incubated with cultured HUVEC cells for 1 h before adding 5 nM of human VEGF (R&D System). The KDR phosphorylation was detected by Western blot. Cell lysates from treated HUVEC cells containing equal amounts of protein were resolved on 4-20% SDS-PAGE gel and the proteins were transferred to a PVDF membrane (Millipore, Billerica, Mass.). The blots were probed sequentially with anti-phosphor-KDR antibody, total KDR antibody and anti-alpha-tubulin antibody (Epitomics). Primary antibody was stripped by washing in glycine buffer before re-probing with another primary antibody. The specific signals were visualized on X-ray film after incubation of blotted membrane with appropriate horseradish peroxidase—conjugated secondary antibodies (Fisher Scientific/Pierce Biotechnology), followed by ECL reagent development (GE Healthcare Bio-Sciences). As shown in FIG. 5, APX004 inhibited the KDR phosphorylation induced by VEGF.

Example 4

Inhibition of HUVEC Proliferation by APX004

Figure 6:
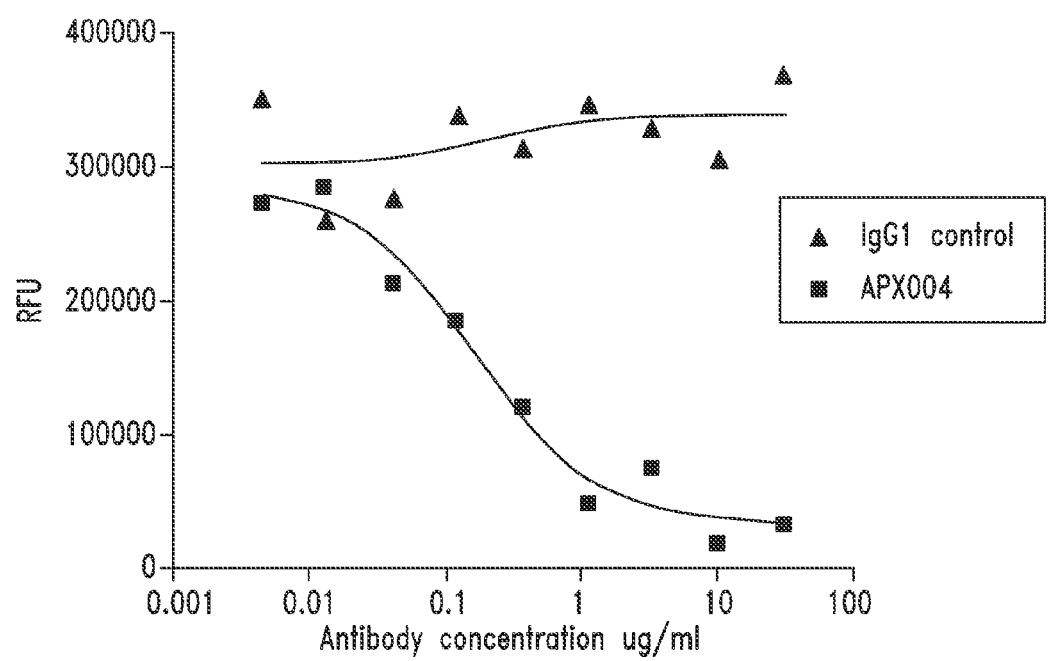
FIG. 6: APX004 inhibits HUVEC proliferation in a dose-dependent manner.

To determine the inhibitory effect of APX004 on VEGF-induced HUVEC proliferation, various concentrations of APX004 were added to HUVEC cultures at 4,000 cells/well in a 96-well plate and incubated for 1 hour before adding 15 ng/ml of VEGF (final concentration). HUVEC cells were further incubated at 37° C. for 72 hours before 10% AlamarBlue® was added to each well. After 24 hour incubation, HUVEC cell viability was measured by reading the fluoresence intensity using Wallac Victor V 1420 Multilabel HTS Counter (PerkinElmer) with excitation at 530 nm and emission at 590 nm. All assays were done in triplicate. As shown in FIG. 6, APX004 inhibits HUVEC proliferation in a dose-dependent manner.

Example 5

Inhibition of Tumor Growth in Human Lung Cancer H460 Model

One of the advantages of APX004 over Ramucirumab is that APX004 cross reacts with mouse KDR. Thus, APX004 can be directly evaluated in human tumor xenograft models in mice. The in vivo anti-angiogenesis and anti-tumor efficacy of APX004 was shown in multiple tumor xenograft models.

Figures 7A, 7B:
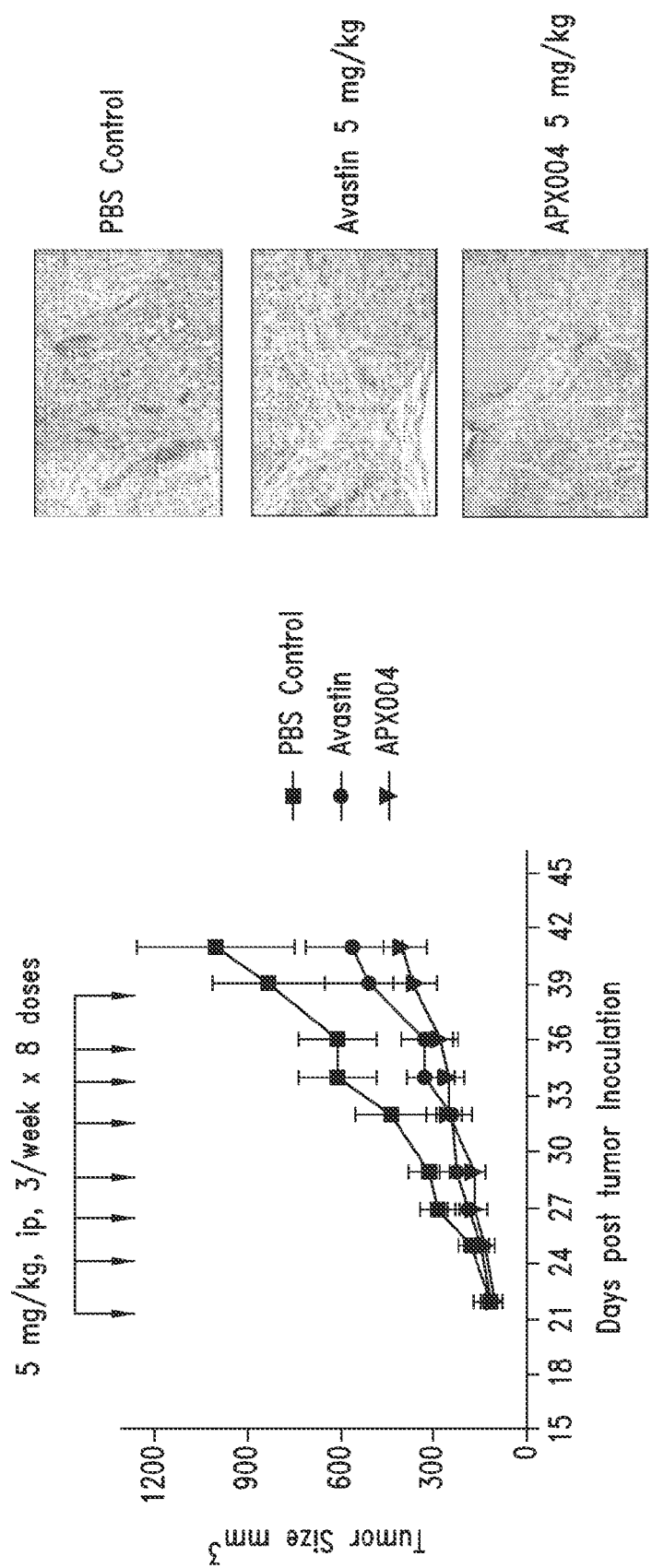
FIGS. 7A and 7B: APX004 exhibited more potent anti-tumor activity (77% inhibition) than Avastin® (69% inhibition) by the termination of an in vivo study (Day 41).

To evaluate the in vivo efficacy of APX004 in the human H460 xenograft model, human NSCLC tumor H460 (KDR negative) xenografts were established by subcutaneous inoculation of human NSCLC cell line H460 into the dorsal flanks of female BALB/c nude mice. When tumor sizes reached an average volume of 200 mm$^3$ at day 22, the tumor bearing mice were randomized into 3 treatment groups as indicated (n=8-10). Then the randomized groups received ip injections of a 5 mg/kg/dose of APX004 or Avastin® at 3 times/week for a total of 8 doses. Tumor volumes and body weights were calculated according to the following equation: Volume=(width)$^2$×length/2 every 2 to 3 days (FIG. 7A). Photomicrophraphs of immunohistochemistry staining with an anti-CD34 mAb (×400) was performed to illustrate microvasculature density (brown color)(FIG. 7B).

APX004 exhibited more potent anti-tumor activity (77% inhibition) than Avastin® (69% inhibition) at the termination of study (Day 41). APX004 treatment resulted in reduction of tumor microvasculature (CD34$^+$ EC staining). APX004 did not show significant toxicity (i.e., there was no change in body weight relative to the control group).

Example 6

Dose Response Inhibition in Human Lung Cancer H460 Model

Figure 8:
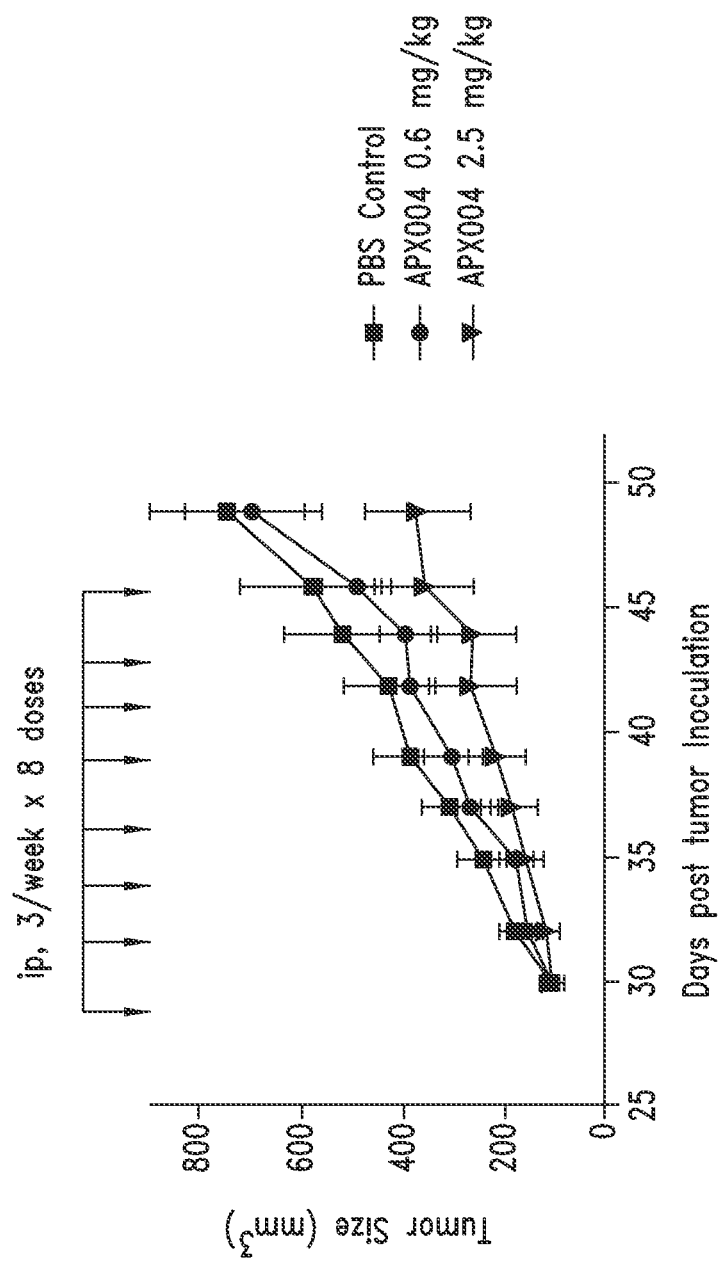
FIG. 8: APX004 demonstrated a significant anti-tumor activity at a dose of 2.5 mg/kg (p<0.01) in the H460 tumor model.

To determine the effective dose of APX004 in the human H460 xenograft model, human NSCLC tumor H460 xenografts were established by subcutaneous inoculation of human NSCLC cell line H460 into the dorsal flanks of female BALB/c nude mice. When tumors reached an average volume of 160 mm$^3$, the tumor bearing mice were randomized into 3 treatment groups as indicated (n=8-10). APX004 was administered intraperitoneally at 2.5 mg/kg or 0.6 mg/kg 3 times/week for a total of 8 doses. Tumor size and body weight were recorded every 2 to 3 days. Tumor volumes were calculated according to the following equation: Volume=(width)$^2$×length/2. As shown in FIG. 8, APX004 demonstrated a significant anti-tumor activity at a dose of 2.5 mg/kg (p<0.01) in the H460 tumor model. APX004 did not show significant toxicity (no change of body weight relative to the control group).

Example 7

Inhibition of Tumor Growth in Human Melanoma A375 Model

Figure 9:
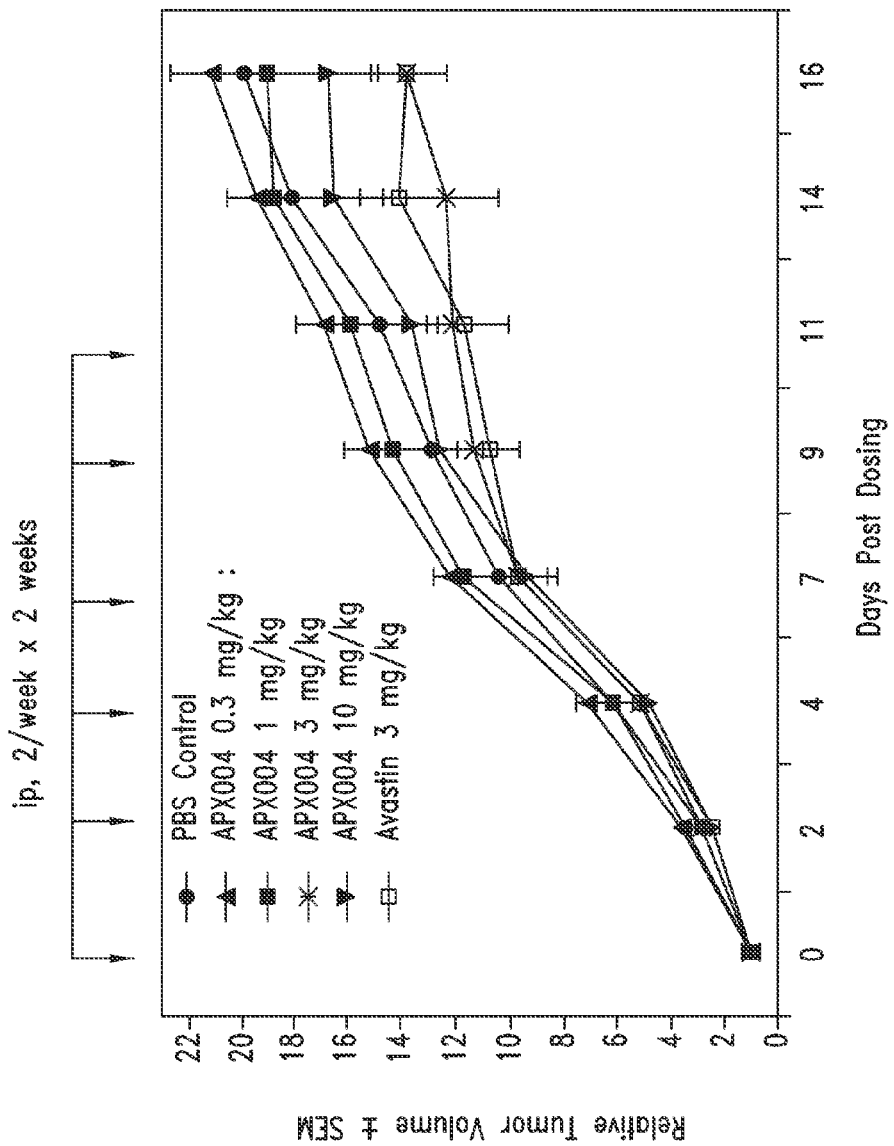
FIG. 9: APX004 significantly inhibits A375 tumor growth at 3 mg/kg. Volume=(width)$^2$×length/2. Symbols and bars, mean+standard deviation.

To determine the effect of APX004 on tumor growth in the human A375 xenograft model, human melanoma tumor xenografts were established by subcutaneous inoculation of human A375 cells into the dorsal flanks of female BALB/c nude mice. When tumors reached an average volume of 100 mm$^3$, the tumor bearing mice were randomized into 6 treatment groups as indicated. Various doses of APX004 or 3 mg/kg of Avastin® were administered intraperitoneally twice weekly for 3 weeks for a total of 6 doses. Tumor size and body weights were recorded every 3 days. Perpendicular dimensions of the tumor were measured using a Vernier scale caliper. Tumor volumes were calculated according to the following equation: Volume=(width)$^2$×length/2. Symbols and bars, mean+standard deviation. As shown in FIG. 9, APX004 significantly inhibits A375 tumor growth at 3 mg/kg. At this dose, APX004 exhibits anti-tumor activity similar to that of Avastin®. The data suggested that the A375 model is less dependent on VEGF-KDR pathways. Therefore, no apparent dose-dependent anti-tumor effect was observed.

Example 8

Inhibition of Tumor Growth in Human Colon Cancer HT29 Model

Figure 10:
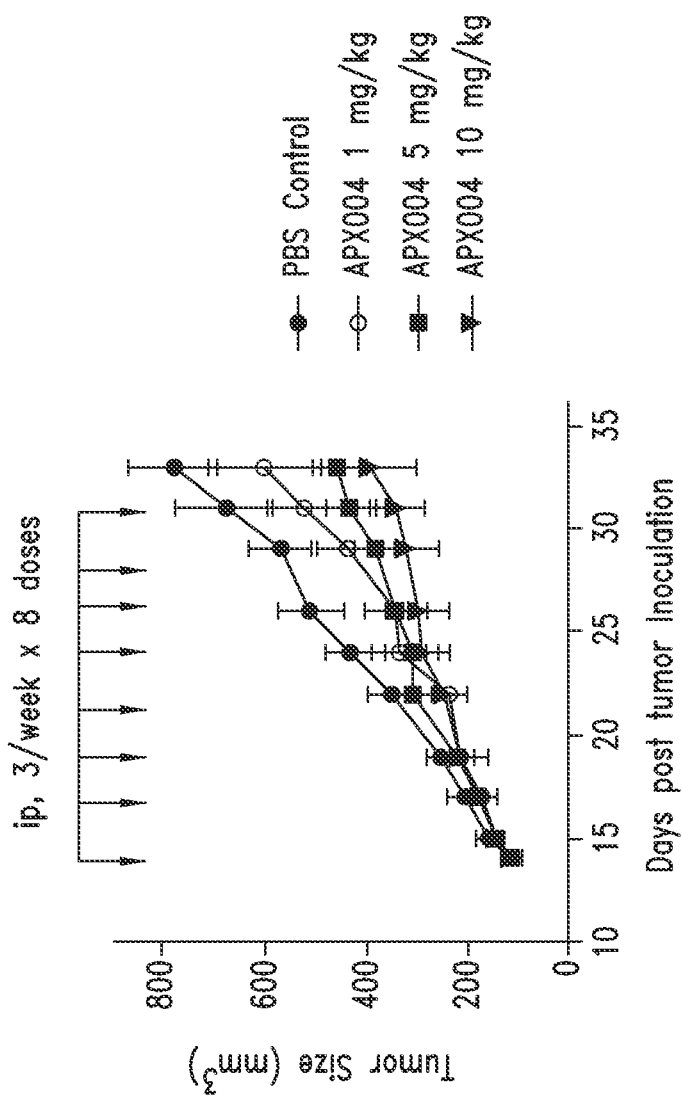
FIG. 10: APX004 significantly inhibits HT29 tumor growth at 5 mg/kg and 10 mg/kg. Tumor volumes were calculated according to the following equation: Volume=(width)$^2$ x length/2. Symbols and bars, mean+standard deviation.

To determine the dose and efficacy relationship of APX004 in the human colorectal cancer HT29 xenograft model, human colorectal cancer xenografts were established by subcutaneous inoculation of human HT29 cells into the dorsal flanks of female BALB/c nude mice. When tumors reached an average volume of 100 mm3, the tumor bearing mice were randomized into 4 treatment groups as indicated. Various doses of APX004 were administered intraperitoneally 3 times/week for 3 weeks. Tumor size was measured every 3 days. Perpendicular dimensions of the tumor were measured using a Vernier scale caliper. Tumor volumes were calculated according to the following equation: Volume= (width)$^2$×length/2. Symbols and bars, mean+standard deviation. As shown in FIG. 10, APX004 significantly inhibits HT29 tumor growth at 5 mg/kg and 10 mg/kg. A dose-dependent anti-tumor activity of APX004 was observed in this tumor model.

In summary, as shown in the above Examples, APX004 is a humanized IgG1 antibody with high KDR binding affinity which potently inhibits angiogenesis. During the humanization process, both the frameworks and the CDRs were humanized to maximally reduce potential immunogenicity.

APX004 is a neutralizing antibody that blocks the binding of KDR to its ligands and inhibits VEGF-induced KDR phosphorylation and endothelial cell proliferation. Because APX004 cross reacts with mouse KDR, it was possible to evaluate APX004 directly in in vivo mouse models of human tumor xenografts without the need to generate a surrogate antibody. APX004 inhibited the tumor-induced microvasculature formation and tumor growth in multiple human tumor xenografts with anti-tumor effect similar to Avastin®. APX004 seems to be more potent than the ramucirumab's surrogate DC-101 in in vivo tumor models, where a much higher dose of DC-101 (>40 mg) was required to inhibit tumor growth. In contrast to TKIs, APX004 is a more specific KDR targeting agent (does not inhibit other VEGF receptors). As such, it is expected the APX004 will have fewer off target side effects.

In contrast to Avastin®, which binds only one of the VEGF family ligands (VEGF-A only), APX004 potentially blocks all known VEGFs from binding to KDR. This may have a more profound inhibitory effect on tumor angiogenesis than just blocking VEGF-A, and may also be able to contribute to reverse Avastin® resistance caused by ligand redundancy. Thus, APX004 has the potential to improve the treatment of patients with tumors that produce abundant VEGF family ligands in the tumor environment and may overcome resistance to anti-VEGF therapy.

Furthermore, two thirds of the tumor models used in the above studies (A375 and HT-27) express KDR and may use the VEGF-KDR pathway as an autocrine loop to grow. Thus, the anti-tumor effect mediated by the antibodies described herein may include at least 2 modes of action (i) anti-angiogenesis and (ii) direct inhibition of tumor growth (46, 47).

REFERENCES

1. Plate, K. H., Breier, G., and Risau, W. Molecular mechanisms of developmental and tumor angiogenesis. Brain Pathol., 4: 207-218,1994.
2. Hanahan, D., and Folkman, J. Patterns and emerging mechanisms of the angiogenic switch during tumorigenesis. Cell, 86: 353-64,1996.
3. Folkman, J., and Siegel, Y. Angiogenesis. J. Bio. Chem., 267.10931-10934, 1992.
4. Nagy, J. A., Brown, L. F., Senger, D. R., Lanir, N., Van de Water, L., Dvorak, A. M., and Dvorak, H. F. Pathogenesis of tumor stroma generation: a critical role for leaky blood vessels and fibrin deposition. Biochim. Biophys. Acta. 948: 305-326, 1989.
5. Klagsbrun, M., and D'Amore, P. A. Regulators of angiogenesis. Annun. Rev. Physiol., 53: 217-239, 1991.
6. Dvorak, H. F., Nagy, J. A., Feng, D., Brown, L. F., and Dvorak, A. M. Vascular permeability factor/vascular endothelial growth factor and the significance of microvascular hyperpermeability in angiogenesis. Curr. Top. Microbiol. Immunol., 237:97-132, 1999.
Neufeld, G., Cohen, T., Gengrinovitch, S., and Poltorak, Z. Vascular endothelial growth factor (VEGF) and its receptors. FASEB J., 13: 9-22, 1999.
8. Klagsbrun, M., and D'Amore, P. A. Vascular endothelial growth factor and its receptors. Cytokine Growth Factor Rev., 7: 259-270, 1996.
9. Ferrara, N., Heinsohn, H., Walder, C. E., Bunting, S., and Thomas, G. R. The regulation of blood vessel growth by vascular endothelial growth factor. Ann. NY Acad. Sci., 752: 246-256, 1995. Ziebold J L, Hixon J, Boyd A, et al. Differential effects of CD40 stimulation on normal and neoplastic cell growth. Arch Immunol Ther Exp (Warsz) 2000; 48: 225-33.
10. Senger, D. R., Perruzzi, C. A., Feder, J., and Dvorak, H. F. A highly conserved vascular permeability factor secreted by a variety of human and rodent tumor cell lines. Cancer Res., 46: 5629-5632, 1986.
11. Leung, D. W., Cachianes, G., Kuang, W. J., Goeddel, D. V., and Ferrara, N. Vascular endothelial growth factor is a secreted angiogenic mitogen. Science (Washington D.C.), 246: 1306-1309, 1989.van Kooten C, Banchereau J. CD40-CD40 ligand. J Leukoc Biol 2000; 67(1):2-17.
12. Plate, K. H., Breier, G., Weich, H. A., and Risau, W. Vascular endothelial growth factor is a potential tumor angiogenesis factor in human gliomas in vivo. Nature (Lond.), 359: 8435-8438, 1992.
13. Peters, K. G., De Vries, C., and Williams, L. T. Vascular endothelial growth factor receptor expression during embryogenesis and tissue repair suggests a role in endothelial differentiation and blood vessel growth. Proc. Natl. Acad. Sci. USA, 90: 8915-8919, 1993.

14. Fong, G. H., Rossant, J., Gertsenstein, M., and Breitman, M. L. Role of the Flt-1 receptor tyrosine kinase in regulating the assembly of vascular endothelium. Nature (Lond.), 376: 66-70, 1995.
15. Matthews, W., Jordan, C. T., Gavin, M., Jenkins, N. A., Copeland, N. G., and Lemischka, I. R. A receptor tyrosine kinase cDNA isolated from a population of enriched primitive hematopoietic cells and exhibiting close genetic linkage to c-kit. Proc. Natl. Acad. Sci. USA, 88: 9026-9030, 1991.
16. Terman, B. I., Dougher-Vermazen, M., Carrion, M. E., Dimitrov, D., Armellino, D. C., Gospodarowicz, D., and Bohlen, P. Identification of the KDR tyrosine kinase as a receptor for vascular endothelial cell growth factor. Biochem. Biophys. Res. Commun., 187: 1579-1586, 1992.
17. Ferrara, N., Carver-Moore, K., Chen, H., Dowd, M., Lu, L., O'Shea, K. S., Powell-Braxton, L., Hillan, K. J., and Moore, M. W. Heterozygous embryonic lethality induced by targeted inactivation of the VEGF gene. Nature (Lond.), 380: 439-442, 1996.
18. Shalaby, F., Rossant, J., Yamaguchi, T. P., Gersenstein, M., Wu, X.-F., Breitman, M. L., and Schuh, A. C. Failure of blood-island formation and vasculogenesis in Flk-1 deficient mice. Nature (Lond.), 376: 62-66, 1995.
19. Dvorak, H. F., Soiussat, T. M., Brown, L. F., Berse, B., Nagy, J. A., Sotrel, A., Manseau, E. J., Van de Water, L., and Senger, D. R. Distribution of vascular permeability factor (vascular endothelial growth factor) in tumors: concentration in tumor blood vessels. J. Exp. Med., 174: 1275-1278, 1991.
20. Shweiki, D., Itin, A., Soffer, D., and Keshet, E. Vascular endothelial growth factor induced by hypoxia may mediate hypoxia-initiated angiogenesis. Nature (Lond.), 359: 843-845, 1992.
21. O'Brien, T., Cranston, D., Fuggle, S., Bicknell, R., and Harris, A. L. Different angiogenic pathways characterize superficial and invasive bladder cancer. Cancer Res., 55: 510-513, 1995.
22. Brown, L. F., Berse, B., Jackman, R. W., Tognazzi, K., Guidi, A. J., Dvorak, H. F., Senger, D. R., Connolly, J. L., and Schnitt, S. J. Expression of vascular permeability factor (vascular endothelial growth factor) and its receptors in breast cancer. Hum. Pathol., 6: 86-91, 1995.
23. Yoshiji, H., Gomez, D. E., Shibuya, M., and Thorgeirsson, U. P. Expression of vascular endothelial growth factor, its receptor, and other angiogenic factors in human breast cancer. Cancer Res., 56: 2013-2016, 1996.
24. Takahashi, Y., Kitadai, Y., Bucana, C. D., Cleary, K. R., and Ellis, L. M. Expression of vascular endothelial growth factor and its receptor, KDR, correlates with vascularity, metastasis, and proliferation of human colon cancer. Cancer Res., 55: 3964-8968, 1995.
25. Ellis, L. M., Staley, C. A., Liu, W., Fleming, R. Y., Parikh, N. U., Bucana, C. D., and Gallick, G. E. Down-regulation of vascular endothelial growth factor in a human colon carcinoma cell line transfected with an antisense expression vector specific for c-src. J. Biol. Chem., 273: 1052-1057, 1998.
26. Brown, L. F., Berse, B., Jackman, R. W., Tognazzi, K., Manseau, E. J., Senger, D. R., and Dvorak, H. F. Expression of vascular permeability factor (vascular endothelial growth factor) and its receptors in adenocarcinomas of the gastrointestinal tract. Cancer Res., 53: 4727-4735, 1993.
27. Plate, K. H., Breier, G., Weich, H. A., Mennel, H. D., and Risau, W. Vascular endothelial growth factor and glioma angiogenesis: coordinate induction of VEGF receptors, distribution of VEGF protein and possible in vivo regulatory mechanisms. Int. J. Cancer, 59: 520-529, 1994.
28. Stitt, A. W., Simpson, D. A., Boocock, C., Gardiner, T. A., Murphy, G. M., and Archer, D. B. Expression of vascular endothelial growth factor (VEGF) and its receptors is regulated in eyes with intra-ocular tumours. J. Pathol., 186: 306-312, 1998.
29. Rossler, J., Breit, S., Havers, W., and Schweigerer, L. Vascular endothelial growth factor expression in human neuroblastoma: up-regulation by hypoxia. Int. J. Cancer, 81: 113-117, 1999.
30. Millauer, B., Shawver, L. K., Plate, K. H., Risau, W., and Ullrich, A. Glioblastoma growth inhibited in vivo by a dominant-negative Flk-1 mutant. Nature (Lond.), 367: 576-579, 1994.
31. Im, S. A., Gomez-Manzano, C., Fueyo, J., Liu, T. J., Ke, L. D., Kim, J. S., Lee, H. Y., Steck, P. A., Kyritsis, A. P., and Yung, W. K. Anti-angiogenesis treatment for gliomas: transfer of antisense-vascular endothelial growth factor inhibits tumor growth in vivo. Cancer Res., 59: 895-900, 1999.
32. Kendell, R. L., and Thomas, K. A. Inhibition of vascular endothelial growth factor activity by endogenously encoded soluble receptor. Proc. Natl. Acad. Sci. USA, 90: 10705-10709, 1993.
33. Ferrara N, Hillan K J, Gerber H P, Novotny W. Discovery and development of bevacizumab, an anti-VEGF antibody for treating cancer. Nat Rev Drug Discov 2004; 3(5):391-400.
34. Avery R L, Pieramici D J, Rabena M D, et al. Intravitreal bevacizumab (Avastin) for neovascular age-related macular degeneration. Ophthalmology 2006; 113(3):363-72.
35. Lin, P. Sankar, S., Shan, S., Dewhirst, M. W., Polverini, P. J., Quinn, T. Q., and Peters, K. G. Inhibition of tumor growth by targeting tumor endothelium using a soluble vascular endothelial growth factor receptor. Cell Growth Differ., 9: 49-58, 1998.
36. Fong, T. A., Shawver, L. K., Sun, L., Tang, C., App, H., Powell, T. J., Kim, Y. H., Schreck, R., Wang, X., Risau, W., Ullrich, A., Hirth, K. P., and McMahon, G. SU5416 is a potent and selective inhibitor of the vascular endothelial growth factor anti-VEGF receptor antibody inhibits tumor growth receptor (Flk-1/KDR) that inhibits tyrosine kinase catalysis, tumor vascularization, and growth of multiple tumor types. Cancer Res., 59: 99-106, 1999.
37. Seetharam, L. et al. A unique signal transduction from FLT tyrosine kinase, a receptor for vascular endothelial growth factor VEGF. Oncogene 10, 135-147 (1995).
38. Waltenberger, J., Claesson-Welsh, L., Siegbahn, A., Shibuya, M. & Heldin, C. H. Different signal transduction properties of KDR and Flt1, two receptors for vascular endothelial growth factor. J. Biol. Chem. 269, 26988-26995 (1994).
39. Garcia J A, Nudes G R, Choueiri T K, Stadler W M, Wood L S, Bhatia S, et al. Phase II study of IMC-1121B in patients with metastatic renal cancer (mRCC) following VEGFR-2 tyrosine kinase inhibitor (TKI) therapy (IMCL CP12-0605/NCT00515697). Am Soc Clin Oncol annual meeting 2010:326
40. Kendrew J, Eberlein C, Hedberg B, McDaid K, Smith N R, Weir H M, Wedge S R, Blakey D C, Foltz I N, Zhou J, Kang J S, Barry S T. An antibody targetted to VEGFR-2 Ig domains 4-7 inhibits VEGFR-2 activation and VEGFR-2 dependent angiogenesis without affecting ligand binding. Mol Cancer Ther. 2011 Mar. 9.

41. Shalaby, F. et al. Failure of blood-island formation and vasculogenesis in Flk-1-deficient mice. Nature 376, 62-66 (1995).
42. Boocock C A, Charnock-Jones D S, Sharkey A M, McLaren J, Barker P J, Wright K A, Twentyman P R, Smith S K. Expression of vascular endothelial growth factor and its receptors flt and KDR in ovarian carcinoma. J Natl Cancer Inst. 1995 Apr. 5; 87(7):506-16.
43. Zhu Z, Hattori K, Zhang H, Jimenez X, Ludwig D L, Dias S, Kussie P, Koo H, Kim H J, Lu D, Liu M, Tejada R, Friedrich M, Bohlen P, Witte L, Rafii S. Inhibition of human leukemia in an animal model with human antibodies directed against vascular endothelial growth factor receptor 2. Correlation between antibody affinity and biological activity. Leukemia. 2003 March; 17(3):604-11.
44. Witte L, Hicklin D J, Zhu Z, Pytowski B, Kotanides H, Rockwell P, Böhlen P. Monoclonal antibodies targeting the VEGF receptor-2 (Flk1/KDR) as an anti-angiogenic therapeutic strategy. Cancer Metastasis Rev. 1998 June; 17(2):155-61.
45. Yoo et al. Human monoclonal antibody neutralizing vascular endothelial growth factor and use thereof. US patent application publication No.: US 2011/0065176 A1
46. Liu B, et al., Melanoma cell lines express VEGF receptor KDR and respond to exogenously added VEGF. Biochem Biophys Res Commun 1995 217:721-727.
47. Nguyen Q D, et al., inhibition of vascular endothelial growth factor (VEGF)-165 and semaphorin 3A-mediated cellular invasion in tumor growth by the VEGF signaling inhibitor AD 4190 in human: cancer cells and xenografts. Mol Cancer Ther. N006 5:2070-2077.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or an antigen-binding fragment thereof, that binds to KDR, comprising (i) a heavy chain variable region comprising the VHCDR1 region set forth in SEQ ID NO:3 or 11, the VHCDR2 region set forth in SEQ ID NO:4 or 12, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO: 8.

2. The isolated antibody, or antigen-binding fragment thereof, of claim 1 wherein the heavy chain variable region comprises the amino acid sequence set forth in SEQ ID NO:1.

3. The isolated antibody, or antigen-binding fragment thereof, of claim 1 wherein the light chain variable region comprises the amino acid sequence set forth in SEQ ID NO:2.

4. An isolated antibody, or an antigen-binding fragment thereof, that binds to KDR, comprising (i) a heavy chain variable region comprising a VHCDR1, a VHCDR2, and a VHCDR3 as set forth in any one of SEQ ID NOs:69, 96, 123; SEQ ID NOs:70, 97, 124; SEQ ID NOs:71, 98, 125; SEQ ID NOs:72, 99, 126; SEQ ID NOs:73, 100, 127; SEQ ID NOs:74, 101, 128; SEQ ID NOs:75, 102, 129; SEQ ID NOs:76, 103, 130; SEQ ID NOs:77, 104, 131; SEQ ID NOs:78, 105, 132; SEQ ID NOs:79, 106, 133; SEQ ID NOs:80, 107, 134; SEQ ID NOs:82, 109, 136; SEQ ID NOs:83, 110, 137; SEQ ID NOs:84, 111, 138; SEQ ID NOs:85, 112, 139; SEQ ID NOs:86, 113, 140; SEQ ID NOs:87, 114, 141; SEQ ID NOs:88, 115, 142; SEQ ID NOs:89, 116, 143; SEQ ID NOs:90, 117, 144; SEQ ID NOs:91, 118, 145; SEQ ID NOs:92, 119, 146; SEQ ID NOs:93, 120, 147; SEQ ID NOs:94, 121, 148; and SEQ ID NOs:95, 122, 149, respectively; and (ii) a corresponding light chain variable region comprising a VLCDR1, a VLCDR2 and a VLCDR3 as set forth in any one of SEQ ID NOs:150, 177, 204; SEQ ID NOs:151, 178, 205; SEQ ID NOs:152, 179, 206; SEQ ID NOs:153, 180, 207; SEQ ID NOs:154, 181, 208; SEQ ID NOs:155, 182, 209; SEQ ID NOs:156, 183, 210; SEQ ID NOs:157, 184, 211; SEQ ID NOs:158, 185, 212; SEQ ID NOs:159, 186, 213; SEQ ID NOs:160, 187, 214; SEQ ID NOs:161, 188, 215; SEQ ID NOs:163, 190, 217; SEQ ID NOs:164, 191, 218; SEQ ID NOs:165, 192, 219; SEQ ID NOs:166, 193, 220; SEQ ID NOs:167, 194, 221; SEQ ID NOs:168, 195, 222; SEQ ID NOs:169, 196, 223; SEQ ID NOs:170, 197, 224; SEQ ID NOs:171, 198, 225; SEQ ID NOs:172, 199, 226; SEQ ID NOs:173, 200, 227; SEQ ID NOs:174, 201, 228; SEQ ID NOs:175, 202, 229; and SEQ ID NOs:176, 203, 230, respectively.

5. An isolated antibody, or an antigen-binding fragment thereof, that binds to KDR, comprising a heavy chain variable region comprising the amino acid sequence set forth in SEQ ID NO:1 and a light chain variable region which comprises an amino acid sequence having at least 90% identity to the amino acid sequence set forth in SEQ ID NO:2.

6. The isolated antibody, or an antigen-binding fragment thereof, of claim 5 comprising a light chain variable region which comprises the amino acid sequence set forth in SEQ ID NO:2.

7. An isolated antibody, or an antigen-binding fragment thereof, that binds to KDR, comprising a light chain variable region comprising the amino acid sequence set forth in SEQ ID NO:2 and a heavy chain variable region which comprises an amino acid sequence having at least 90% identity to the amino acid sequence set forth in SEQ ID NO:1.

8. The isolated antibody of claim 1, wherein the antibody is humanized.

9. The isolated antibody of claim 8, wherein the VH region comprises the amino acid sequence set forth in SEQ ID NO:9 and the VL region comprises the amino acid sequence set forth in SEQ ID NO:10.

10. The isolated antibody of claim 1 wherein the antibody is selected from the group consisting of a single chain antibody, a ScFv, a univalent antibody lacking a hinge region, and a minibody.

11. The isolated antibody of claim 1 wherein the antibody is a Fab fragment, a Fab' fragment, a F(ab')$_2$ fragment, or a whole antibody.

12. The isolated antibody, or antigen-binding fragment thereof, of claim 9 that binds KDR with a $K_D$ of $5.3 \times 10^{-11}$ M or lower.

13. The isolated antibody, or antigen-binding fragment thereof, of claim 12 wherein the isolated antibody, or antigen-binding fragment thereof:
 a. blocks VEGF binding to KDR;
 b. inhibits KDR signaling;
 c. inhibits endothelial cell proliferation;
 d. inhibits tumor angiogenesis;
 e. inhibits tumor cell growth;
 f. a combination of any one or more of a.-e.

14. The isolated antibody, or antigen-binding fragment thereof, of claim 1 that directly inhibits tumor growth.

15. The isolated antibody of claim 1, wherein the antibody cross-reacts with murine KDR or monkey KDR.

16. A composition comprising a physiologically acceptable carrier and a therapeutically effective amount of the isolated antibody or antigen-binding fragment thereof according to claim 1.

17. The isolated antibody of claim 1 comprising a human IgG constant domain.

18. The isolated antibody of claim 17, wherein the IgG constant domain comprises an IgG1 CH1 domain.

19. The isolated antibody of claim 17, wherein the IgG constant domain comprises an IgG1 Fc region.

20. The composition of claim 16, wherein the isolated antibody, or antigen-binding fragment thereof, comprises the VH region set forth in SEQ ID NO:9 and the VL region set forth in SEQ ID NO:10.

* * * * *

SEQUENCE LISTING

```
<160> NUMBER OF SEQ ID NOS: 233

<210> SEQ ID NO 1
<211> LENGTH: 140
<212> TYPE: PRT
<213> ORGANISM: Oryctolagus cuniculus

<400> SEQUENCE: 1

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Asn
        35                  40                  45

Asn Tyr Ala Met Ser Trp Val Arg Gln Ala Pro Gly Lys Gly Leu Glu
    50                  55                  60

Trp Ile Gly Ile Ile Gly Ser Ser Gly Ser Ile Phe Tyr Ala Ser Trp
65                  70                  75                  80

Ala Lys Gly Arg Ile Thr Ile Ser Lys Thr Ser Thr Thr Val Asp Leu
                85                  90                  95

Lys Phe Thr Ser Leu Thr Thr Glu Asp Thr Ala Thr Tyr Phe Cys Ala
            100                 105                 110

Arg Val Leu Trp Ala Gly Ser Val Ala Tyr Ala Tyr His Asn Ile Trp
        115                 120                 125

Gly Pro Gly Thr Leu Val Thr Val Ser Ser Gly Gln
    130                 135                 140

<210> SEQ ID NO 2
<211> LENGTH: 132
<212> TYPE: PRT
<213> ORGANISM: Oryctolagus cuniculus

<400> SEQUENCE: 2

Met Asp Thr Arg Ala Pro Thr Gln Leu Leu Gly Leu Leu Leu Leu Trp
1               5                   10                  15
```

```
Leu Pro Gly Val Ile Cys Asp Pro Val Met Thr Gln Thr Pro Ala Ser
            20                  25                  30

Val Ser Glu Pro Val Gly Gly Thr Val Thr Ile Asn Cys Gln Ala Ser
            35                  40                  45

Glu Glu Leu Gly Ser Asn Leu Ala Trp Tyr Gln Gln Lys Pro Gly Gln
 50                  55                  60

Pro Pro Lys Leu Leu Ile Tyr Ser Ala Ser Thr Leu Ala Ser Gly Val
 65                  70                  75                  80

Pro Ser Arg Phe Lys Gly Ser Gly Ser Gly Thr Glu Tyr Thr Leu Thr
                 85                  90                  95

Ile Ser Asp Leu Glu Cys Ala Asp Ala Ala Thr Tyr Tyr Cys Gln Tyr
            100                 105                 110

Thr Tyr Phe Gly Ser Ser Tyr Leu Gly Ala Phe Gly Gly Gly Thr Glu
            115                 120                 125

Val Val Val Lys
            130

<210> SEQ ID NO 3
<211> LENGTH: 5
<212> TYPE: PRT
<213> ORGANISM: Oryctolagus cuniculus

<400> SEQUENCE: 3

Asn Tyr Ala Met Ser
1               5

<210> SEQ ID NO 4
<211> LENGTH: 16
<212> TYPE: PRT
<213> ORGANISM: Oryctolagus cuniculus

<400> SEQUENCE: 4

Ile Ile Gly Ser Ser Gly Ser Ile Phe Tyr Ala Ser Trp Ala Lys Gly
1               5                   10                  15

<210> SEQ ID NO 5
<211> LENGTH: 14
<212> TYPE: PRT
<213> ORGANISM: Oryctolagus cuniculus

<400> SEQUENCE: 5

Val Leu Trp Ala Gly Ser Val Ala Tyr Ala Tyr His Asn Ile
1               5                   10

<210> SEQ ID NO 6
<211> LENGTH: 11
<212> TYPE: PRT
<213> ORGANISM: Oryctolagus cuniculus

<400> SEQUENCE: 6

Gln Ala Ser Glu Glu Leu Gly Ser Asn Leu Ala
1               5                   10

<210> SEQ ID NO 7
<211> LENGTH: 7
<212> TYPE: PRT
<213> ORGANISM: Oryctolagus cuniculus

<400> SEQUENCE: 7

Ser Ala Ser Thr Leu Ala Ser
1               5
```

<210> SEQ ID NO 8
<211> LENGTH: 12
<212> TYPE: PRT
<213> ORGANISM: Oryctolagus cuniculus

<400> SEQUENCE: 8

Gln Tyr Thr Tyr Phe Gly Ser Ser Tyr Leu Gly Ala
1               5                   10

<210> SEQ ID NO 9
<211> LENGTH: 122
<212> TYPE: PRT
<213> ORGANISM: Artificial Sequence
<220> FEATURE:
<223> OTHER INFORMATION: Humanized sequence of the VH region of the
      clone 36 rabbit anti-KDR antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Ser Ser Tyr
            20                  25                  30

Ala Met Ser Trp Val Arg Gln Ala Pro Gly Lys Gly Leu Glu Trp Val
        35                  40                  45

Gly Ile Ile Gly Ser Gly Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Val Leu Trp Ala Gly Ser Val Ala Tyr Ala Tyr His Asn Ile Trp
            100                 105                 110

Gly Pro Gly Thr Leu Val Thr Val Ser Ser
        115                 120

<210> SEQ ID NO 10
<211> LENGTH: 110
<212> TYPE: PRT
<213> ORGANISM: Artificial Sequence
<220> FEATURE:
<223> OTHER INFORMATION: Humanized sequence of the VL region of the
      clone 36 rabbit anti-KDR antibody

<400> SEQUENCE: 10

Asp Ile Gln Met Thr Gln Ser Pro Ser Ser Leu Ser Ala Ser Val Gly
1               5                   10                  15

Asp Arg Val Thr Ile Asn Cys Gln Ala Ser Glu Glu Leu Gly Ser Asn
            20                  25                  30

Leu Ala Trp Tyr Gln Gln Lys Pro Gly Lys Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Tyr Thr Tyr Phe Gly Ser Ser
                85                  90                  95

Tyr Leu Gly Ala Phe Gly Gly Gly Thr Lys Val Glu Ile Lys
            100                 105                 110

<210> SEQ ID NO 11
<211> LENGTH: 5
<212> TYPE: PRT
<213> ORGANISM: Artificial Sequence
<220> FEATURE:
<223> OTHER INFORMATION: VHCDR1 region of the humanized clone 36
      anti-KDR antibody

<400> SEQUENCE: 11

Ser Tyr Ala Met Ser
1               5

<210> SEQ ID NO 12
<211> LENGTH: 16
<212> TYPE: PRT
<213> ORGANISM: Artificial Sequence
<220> FEATURE:
<223> OTHER INFORMATION: VHCDR2 region of the humanized clone 36
      anti-KDR antibody

<400> SEQUENCE: 12

Ile Ile Gly Ser Gly Gly Ser Thr Tyr Tyr Ala Ser Trp Ala Lys Gly
1               5                   10                  15

<210> SEQ ID NO 13
<211> LENGTH: 324
<212> TYPE: DNA
<213> ORGANISM: Homo sapiens

<400> SEQUENCE: 13
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct caatcgggt aactcccagg agagtgtcac agagcaggac      180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324

<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15

```
<211> LENGTH: 993
<212> TYPE: DNA
<213> ORGANISM: Homo sapiens

<400> SEQUENCE: 15
gctagcacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa taa                                 993

<210> SEQ ID NO 16
<211> LENGTH: 330
<212> TYPE: PRT
<213> ORGANISM: Homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
            165                 170                 175
Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 140
<212> TYPE: PRT
<213> ORGANISM: Oryctolagus cuniculus

<400> SEQUENCE: 17

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Asn Tyr Ala Met Ser Trp Phe Arg Gln Ala Pro Gly Lys Gly Leu Glu
    50                  55                  60

Trp Ile Gly Leu Ile Arg Ser Ser Gly Ala Thr Tyr Tyr Ala Ser Trp
65                  70                  75                  80

Ala Lys Gly Arg Phe Thr Ile Ser Lys Ala Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125

Gly Pro Gly Ser Leu Val Thr Val Ser Ser Gly Gln
    130                 135                 140

<210> SEQ ID NO 18
<211> LENGTH: 137
<212> TYPE: PRT
<213> ORGANISM: Oryctolagus cuniculus

<400> SEQUENCE: 18

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
```

```
                    20                  25                  30
Gly Thr Pro Leu Thr Leu Thr Cys Thr Val Ser Gly Ile Asp Leu Ser
            35                  40                  45

Ser Tyr Ala Met Gly Trp Val Arg Gln Ala Pro Gly Lys Gly Leu Glu
        50                  55                  60

His Ile Gly Ile Ile Thr Ala Ser Gly Gly Ile Tyr Ala Ser Trp
 65                  70                  75                  80

Ala Lys Gly Arg Phe Thr Ile Ser Lys Thr Ser Thr Val Asp Leu
                85                  90                  95

Arg Ile Pro Ser Pro Thr Thr Glu Asp Thr Gly Thr Tyr Phe Cys Ala
            100                 105                 110

Arg Thr Glu Asn Ser Tyr Phe Leu Tyr Phe Thr Ile Trp Gly Pro Gly
        115                 120                 125

Thr Leu Val Thr Val Ser Ser Gly Gln
        130                 135
```

<210> SEQ ID NO 19
<211> LENGTH: 140
<212> TYPE: PRT
<213> ORGANISM: Oryctolagus cuniculus

<400> SEQUENCE: 19

```
Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Ile Asp Leu Asn
            35                  40                  45

Ser Tyr Ala Met Ser Trp Phe Arg Gln Ala Pro Gly Lys Gly Leu Glu
        50                  55                  60

Trp Ile Gly Leu Ile Arg Arg Ser Gly Ala Thr Tyr Tyr Ala Ser Trp
 65                  70                  75                  80

Ala Lys Gly Arg Phe Thr Ile Ser Lys Ala Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125

Gly Pro Gly Thr Leu Val Thr Val Ser Ser Gly Gln
 130                 135                 140
```

<210> SEQ ID NO 20
<211> LENGTH: 142
<212> TYPE: PRT
<213> ORGANISM: Oryctolagus cuniculus

<400> SEQUENCE: 20

```
Met Glu Thr Gly Leu Arg Trp Leu Leu Leu Val Ala Val Leu Lys Gly
 1               5                  10                  15

Val Gln Cys Glu Glu Gln Leu Lys Glu Ser Gly Gly Asp Leu Val Lys
                20                  25                  30

Pro Glu Gly Ser Leu Thr Leu Thr Cys Lys Ala Ser Gly Phe Asp Leu
            35                  40                  45

Ser Ser Glu Phe Tyr Ile Cys Trp Val Arg Gln Ala Pro Gly Lys Gly
        50                  55                  60

Leu Glu Trp Ile Gly Cys Ile Ala Thr Val Ser Ser Arg Arg Leu Tyr
```

```
                65                  70                  75                  80
Ala Ser Trp Val Asn Gly Arg Phe Thr Ile Ser Lys Thr Ser Ser Thr
                    85                  90                  95

Thr Val Thr Leu Gln Met Pro Ser Leu Thr Ala Ala Asp Thr Ala Thr
                    100                 105                 110

Tyr Phe Cys Ala Arg Asp Asp Ser Ala Arg Asn Trp Phe Tyr Phe Tyr
                    115                 120                 125

Leu Trp Gly Pro Gly Thr Leu Val Thr Val Ser Ser Gly Gln
                    130                 135                 140

<210> SEQ ID NO 21
<211> LENGTH: 140
<212> TYPE: PRT
<213> ORGANISM: Oryctolagus cuniculus

<400> SEQUENCE: 21

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                    20                  25                  30

Gly Thr Pro Leu Thr Leu Thr Cys Thr Val Ser Gly Phe Ser Leu Ser
                    35                  40                  45

Asp Tyr Ala Met Ser Trp Val Arg Gln Ala Pro Gly Lys Gly Leu Glu
                    50                  55                  60

Trp Ile Gly Met Val Arg Asp Thr Gly Val Thr Phe Tyr Ala Gly Trp
65                  70                  75                  80

Ala Lys Gly Arg Phe Thr Ile Ser Lys Thr Ser Thr Thr Val Asp Leu
                    85                  90                  95

Lys Phe Thr Ser Pro Thr Thr Glu Asp Thr Ala Thr Tyr Phe Cys Ala
                    100                 105                 110

Arg Val Leu Trp Ala Gly Tyr Val Ala Tyr Ala Tyr His Asn Ile Trp
                    115                 120                 125

Gly Pro Gly Thr Leu Val Thr Val Ser Ser Gly Gln
                    130                 135                 140

<210> SEQ ID NO 22
<211> LENGTH: 139
<212> TYPE: PRT
<213> ORGANISM: Oryctolagus cuniculus

<400> SEQUENCE: 22

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
                    20                  25                  30

Gly Thr Ser Leu Thr Leu Thr Cys Thr Ala Ser Gly Phe Ser Phe Ser
                    35                  40                  45

Ala Arg His Phe Met Tyr Trp Val Arg Gln Ala Pro Gly Lys Gly Leu
                    50                  55                  60

Glu Trp Ile Gly Cys Ile Asp Ile Gly Ser Gly Ser Thr Tyr Tyr Thr
65                  70                  75                  80

Ser Trp Ala Lys Asp Arg Phe Thr Ile Ser Lys Pro Ser Ser Thr Thr
                    85                  90                  95

Val Thr Leu Gln Met Thr Ser Leu Thr Ala Ala Asp Thr Ala Thr Tyr
                    100                 105                 110

Phe Cys Ala Arg Ser Ser Gly Tyr Pro Tyr Tyr Phe Thr Leu Trp Gly
```

```
                    115                 120                 125

Pro Gly Thr Leu Val Thr Val Ser Ser Gly Gln
        130                 135

<210> SEQ ID NO 23
<211> LENGTH: 131
<212> TYPE: PRT
<213> ORGANISM: Oryctolagus cuniculus

<400> SEQUENCE: 23

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asn Ala Met Ala Trp Val Arg Gln Ala Pro Gly Lys Gly Leu Glu
    50                  55                  60

Trp Ile Gly Ile Ile Asp Gly Asp Val Ser Pro Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Ala Arg Pro Phe Asn Ile Trp Gly Pro Gly Thr Leu Val Thr Val Ser
        115                 120                 125

Ser Gly Gln
    130

<210> SEQ ID NO 24
<211> LENGTH: 140
<212> TYPE: PRT
<213> ORGANISM: Oryctolagus cuniculus

<400> SEQUENCE: 24

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Gly Ser Thr Tyr Tyr Ala Thr Trp
65                  70                  75                  80

Val Lys Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Gly Asp Asp Asp Val Ser Asp Tyr Phe Tyr Tyr Phe Pro Ile Trp
        115                 120                 125

Gly Pro Gly Thr Leu Val Thr Val Ser Ser Gly Gln
    130                 135                 140

<210> SEQ ID NO 25
<211> LENGTH: 140
<212> TYPE: PRT
```

<213> ORGANISM: Oryctolagus cuniculus

<400> SEQUENCE: 25

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Gly Ser Thr Tyr Tyr Ala Thr Trp
65                  70                  75                  80

Val Lys Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Gly Asp Asp Asp Val Ser Asp Tyr Phe Tyr Tyr Phe Pro Ile Trp
        115                 120                 125

Gly Pro Gly Thr Leu Val Thr Val Ser Ser Gly Gln
    130                 135                 140

<210> SEQ ID NO 26
<211> LENGTH: 137
<212> TYPE: PRT
<213> ORGANISM: Oryctolagus cuniculus

<400> SEQUENCE: 26

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Lys Asn Ala Ile Ser Trp Val Arg Gln Val Pro Gly Glu Gly Leu Glu
    50                  55                  60

Trp Ile Gly Ile Ile Tyr Gly Asp Gly Asn Arg Asp Tyr Ala Asn Trp
65                  70                  75                  80

Ala Lys Gly Arg Phe Thr Ile Ser Lys Thr Ser Thr Thr Val Asp Leu
                85                  90                  95

Lys Val Thr Ser Pro Thr Thr Glu Asp Thr Ala Thr Tyr Phe Cys Ala
            100                 105                 110

Arg Gly Thr Thr Ile Trp Ser Asp Tyr Leu Asp Ile Trp Gly Pro Gly
        115                 120                 125

Thr Leu Val Thr Ile Ser Ser Gly Gln
    130                 135

<210> SEQ ID NO 27
<211> LENGTH: 140
<212> TYPE: PRT
<213> ORGANISM: Oryctolagus cuniculus

<400> SEQUENCE: 27

Met Glu Thr Gly Leu Arg Trp Leu Leu Leu Val Ala Met Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ala Leu Asn
            35                  40                  45

Asp Phe Ala Met Ser Trp Val Arg Gln Ala Pro Gly Lys Gly Leu Glu
        50                  55                  60

Trp Ile Gly Met Ile Ala Ser Ser Gly Asn Thr Phe Tyr Ala Ser Trp
65                  70                  75                  80

Ala Lys Gly Arg Phe Thr Ile Ser Lys Thr Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Tyr Ile Ala Tyr Ala Tyr His Asn Ile Trp
        115                 120                 125

Gly Pro Gly Thr Leu Val Thr Val Ser Ser Gly Gln
    130                 135                 140

<210> SEQ ID NO 28
<211> LENGTH: 140
<212> TYPE: PRT
<213> ORGANISM: Oryctolagus cuniculus

<400> SEQUENCE: 28

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Asn
            35                  40                  45

Asn Tyr Ala Met Ser Trp Phe Arg Gln Ala Pro Gly Lys Gly Leu Glu
        50                  55                  60

Trp Ile Gly Leu Ile Arg Ser Ser Gly Ala Thr Tyr Tyr Ala Ser Trp
65                  70                  75                  80

Ala Lys Gly Arg Phe Thr Ile Ser Lys Ala Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125

Gly Pro Gly Thr Leu Val Thr Val Ser Ser Gly Gln
    130                 135                 140

<210> SEQ ID NO 29
<211> LENGTH: 140
<212> TYPE: PRT
<213> ORGANISM: Oryctolagus cuniculus

<400> SEQUENCE: 29

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
            35                  40                  45

Ser Tyr Ala Met Gly Trp Val Arg Gln Ala Pro Gly Lys Gly Leu Glu
        50                  55                  60

Trp Ile Gly Phe Ile Ser Ser Ser Gly Ser Thr Tyr Tyr Ala Ser Trp
65                  70                  75                  80

```
Ala Lys Gly Arg Phe Thr Ile Ser Lys Thr Ser Thr Val Asp Leu
                85                  90                  95

Lys Ile Thr Ser Pro Thr Thr Glu Asp Thr Ala Thr Tyr Phe Cys Ala
            100                 105                 110

Asn Asn Tyr Asp Asp Tyr Gly Asp Phe Leu His Tyr Phe Asn Ile Trp
        115                 120                 125

Gly Pro Gly Thr Leu Val Thr Val Ser Ser Gly Gln
    130                 135                 140

<210> SEQ ID NO 30
<211> LENGTH: 140
<212> TYPE: PRT
<213> ORGANISM: Oryctolagus cuniculus

<400> SEQUENCE: 30

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asp Tyr Ala Met Ser Trp Val Arg Gln Ala Pro Gly Lys Gly Leu Glu
    50                  55                  60

Trp Ile Gly Ile Ile Ser Asn Ser Gly Ile Thr Phe Tyr Ala Gly Trp
65                  70                  75                  80

Ala Lys Gly Arg Phe Thr Ile Ser Lys Thr Ser Thr Val Asp Leu
                85                  90                  95

Lys Phe Thr Ser Pro Thr Thr Glu Asp Thr Ala Thr Tyr Phe Cys Ala
            100                 105                 110

Arg Ala Leu Trp Ala Gly Tyr Ile Ala Tyr Val Tyr His Asn Ile Trp
        115                 120                 125

Gly Pro Gly Thr Leu Val Thr Val Ser Ser Gly Gln
    130                 135                 140

<210> SEQ ID NO 31
<211> LENGTH: 140
<212> TYPE: PRT
<213> ORGANISM: Oryctolagus cuniculus

<400> SEQUENCE: 31

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Ser Trp Phe Arg Gln Ala Pro Gly Lys Gly Leu Glu
    50                  55                  60

Trp Ile Gly Leu Ile Arg Ser Ser Gly Ala Thr Tyr Tyr Ala Ser Trp
65                  70                  75                  80

Ala Lys Gly Arg Phe Thr Ile Ser Lys Ala Ser Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125
```

-continued

Gly Pro Gly Thr Leu Val Thr Val Ser Ser Gly Gln
        130                 135                 140

<210> SEQ ID NO 32
<211> LENGTH: 140
<212> TYPE: PRT
<213> ORGANISM: Oryctolagus cuniculus

<400> SEQUENCE: 32

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Asn Tyr Ala Met Ser Trp Phe Arg Gln Ala Pro Gly Lys Gly Leu Glu
    50                  55                  60

Trp Ile Gly Leu Ile Arg Ser Gly Ala Ala Tyr Asp Ala Pro Trp
65                  70                  75                  80

Ala Lys Gly Arg Phe Thr Ile Ser Lys Ala Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125

Gly Pro Gly Thr Leu Val Thr Val Ser Ser Gly Gln
        130                 135                 140

<210> SEQ ID NO 33
<211> LENGTH: 140
<212> TYPE: PRT
<213> ORGANISM: Oryctolagus cuniculus

<400> SEQUENCE: 33

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Asn Tyr Ala Met Ser Trp Phe Arg Gln Ala Pro Gly Lys Gly Leu Glu
    50                  55                  60

Trp Ile Gly Leu Ile Arg Ser Gly Gly Ala Thr Tyr Ala Ser Trp
65                  70                  75                  80

Ala Lys Gly Arg Phe Thr Ile Ser Lys Val Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125

Gly Pro Gly Thr Leu Val Thr Val Ser Ser Gly Gln
        130                 135                 140

<210> SEQ ID NO 34
<211> LENGTH: 140
<212> TYPE: PRT
<213> ORGANISM: Oryctolagus cuniculus

<400> SEQUENCE: 34

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Tyr Ala Met Ser Trp Val Arg Gln Ala Pro Gly Lys Gly Leu Glu
50                  55                  60

Trp Val Gly Ile Ile Arg Gly Ser Gly Ser Ile Tyr Tyr Ala Asn Trp
65                  70                  75                  80

Ala Lys Gly Arg Phe Thr Ile Ser Lys Thr Ser Thr Thr Val Asp Leu
                85                  90                  95

Arg Phe Ala Ser Pro Thr Thr Glu Asp Thr Ala Thr Tyr Phe Cys Ala
            100                 105                 110

Arg Val Leu Trp Pro Gly Ser Val Ala Tyr Ala Tyr His Asn Ile Trp
        115                 120                 125

Gly Pro Gly Thr Leu Val Thr Val Ser Ser Gly Gln
130                 135                 140

<210> SEQ ID NO 35
<211> LENGTH: 140
<212> TYPE: PRT
<213> ORGANISM: Oryctolagus cuniculus

<400> SEQUENCE: 35

Met Glu Thr Gly Leu Arg Trp Leu Leu Leu Val Ala Val Leu Lys Gly
1               5                   10                  15

Val Arg Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Asn
        35                  40                  45

Asn Tyr Ala Met Ser Trp Phe Arg Gln Ala Pro Gly Lys Gly Leu Glu
50                  55                  60

Trp Ile Gly Leu Ile Arg Ser Ser Gly Ala Thr Tyr Tyr Ala Ser Trp
65                  70                  75                  80

Ala Lys Gly Arg Phe Thr Ile Ser Lys Ala Ser Thr Thr Val Asp Leu
                85                  90                  95

Lys Phe Thr Ser Pro Thr Thr Glu Asp Thr Ala Thr Tyr Phe Cys Ala
            100                 105                 110

Arg Val Leu Trp Pro Gly Asp Ile Ala Tyr Ala Tyr His Asn Ile Trp
        115                 120                 125

Gly Pro Gly Thr Leu Val Thr Val Ser Ala Gly Gln
130                 135                 140

<210> SEQ ID NO 36
<211> LENGTH: 140
<212> TYPE: PRT
<213> ORGANISM: Oryctolagus cuniculus

<400> SEQUENCE: 36

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
            35                  40                  45

Ser Tyr Ala Met Ser Trp Val Arg Gln Ala Pro Gly Lys Gly Leu Glu
 50                  55                  60

Trp Ile Gly Ile Ile Ser Ser Gly Asn Thr Tyr Phe Ala Ser Trp
 65                  70                  75                  80

Ala Lys Gly Arg Phe Thr Ile Ser Lys Thr Ser Thr Val Asp Leu
                85                  90                  95

Lys Phe Thr Ser Pro Thr Thr Glu Asp Thr Ala Thr Tyr Phe Cys Ala
                100                 105                 110

Arg Val Leu Trp Ala Gly Ser Val Ala Tyr Ala Tyr His Asn Ile Trp
                115                 120                 125

Gly Pro Gly Thr Leu Val Thr Val Ser Ser Gly Gln
            130                 135                 140

<210> SEQ ID NO 37
<211> LENGTH: 140
<212> TYPE: PRT
<213> ORGANISM: Oryctolagus cuniculus

<400> SEQUENCE: 37

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Phe Ser Leu Ser
            35                  40                  45

Thr Tyr Ala Met Ser Trp Phe Arg Gln Ala Pro Gly Lys Gly Leu Glu
 50                  55                  60

Trp Ile Gly Leu Ile Arg Ser Ser Gly Ala Thr Tyr Tyr Ala Ser Trp
 65                  70                  75                  80

Ala Lys Gly Arg Phe Thr Ile Ser Lys Ala Ser Thr Thr Val Asp Leu
                85                  90                  95

Lys Phe Thr Ser Pro Thr Thr Glu Asp Thr Ala Thr Tyr Phe Cys Ala
                100                 105                 110

Arg Val Leu Trp Pro Gly Asp Ile Ala Tyr Ala Tyr His Asn Ile Trp
                115                 120                 125

Gly Pro Gly Thr Leu Val Thr Val Ser Ser Gly Gln
            130                 135                 140

<210> SEQ ID NO 38
<211> LENGTH: 140
<212> TYPE: PRT
<213> ORGANISM: Oryctolagus cuniculus

<400> SEQUENCE: 38

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Arg Leu Val Thr Pro
                20                  25                  30

Gly Thr Pro Leu Thr Leu Thr Cys Thr Val Ser Gly Ile Asp Leu Ser
            35                  40                  45

Ala Tyr Ala Met Ser Trp Val Arg Gln Ala Pro Gly Lys Gly Leu Glu
 50                  55                  60

Trp Ile Gly Leu Ile Arg Ser Ser Gly Ala Thr Tyr Tyr Ala Ser Trp
 65                  70                  75                  80

```
Ala Lys Gly Arg Phe Thr Ile Ser Lys Thr Ser Thr Val Asp Leu
            85                  90                  95

Lys Met Thr Ser Pro Thr Thr Glu Asp Thr Ala Thr Tyr Phe Cys Ala
                100                 105                 110

Arg Val Leu Trp Pro Gly Glu Ile Ala Tyr Ala Tyr His Asn Ile Trp
            115                 120                 125

Gly Pro Gly Thr Leu Val Thr Val Ser Ser Gly Gln
        130                 135                 140

<210> SEQ ID NO 39
<211> LENGTH: 140
<212> TYPE: PRT
<213> ORGANISM: Oryctolagus cuniculus

<400> SEQUENCE: 39

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Gly Ser Thr Tyr Tyr Ala Thr Trp
65                  70                  75                  80

Val Lys Gly Arg Phe Thr Ile Ser Lys Thr Ser Thr Val Asp Leu
            85                  90                  95

Lys Met Thr Ser Leu Thr Ala Ala Asp Thr Ala Thr Tyr Phe Cys Ala
                100                 105                 110

Arg Gly Asp Asp Asp Val Ser Asp Tyr Phe Tyr Tyr Phe Pro Ile Trp
            115                 120                 125

Gly Pro Gly Thr Leu Val Thr Val Ser Ser Gly Gln
        130                 135                 140

<210> SEQ ID NO 40
<211> LENGTH: 140
<212> TYPE: PRT
<213> ORGANISM: Oryctolagus cuniculus

<400> SEQUENCE: 40

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Gly Ser Thr Tyr Tyr Ala Thr Trp
65                  70                  75                  80

Val Lys Gly Arg Phe Thr Ile Ser Lys Thr Ser Thr Val Asp Leu
            85                  90                  95

Lys Met Thr Ser Leu Thr Ala Ala Asp Thr Ala Thr Tyr Phe Cys Ala
                100                 105                 110

Arg Gly Asp Asp Asp Val Ser Asp Tyr Phe Tyr Tyr Phe Pro Ile Trp
            115                 120                 125
```

```
Gly Pro Gly Thr Leu Val Thr Val Ser Ser Gly Gln
    130                 135                 140
```

<210> SEQ ID NO 41
<211> LENGTH: 140
<212> TYPE: PRT
<213> ORGANISM: Oryctolagus cuniculus

<400> SEQUENCE: 41

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Gly Ser Thr Tyr Tyr Ala Thr Trp
65                  70                  75                  80

Val Lys Gly Arg Phe Thr Ile Ser Lys Thr Ser Thr Val Asp Leu
                85                  90                  95

Lys Met Thr Ser Leu Thr Ala Ala Asp Thr Ala Thr Tyr Phe Cys Ala
            100                 105                 110

Arg Gly Asp Asp Val Ser Asp Tyr Phe Tyr Tyr Phe Pro Ile Trp
        115                 120                 125

Gly Pro Gly Thr Leu Val Thr Val Ser Ser Gly Gln
    130                 135                 140
```

<210> SEQ ID NO 42
<211> LENGTH: 140
<212> TYPE: PRT
<213> ORGANISM: Oryctolagus cuniculus

<400> SEQUENCE: 42

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Ser Trp Val Arg Gln Ala Pro Gly Lys Gly Leu Glu
    50                  55                  60

Trp Ile Gly Ile Ile Arg Pro Gly Gly Asn Thr Tyr Ser Ala Ser Trp
65                  70                  75                  80

Ala Lys Gly Arg Phe Thr Ile Ser Lys Thr Ser Thr Thr Val Asp Leu
                85                  90                  95

Lys Phe Thr Ser Pro Thr Pro Glu Asp Thr Ala Thr Tyr Phe Cys Ala
            100                 105                 110

Arg Val Leu Trp Ala Gly Asp Val Ala Tyr Ala Tyr His Asn Ile Trp
        115                 120                 125

Gly Pro Gly Thr Leu Val Thr Val Ser Ser Gly Gln
    130                 135                 140
```

<210> SEQ ID NO 43
<211> LENGTH: 132
<212> TYPE: PRT
<213> ORGANISM: Oryctolagus cuniculus

```
<400> SEQUENCE: 43

Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
                20                  25                  30

Val Ser Ala Ala Val Gly Gly Thr Val Thr Ile Asn Cys Gln Ala Ser
            35                  40                  45

Glu Glu Ile Gly Gly Asn Leu Ala Trp Tyr Gln Lys Pro Gly Gln
    50                  55                  60

Pro Pro Lys Leu Leu Ile Tyr Ser Ala Ser Thr Leu Thr Ser Gly Val
65                  70                  75                  80

Pro Ser Arg Phe Lys Gly Ser Gly Phe Gly Thr Glu Tyr Thr Leu Thr
                85                  90                  95

Ile Ser Asp Leu Glu Cys Asp Asp Ala Ala Thr Tyr Tyr Cys Gln Tyr
                100                 105                 110

Thr Tyr Tyr Gly Phe Thr Tyr Val Gly Pro Phe Gly Gly Gly Thr Glu
            115                 120                 125

Val Val Val Lys
    130

<210> SEQ ID NO 44
<211> LENGTH: 133
<212> TYPE: PRT
<213> ORGANISM: Oryctolagus cuniculus

<400> SEQUENCE: 44

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Pro Ser Ser
                20                  25                  30

Val Ser Ala Ala Val Gly Gly Thr Val Thr Ile Asn Cys Gln Ala Ser
            35                  40                  45

Glu Asn Ile Tyr Ser Asn Leu Ala Trp Tyr Gln Gln Lys Pro Gly Gln
    50                  55                  60

Pro Pro Lys Leu Leu Ile Tyr Gly Ala Ser Ala Leu Pro Ser Gly Val
65                  70                  75                  80

Pro Ser Arg Phe Ser Gly Ser Arg Ser Gly Thr Gln Phe Thr Leu Thr
                85                  90                  95

Ile Ser Asp Leu Glu Cys Ala Asp Ala Ala Thr Tyr Tyr Cys Gln Ser
                100                 105                 110

Tyr Phe Tyr Ser Ser Ser Asn Asp Asp Asn Pro Phe Gly Gly Gly Thr
            115                 120                 125

Glu Val Ala Val Lys
    130

<210> SEQ ID NO 45
<211> LENGTH: 132
<212> TYPE: PRT
<213> ORGANISM: Oryctolagus cuniculus

<400> SEQUENCE: 45

Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
                20                  25                  30

Val Ser Ala Ala Val Gly Gly Thr Val Thr Ile Asn Cys Gln Ala Ser
```

```
                35                  40                  45
Glu Glu Ile Gly Gly Asn Leu Ala Trp Tyr Gln Gln Lys Pro Gly Gln
         50                  55                  60

Pro Pro Lys Leu Leu Ile Tyr Ser Ala Ser Thr Leu Ala Ser Gly Val
 65                  70                  75                  80

Pro Ser Arg Phe Lys Gly Ser Gly Ser Gly Thr Glu Tyr Ser Leu Ser
                 85                  90                  95

Ile Ser Asp Leu Glu Cys Ala Asp Ala Ala Thr Tyr Tyr Cys Gln Tyr
                100                 105                 110

Thr Tyr Tyr Gly Phe Ser Tyr Val Gly Pro Phe Gly Gly Gly Thr Glu
                115                 120                 125

Val Val Val Lys
        130

<210> SEQ ID NO 46
<211> LENGTH: 133
<212> TYPE: PRT
<213> ORGANISM: Oryctolagus cuniculus

<400> SEQUENCE: 46

Met Asp Thr Arg Ala Pro Thr Gln Leu Leu Gly Leu Leu Leu Leu Trp
 1               5                  10                  15

Leu Pro Gly Ala Arg Cys Ala Val Val Leu Thr Gln Thr Ala Ser Pro
                 20                  25                  30

Val Ser Gly Ala Val Gly Gly Thr Val Thr Ile Asn Cys Gln Ala Ser
                 35                  40                  45

Gln Asn Ile Tyr Ser Asn Leu Ala Trp Tyr Gln His Lys Pro Gly Gln
         50                  55                  60

Pro Pro Lys Leu Leu Ile Tyr Lys Ala Ser Thr Leu Ala Ser Gly Val
 65                  70                  75                  80

Pro Ser Arg Phe Lys Gly Ser Gly Ser Gly Thr Glu Tyr Ile Leu Thr
                 85                  90                  95

Ile Ser Asp Leu Glu Cys Ala Asp Ala Ala Thr Tyr Tyr Cys Gln Thr
                100                 105                 110

Asn Tyr Tyr Ser Ile Asn Gly Gly Glu Val Thr Phe Gly Gly Gly Thr
                115                 120                 125

Glu Val Val Val Lys
        130

<210> SEQ ID NO 47
<211> LENGTH: 132
<212> TYPE: PRT
<213> ORGANISM: Oryctolagus cuniculus

<400> SEQUENCE: 47

Met Asp Thr Arg Ala Pro Thr Gln Leu Leu Gly Leu Leu Leu Leu Trp
 1               5                  10                  15

Leu Pro Gly Val Ile Cys Gly Pro Val Met Thr Gln Thr Pro Ala Ser
                 20                  25                  30

Val Ser Glu Pro Val Gly Gly Thr Val Thr Ile Lys Cys Gln Ala Ser
                 35                  40                  45

Glu Asp Ile Gly Ser Asn Leu Ala Trp Tyr Gln Gln Lys Pro Gly Gln
         50                  55                  60

Pro Pro Asn Leu Leu Val Tyr Ser Ala Ser Thr Leu Thr Ser Gly Val
 65                  70                  75                  80

Pro Ser Arg Phe Ser Gly Ser Gly Ser Gly Thr Glu Tyr Thr Leu Thr
```

```
                     85                  90                  95

Ile Ser Asp Leu Glu Cys Ala Asp Ala Ala Thr Tyr Tyr Cys Gln Asp
                    100                 105                 110

Thr Tyr Tyr Gly Asn Thr Tyr Leu Gly Ala Phe Gly Gly Gly Thr Glu
                115                 120                 125

Val Val Val Lys
        130

<210> SEQ ID NO 48
<211> LENGTH: 134
<212> TYPE: PRT
<213> ORGANISM: Oryctolagus cuniculus

<400> SEQUENCE: 48

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Thr Ser Ser
            20                  25                  30

Val Ser Ala Asp Val Gly Gly Thr Val Thr Ile Lys Cys Gln Ala Ser
        35                  40                  45

Glu Asn Ile Tyr Ser Leu Leu Ala Trp Tyr Gln Gln Lys Pro Gly Gln
    50                  55                  60

Pro Pro Lys Leu Leu Ile Tyr Ser Ala Ser Asp Leu Ala Ser Gly Val
65                  70                  75                  80

Pro Ser Arg Phe Ser Gly Ser Gly Phe Gly Thr Glu Phe Thr Leu Thr
                85                  90                  95

Ile Ser Asp Leu Glu Cys Ala Asp Ala Ala Thr Tyr His Cys Gln Ser
                    100                 105                 110

Tyr Tyr Tyr Ser Gly Ser Ser Ala Asp Thr Gly Ala Phe Gly Gly Gly
                115                 120                 125

Thr Glu Val Val Val Lys
        130

<210> SEQ ID NO 49
<211> LENGTH: 135
<212> TYPE: PRT
<213> ORGANISM: Oryctolagus cuniculus

<400> SEQUENCE: 49

Met Asp Thr Arg Ala Pro Thr Gln Leu Leu Gly Leu Leu Leu Leu Trp
1               5                   10                  15

Leu Pro Gly Ala Ile Phe Ala Gln Val Leu Thr Gln Ser Pro Ser Pro
            20                  25                  30

Val Ser Ala Ala Val Gly Gly Thr Val Thr Ile Asn Cys Gln Ala Ser
        35                  40                  45

Gln Ser Val Tyr Asn Gly Asp Trp Leu Gly Trp Tyr Gln Gln Lys Pro
    50                  55                  60

Gly Gln Pro Pro Lys Leu Leu Ile Tyr Asp Ala Ser Thr Leu Ala Ser
65                  70                  75                  80

Gly Val Ser Ser Leu Ile Asn Cys Asn Gly Ser Gly Thr Gln Trp Thr
                85                  90                  95

Leu Thr Ile Ser Gly Val Gln Cys Asp Ala Ala Thr Tyr Tyr Cys
                    100                 105                 110

Gln Gly Glu Phe Ser Cys Ser Ser Ala Asp Cys Val Ala Phe Gly Gly
                115                 120                 125

Gly Thr Glu Val Val Val Lys
```

<210> SEQ ID NO 50
<211> LENGTH: 133
<212> TYPE: PRT
<213> ORGANISM: Oryctolagus cuniculus

<400> SEQUENCE: 50

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Ala Ser Pro
            20                  25                  30

Val Ser Gly Ala Val Gly Gly Thr Val Thr Ile Lys Cys Gln Ala Ser
        35                  40                  45

Gln Asn Ile Tyr Asn Asn Leu Ala Trp Tyr Arg Gln Lys Pro Gly Gln
    50                  55                  60

Pro Pro Lys Leu Leu Ile Tyr Ala Ala Ser Lys Leu Ala Ser Gly Val
65                  70                  75                  80

Pro Ser Arg Phe Ser Gly Ser Arg Ser Gly Thr Gln Phe Thr Leu Ser
                85                  90                  95

Ile Ser Asp Leu Glu Cys Ala Asp Ala Ala Thr Tyr Tyr Cys Gln Ser
            100                 105                 110

Tyr Tyr Phe Asp Ser Ser Ser Thr Asp Ala Ala Phe Gly Gly Gly Thr
        115                 120                 125

Glu Val Val Val Lys
    130

<210> SEQ ID NO 51
<211> LENGTH: 133
<212> TYPE: PRT
<213> ORGANISM: Oryctolagus cuniculus

<400> SEQUENCE: 51

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Ala Ser Pro
            20                  25                  30

Val Ser Gly Ala Val Gly Gly Thr Val Thr Ile Lys Cys Gln Ala Ser
        35                  40                  45

Gln Asn Ile Tyr Asn Asn Leu Ala Trp Tyr Arg Gln Lys Pro Gly Gln
    50                  55                  60

Pro Pro Lys Leu Leu Ile Tyr Ala Ala Ser Lys Leu Ala Ser Gly Val
65                  70                  75                  80

Pro Ser Arg Phe Ser Gly Ser Arg Ser Gly Thr Gln Phe Thr Leu Ser
                85                  90                  95

Ile Ser Asp Leu Glu Cys Ala Asp Ala Ala Thr Tyr Tyr Cys Gln Ser
            100                 105                 110

Tyr Tyr Phe Asp Ser Ser Ser Thr Asp Ala Ala Phe Gly Gly Gly Thr
        115                 120                 125

Glu Val Val Val Lys
    130

<210> SEQ ID NO 52
<211> LENGTH: 132
<212> TYPE: PRT
<213> ORGANISM: Oryctolagus cuniculus

<400> SEQUENCE: 52

```
Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ala Ser
                20                  25                  30

Val Ser Ala Ala Val Gly Gly Thr Val Thr Ile Ser Cys Gln Ala Ser
            35                  40                  45

Gln Ser Ile His Ser Trp Val Ser Trp Tyr Gln Gln Lys Pro Gly Gln
    50                  55                  60

Pro Pro Lys Leu Leu Ile Tyr Tyr Ala Ala Thr Leu Ala Ser Gly Val
65                  70                  75                  80

Pro Ser Arg Phe Lys Gly Ser Gly Ser Gly Lys Gln Phe Thr Leu Thr
                85                  90                  95

Ile Ser Asp Leu Glu Cys Asp Asp Ala Ala Thr Tyr Tyr Cys Gln Gln
            100                 105                 110

Asp Phe Gly Gly Ser Asp Val Asp Asn Thr Phe Gly Gly Gly Thr Glu
            115                 120                 125

Val Val Val Ala
            130

<210> SEQ ID NO 53
<211> LENGTH: 132
<212> TYPE: PRT
<213> ORGANISM: Oryctolagus cuniculus

<400> SEQUENCE: 53

Met Asp Thr Arg Ala Pro Thr Gln Leu Leu Gly Leu Leu Leu Leu Trp
1               5                   10                  15

Leu Pro Gly Ala Arg Cys Asp Pro Val Leu Thr Gln Thr Pro Ala Ser
                20                  25                  30

Val Ser Ala Val Val Gly Gly Thr Val Thr Ile Asn Cys Gln Thr Ser
            35                  40                  45

Glu Asp Ile Ala Ser Asn Leu Ala Trp Tyr Gln Gln Lys Ser Gly Gln
    50                  55                  60

Arg Pro Lys Leu Leu Ile Tyr Glu Ala Ser Lys Leu Ala Ser Gly Val
65                  70                  75                  80

Pro Ser Arg Phe Lys Gly Ser Gly Ser Gly Thr Glu Tyr Thr Leu Thr
                85                  90                  95

Ile Ser Asp Leu Glu Cys Ala Asp Ala Ala Thr Tyr Tyr Cys Gln Tyr
            100                 105                 110

Thr Tyr Tyr Gly Ser Ser Tyr Leu Gly Ala Phe Gly Gly Gly Thr Glu
            115                 120                 125

Val Val Val Lys
            130

<210> SEQ ID NO 54
<211> LENGTH: 132
<212> TYPE: PRT
<213> ORGANISM: Oryctolagus cuniculus

<400> SEQUENCE: 54

Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
                20                  25                  30

Val Ser Ala Ala Val Gly Gly Thr Val Thr Ile Asn Cys Gln Ala Ser
            35                  40                  45
```

```
Glu Ile Gly Gly Asn Leu Ala Trp Tyr Gln Gln Lys Pro Gly Gln
    50                  55                  60

Pro Pro Gln Leu Leu Ile Tyr Ser Ala Ser Thr Leu Thr Ser Gly Val
65                  70                  75                  80

Pro Ser Arg Phe Lys Gly Ser Gly Phe Gly Thr Glu Tyr Thr Leu Thr
                85                  90                  95

Ile Ser Asp Leu Glu Cys Ala Asp Ala Ala Thr Tyr Tyr Cys Gln Tyr
                100                 105                 110

Thr Tyr Tyr Gly Phe Thr Tyr Val Gly Pro Phe Gly Gly Gly Thr Glu
            115                 120                 125

Val Val Val Lys
    130

<210> SEQ ID NO 55
<211> LENGTH: 133
<212> TYPE: PRT
<213> ORGANISM: Oryctolagus cuniculus

<400> SEQUENCE: 55

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Ala Ser Pro
                20                  25                  30

Val Ser Gly Ala Val Gly Gly Thr Val Thr Ile Lys Cys Gln Ala Ser
            35                  40                  45

Gln His Ile Tyr Ser Asn Leu Ala Trp Tyr Gln Gln Lys Pro Gly Gln
    50                  55                  60

Arg Pro Lys Leu Leu Ile Tyr Ala Ala Ser Lys Leu Ala Ser Gly Val
65                  70                  75                  80

Pro Ser Arg Phe Ser Gly Ser Arg Ser Gly Thr Glu Phe Thr Leu Thr
                85                  90                  95

Ile Ser Asp Leu Glu Cys Ala Asp Ala Ala Thr Tyr Tyr Cys Gln Ser
                100                 105                 110

Tyr Tyr Tyr Ser Ser Asp Ser Thr Asp Asn Thr Phe Gly Gly Gly Thr
            115                 120                 125

Glu Val Val Val Lys
    130

<210> SEQ ID NO 56
<211> LENGTH: 132
<212> TYPE: PRT
<213> ORGANISM: Oryctolagus cuniculus

<400> SEQUENCE: 56

Met Asp Thr Arg Ala Pro Thr Gln Leu Leu Gly Leu Leu Leu Leu Trp
1               5                   10                  15

Leu Pro Gly Val Ile Cys Gly Pro Val Met Thr Gln Thr Pro Ala Ser
                20                  25                  30

Val Ser Glu Pro Val Gly Gly Thr Val Thr Met Lys Cys Gln Ala Ser
            35                  40                  45

Glu Asp Ile Gly Ser Asn Leu Ala Trp Tyr Gln Gln Lys Pro Gly Gln
    50                  55                  60

Pro Pro Asn Leu Leu Val Phe Ser Ala Ser Thr Leu Ala Ser Gly Val
65                  70                  75                  80

Pro Ser Arg Phe Ala Gly Ser Gly Ser Gly Thr Glu Tyr Thr Leu Thr
                85                  90                  95
```

Ile Ser Asp Leu Glu Cys Ala Asp Ala Ala Thr Tyr Tyr Cys Gln Asp
                100                 105                 110

Ser Tyr Tyr Gly Asn Ser Tyr Leu Gly Ala Phe Gly Gly Gly Thr Glu
            115                 120                 125

Val Val Val Lys
        130

<210> SEQ ID NO 57
<211> LENGTH: 132
<212> TYPE: PRT
<213> ORGANISM: Oryctolagus cuniculus

<400> SEQUENCE: 57

Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

Glu Glu Ile Gly Gly Asn Leu Ala Trp Tyr Gln Gln Lys Pro Gly Gln
    50                  55                  60

Pro Pro Lys Leu Leu Ile Tyr Ser Ala Ser Thr Leu Thr Ser Gly Val
65                  70                  75                  80

Pro Ser Arg Phe Lys Gly Ser Gly Ser Gly Thr Glu Tyr Thr Leu Thr
                85                  90                  95

Ile Ser Asp Leu Glu Cys Ala Asp Ala Ala Thr Tyr Tyr Cys Gln Tyr
                100                 105                 110

Thr Tyr Tyr Gly Phe Ser Tyr Val Gly Pro Phe Gly Gly Gly Thr Glu
            115                 120                 125

Val Val Val Lys
        130

<210> SEQ ID NO 58
<211> LENGTH: 131
<212> TYPE: PRT
<213> ORGANISM: Oryctolagus cuniculus

<400> SEQUENCE: 58

Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

Glu Glu Ile Gly Gly Asn Leu Ala Trp Tyr Leu Gln Lys Pro Gly Gln
    50                  55                  60

Pro Pro Gln Leu Leu Ile Tyr Ser Ala Ser Thr Leu Thr Ser Gly Val
65                  70                  75                  80

Pro Ser Arg Phe Lys Gly Ser Gly Phe Gly Thr Glu Tyr Thr Leu Thr
                85                  90                  95

Ile Ser Asp Leu Glu Cys Ala Asp Ala Ala Thr Tyr Tyr Cys Gln Tyr
                100                 105                 110

Thr Tyr Tyr Gly Phe Ser Tyr Val Gly Pro Phe Gly Gly Gly Thr Glu
            115                 120                 125

Val Val Val
        130

<210> SEQ ID NO 59
<211> LENGTH: 132
<212> TYPE: PRT
<213> ORGANISM: Oryctolagus cuniculus

<400> SEQUENCE: 59

```
Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

Glu Glu Ile Gly Asp Asn Leu Ala Trp Tyr Gln Gln Lys Pro Gly Gln
    50                  55                  60

Pro Pro Lys Leu Leu Ile Tyr Ser Ala Ser Thr Leu Thr Ser Gly Val
65                  70                  75                  80

Pro Ser Arg Phe Lys Gly Ser Gly Phe Gly Thr Glu Tyr Thr Leu Thr
                85                  90                  95

Ile Ser Asp Leu Glu Cys Ala Asp Ala Ala Thr Tyr Tyr Cys Gln Tyr
            100                 105                 110

Thr Tyr Tyr Gly Phe Ser Tyr Val Gly Pro Phe Gly Gly Gly Thr Glu
        115                 120                 125

Val Val Val Lys
130
```

<210> SEQ ID NO 60
<211> LENGTH: 132
<212> TYPE: PRT
<213> ORGANISM: Oryctolagus cuniculus

<400> SEQUENCE: 60

```
Met Asp Thr Arg Ala Pro Thr Gln Leu Leu Gly Leu Leu Leu Leu Trp
1               5                   10                  15

Leu Pro Gly Ala Arg Cys Asp Pro Val Leu Thr Gln Thr Pro Ala Ser
            20                  25                  30

Val Ser Glu Pro Val Gly Gly Thr Val Thr Ile Lys Cys Gln Ala Ser
        35                  40                  45

Glu Asp Leu Gly Ser Asn Leu Ala Trp Tyr Gln Gln Lys Pro Gly Gln
    50                  55                  60

Pro Pro Lys Leu Leu Ile Tyr Ser Ala Ser Thr Leu Thr Ser Gly Val
65                  70                  75                  80

Pro Ser Arg Phe Lys Gly Ser Gly Ser Gly Thr Glu Tyr Thr Leu Thr
                85                  90                  95

Ile Ser Gly Val Gln Cys Asp Asp Ala Ala Thr Tyr Tyr Cys Gln Asp
            100                 105                 110

Thr Tyr Tyr Gly Asn Thr Tyr Leu Gly Ala Phe Gly Gly Gly Thr Glu
        115                 120                 125

Val Val Val Arg
130
```

<210> SEQ ID NO 61
<211> LENGTH: 132
<212> TYPE: PRT
<213> ORGANISM: Oryctolagus cuniculus

<400> SEQUENCE: 61

-continued

Met Asp Thr Arg Ala Pro Thr Gln Leu Leu Gly Leu Leu Leu Trp
1               5                   10                  15

Leu Pro Gly Ala Arg Cys Asp Leu Val Met Thr Gln Thr Pro Ser Pro
            20                  25                  30

Val Ser Ala Pro Val Gly Gly Thr Val Thr Ile Asn Cys Gln Ala Ser
        35                  40                  45

Glu Glu Ile Gly Gly Asn Leu Ala Trp Tyr Gln Gln Lys Pro Gly Gln
    50                  55                  60

Pro Pro Lys Leu Leu Ile Tyr Ser Ala Ser Thr Leu Thr Ser Gly Val
65                  70                  75                  80

Pro Ser Arg Phe Lys Gly Ser Gly Phe Gly Thr Glu Cys Ala Asp Ala
                85                  90                  95

Ala Thr Tyr Tyr Cys Gln Tyr Thr Tyr Tyr Gly Phe Ser Tyr Val Gly
            100                 105                 110

Pro Phe Gly Gly Gly Thr Glu Val Val Val Lys Glu Tyr Thr Leu Thr
        115                 120                 125

Ile Ser Asp Leu
        130

<210> SEQ ID NO 62
<211> LENGTH: 132
<212> TYPE: PRT
<213> ORGANISM: Oryctolagus cuniculus

<400> SEQUENCE: 62

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Ser Glu Pro Val Gly Gly Thr Val Thr Ile Asn Cys Gln Ala Ser
        35                  40                  45

Glu Glu Ile Gly Ser Asn Leu Ala Trp Tyr Gln Gln Lys Pro Gly Gln
    50                  55                  60

Pro Pro Lys Leu Leu Ile Tyr Ser Ala Ser Thr Leu Thr Ser Gly Val
65                  70                  75                  80

Pro Ser Arg Phe Lys Gly Ser Gly Ser Gly Thr Glu Tyr Thr Leu Thr
                85                  90                  95

Ile Ser Asp Leu Glu Cys Ala Asp Ala Ala Thr Tyr Tyr Cys Gln Tyr
            100                 105                 110

Thr Tyr Tyr Gly Phe Asn Tyr Val Gly Pro Phe Gly Gly Gly Thr Glu
        115                 120                 125

Val Val Val Lys
        130

<210> SEQ ID NO 63
<211> LENGTH: 132
<212> TYPE: PRT
<213> ORGANISM: Oryctolagus cuniculus

<400> SEQUENCE: 63

Met Asp Thr Arg Ala Pro Thr Gln Leu Leu Gly Leu Leu Leu Leu Trp
1               5                   10                  15

Leu Pro Gly Ala Arg Cys Asp Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

```
                        -continued

Glu Glu Ile Gly Gly Asn Leu Ala Trp Tyr Gln Gln Lys Pro Gly Gln
 50                  55                  60

Pro Pro Lys Leu Leu Ile Tyr Ser Ala Ser Thr Leu Thr Ser Gly Val
 65                  70                  75                  80

Pro Ser Arg Phe Lys Gly Ser Gly Ser Gly Thr Glu Tyr Thr Leu Thr
                 85                  90                  95

Ile Asn Asp Leu Glu Cys Ala Asp Ala Ala Thr Tyr Tyr Cys Gln Tyr
                100                 105                 110

Pro Tyr Tyr Gly Phe Ser Tyr Val Gly Pro Phe Gly Gly Gly Thr Glu
                115                 120                 125

Val Val Val Lys
        130

<210> SEQ ID NO 64
<211> LENGTH: 132
<212> TYPE: PRT
<213> ORGANISM: Oryctolagus cuniculus

<400> SEQUENCE: 64

Met Asp Thr Arg Ala Pro Thr Gln Leu Leu Gly Leu Leu Leu Leu Trp
 1               5                  10                  15

Leu Pro Gly Ala Arg Cys Asp Val Val Met Thr Gln Thr Pro Ala Ser
                 20                  25                  30

Val Ser Glu Pro Val Gly Gly Thr Val Thr Ile Asn Cys Gln Ala Ser
             35                  40                  45

Glu Glu Ile Gly Gly Asn Leu Ala Trp Tyr Gln Gln Lys Pro Gly Gln
 50                  55                  60

Pro Pro Lys Leu Leu Ile Tyr Ser Ala Ser Ser Leu Thr Ser Gly Val
 65                  70                  75                  80

Pro Ser Arg Phe Lys Gly Ser Glu Ser Gly Thr Glu Tyr Thr Leu Thr
                 85                  90                  95

Ile Ser Asp Leu Glu Cys Ala Asp Ala Ala Thr Tyr Tyr Cys Gln Tyr
                100                 105                 110

Ser Tyr Tyr Gly Phe Asn Tyr Val Gly Pro Phe Gly Gly Gly Thr Glu
                115                 120                 125

Val Val Val Lys
        130

<210> SEQ ID NO 65
<211> LENGTH: 133
<212> TYPE: PRT
<213> ORGANISM: Oryctolagus cuniculus

<400> SEQUENCE: 65

Met Asp Thr Arg Ala Pro Thr Gln Leu Leu Gly Leu Leu Leu Leu Trp
 1               5                  10                  15

Leu Pro Gly Ala Arg Cys Ala Val Val Leu Thr Gln Thr Ala Ser Pro
                 20                  25                  30

Val Ser Gly Ala Val Gly Gly Thr Val Thr Ile Lys Cys Gln Ala Ser
             35                  40                  45

Gln Asn Ile Tyr Asn Asn Leu Ala Trp Tyr Arg Gln Lys Pro Gly Gln
 50                  55                  60

Pro Pro Lys Leu Leu Ile Tyr Ala Ala Ser Lys Leu Ala Ser Gly Val
 65                  70                  75                  80

Pro Ser Arg Phe Ser Gly Ser Arg Ser Gly Thr Gln Phe Thr Leu Ser
                 85                  90                  95
```

```
Ile Ser Asp Leu Glu Cys Ala Asp Ala Ala Thr Tyr Tyr Cys Gln Ser
            100                 105                 110

Tyr Tyr Phe Asp Ser Ser Ser Thr Asp Ala Ala Phe Gly Gly Gly Thr
            115                 120                 125

Glu Val Val Val Lys
    130

<210> SEQ ID NO 66
<211> LENGTH: 133
<212> TYPE: PRT
<213> ORGANISM: Oryctolagus cuniculus

<400> SEQUENCE: 66

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Ala Ser Pro
            20                  25                  30

Val Ser Gly Ala Val Gly Gly Thr Val Thr Ile Lys Cys Gln Ala Ser
            35                  40                  45

Gln Asn Ile Tyr Asn Asn Leu Ala Trp Tyr Arg Gln Lys Pro Gly Gln
    50                  55                  60

Pro Pro Lys Leu Leu Ile Tyr Ala Ala Ser Lys Leu Ala Ser Gly Val
65                  70                  75                  80

Pro Ser Arg Phe Ser Gly Ser Arg Ser Gly Thr Gln Phe Thr Leu Ser
                85                  90                  95

Ile Ser Asp Leu Glu Cys Ala Asp Ala Ala Thr Tyr Tyr Cys Gln Ser
            100                 105                 110

Tyr Tyr Phe Asp Ser Ser Ser Thr Asp Ala Ala Phe Gly Gly Gly Thr
            115                 120                 125

Glu Val Val Val Lys
    130

<210> SEQ ID NO 67
<211> LENGTH: 134
<212> TYPE: PRT
<213> ORGANISM: Oryctolagus cuniculus

<400> SEQUENCE: 67

Met Asp Thr Arg Ala Pro Thr Gln Leu Leu Gly Leu Leu Leu Leu Trp
1               5                   10                  15

Leu Pro Gly Ala Arg Cys Asp Val Val Met Glu Thr Thr Gln Thr Pro
            20                  25                  30

Ala Ser Val Ser Glu Pro Val Gly Gly Thr Val Thr Ile Asn Cys Gln
            35                  40                  45

Ala Ser Glu Glu Ile Ala Ser Asn Leu Ala Trp Tyr Gln Gln Lys Pro
    50                  55                  60

Gly Gln Pro Pro Lys Leu Leu Ile Tyr Ser Ala Ser Thr Leu Thr Ser
65                  70                  75                  80

Gly Val Pro Ser Arg Phe Lys Gly Ser Gly Ser Gly Thr Glu Tyr Thr
                85                  90                  95

Leu Thr Ile Ser Asp Leu Glu Cys Ala Asp Ala Ala Thr Tyr Tyr Cys
            100                 105                 110

Gln Tyr Thr Tyr Tyr Gly Phe Asn Tyr Val Gly Pro Phe Gly Gly Gly
            115                 120                 125

Thr Glu Val Val Val Lys
    130
```

```
<210> SEQ ID NO 68
<211> LENGTH: 133
<212> TYPE: PRT
<213> ORGANISM: Oryctolagus cuniculus

<400> SEQUENCE: 68

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Ala Ser Pro
            20                  25                  30

Val Ser Gly Ala Val Gly Gly Thr Val Thr Ile Lys Cys Gln Ala Ser
        35                  40                  45

Gln Asn Ile Tyr Asn Asn Leu Ala Trp Tyr Arg Gln Lys Pro Gly Gln
    50                  55                  60

Pro Pro Lys Leu Leu Ile Tyr Ala Ala Ser Lys Leu Ala Ser Gly Val
65                  70                  75                  80

Pro Ser Arg Phe Ser Gly Ser Arg Ser Gly Thr Gln Phe Thr Leu Ser
                85                  90                  95

Ile Ser Asp Leu Glu Cys Ala Asp Ala Ala Thr Tyr Tyr Cys Gln Ser
            100                 105                 110

Tyr Tyr Phe Asp Ser Ser Ser Thr Asp Ala Ala Phe Gly Gly Gly Thr
        115                 120                 125

Glu Val Val Val Lys
    130

<210> SEQ ID NO 69
<211> LENGTH: 5
<212> TYPE: PRT
<213> ORGANISM: Oryctolagus cuniculus

<400> SEQUENCE: 69

Asn Tyr Ala Met Ser
1               5

<210> SEQ ID NO 70
<211> LENGTH: 5
<212> TYPE: PRT
<213> ORGANISM: Oryctolagus cuniculus

<400> SEQUENCE: 70

Ser Tyr Ala Met Gly
1               5

<210> SEQ ID NO 71
<211> LENGTH: 5
<212> TYPE: PRT
<213> ORGANISM: Oryctolagus cuniculus

<400> SEQUENCE: 71

Ser Tyr Ala Met Ser
1               5

<210> SEQ ID NO 72
<211> LENGTH: 6
<212> TYPE: PRT
<213> ORGANISM: Oryctolagus cuniculus

<400> SEQUENCE: 72

Ser Glu Phe Tyr Ile Cys
1               5
```

<210> SEQ ID NO 73
<211> LENGTH: 5
<212> TYPE: PRT
<213> ORGANISM: Oryctolagus cuniculus

<400> SEQUENCE: 73

Asp Tyr Ala Met Ser
1               5

<210> SEQ ID NO 74
<211> LENGTH: 6
<212> TYPE: PRT
<213> ORGANISM: Oryctolagus cuniculus

<400> SEQUENCE: 74

Ala Arg His Phe Met Tyr
1               5

<210> SEQ ID NO 75
<211> LENGTH: 5
<212> TYPE: PRT
<213> ORGANISM: Oryctolagus cuniculus

<400> SEQUENCE: 75

Ser Asn Ala Met Ala
1               5

<210> SEQ ID NO 76
<211> LENGTH: 5
<212> TYPE: PRT
<213> ORGANISM: Oryctolagus cuniculus

<400> SEQUENCE: 76

Ser Asn Ala Met Ser
1               5

<210> SEQ ID NO 77
<211> LENGTH: 5
<212> TYPE: PRT
<213> ORGANISM: Oryctolagus cuniculus

<400> SEQUENCE: 77

Ser Asn Ala Met Ser
1               5

<210> SEQ ID NO 78
<211> LENGTH: 5
<212> TYPE: PRT
<213> ORGANISM: Oryctolagus cuniculus

<400> SEQUENCE: 78

Lys Asn Ala Ile Ser
1               5

<210> SEQ ID NO 79
<211> LENGTH: 5
<212> TYPE: PRT
<213> ORGANISM: Oryctolagus cuniculus

<400> SEQUENCE: 79

Asp Phe Ala Met Ser
1               5

<210> SEQ ID NO 80

```
<211> LENGTH: 5
<212> TYPE: PRT
<213> ORGANISM: Oryctolagus cuniculus

<400> SEQUENCE: 80

Asn Tyr Ala Met Ser
1               5

<210> SEQ ID NO 81
<211> LENGTH: 5
<212> TYPE: PRT
<213> ORGANISM: Oryctolagus cuniculus

<400> SEQUENCE: 81

Asn Tyr Ala Met Ser
1               5

<210> SEQ ID NO 82
<211> LENGTH: 5
<212> TYPE: PRT
<213> ORGANISM: Oryctolagus cuniculus

<400> SEQUENCE: 82

Ser Tyr Ala Met Gly
1               5

<210> SEQ ID NO 83
<211> LENGTH: 5
<212> TYPE: PRT
<213> ORGANISM: Oryctolagus cuniculus

<400> SEQUENCE: 83

Asp Tyr Ala Met Ser
1               5

<210> SEQ ID NO 84
<211> LENGTH: 5
<212> TYPE: PRT
<213> ORGANISM: Oryctolagus cuniculus

<400> SEQUENCE: 84

Ser Tyr Ala Met Ser
1               5

<210> SEQ ID NO 85
<211> LENGTH: 5
<212> TYPE: PRT
<213> ORGANISM: Oryctolagus cuniculus

<400> SEQUENCE: 85

Asn Tyr Ala Met Ser
1               5

<210> SEQ ID NO 86
<211> LENGTH: 5
<212> TYPE: PRT
<213> ORGANISM: Oryctolagus cuniculus

<400> SEQUENCE: 86

Asn Tyr Ala Met Ser
1               5

<210> SEQ ID NO 87
<211> LENGTH: 5
<212> TYPE: PRT
```

-continued

<213> ORGANISM: Oryctolagus cuniculus

<400> SEQUENCE: 87

Ser Tyr Ala Met Ser
1               5

<210> SEQ ID NO 88
<211> LENGTH: 5
<212> TYPE: PRT
<213> ORGANISM: Oryctolagus cuniculus

<400> SEQUENCE: 88

Asn Tyr Ala Met Ser
1               5

<210> SEQ ID NO 89
<211> LENGTH: 5
<212> TYPE: PRT
<213> ORGANISM: Oryctolagus cuniculus

<400> SEQUENCE: 89

Ser Tyr Ala Met Ser
1               5

<210> SEQ ID NO 90
<211> LENGTH: 5
<212> TYPE: PRT
<213> ORGANISM: Oryctolagus cuniculus

<400> SEQUENCE: 90

Thr Tyr Ala Met Ser
1               5

<210> SEQ ID NO 91
<211> LENGTH: 5
<212> TYPE: PRT
<213> ORGANISM: Oryctolagus cuniculus

<400> SEQUENCE: 91

Ala Tyr Ala Met Ser
1               5

<210> SEQ ID NO 92
<211> LENGTH: 5
<212> TYPE: PRT
<213> ORGANISM: Oryctolagus cuniculus

<400> SEQUENCE: 92

Ser Asn Ala Met Ser
1               5

<210> SEQ ID NO 93
<211> LENGTH: 5
<212> TYPE: PRT
<213> ORGANISM: Oryctolagus cuniculus

<400> SEQUENCE: 93

Ser Asn Ala Met Ser
1               5

<210> SEQ ID NO 94
<211> LENGTH: 5
<212> TYPE: PRT
<213> ORGANISM: Oryctolagus cuniculus

```
<400> SEQUENCE: 94

Ser Asn Ala Met Ser
1               5

<210> SEQ ID NO 95
<211> LENGTH: 5
<212> TYPE: PRT
<213> ORGANISM: Oryctolagus cuniculus

<400> SEQUENCE: 95

Ser Tyr Ala Met Ser
1               5

<210> SEQ ID NO 96
<211> LENGTH: 16
<212> TYPE: PRT
<213> ORGANISM: Oryctolagus cuniculus

<400> SEQUENCE: 96

Leu Ile Arg Ser Ser Gly Ala Thr Tyr Tyr Ala Ser Trp Ala Lys Gly
1               5                   10                  15

<210> SEQ ID NO 97
<211> LENGTH: 16
<212> TYPE: PRT
<213> ORGANISM: Oryctolagus cuniculus

<400> SEQUENCE: 97

Ile Ile Thr Ala Ser Gly Gly Ile Tyr Tyr Ala Ser Trp Ala Lys Gly
1               5                   10                  15

<210> SEQ ID NO 98
<211> LENGTH: 16
<212> TYPE: PRT
<213> ORGANISM: Oryctolagus cuniculus

<400> SEQUENCE: 98

Leu Ile Arg Arg Ser Gly Ala Thr Tyr Tyr Ala Ser Trp Ala Lys Gly
1               5                   10                  15

<210> SEQ ID NO 99
<211> LENGTH: 17
<212> TYPE: PRT
<213> ORGANISM: Oryctolagus cuniculus

<400> SEQUENCE: 99

Cys Ile Ala Thr Val Ser Ser Arg Arg Leu Tyr Ala Ser Trp Val Asn
1               5                   10                  15

Gly

<210> SEQ ID NO 100
<211> LENGTH: 16
<212> TYPE: PRT
<213> ORGANISM: Oryctolagus cuniculus

<400> SEQUENCE: 100

Met Val Arg Asp Thr Gly Val Thr Phe Tyr Ala Gly Trp Ala Lys Gly
1               5                   10                  15

<210> SEQ ID NO 101
<211> LENGTH: 17
<212> TYPE: PRT
<213> ORGANISM: Oryctolagus cuniculus
```

-continued

```
<400> SEQUENCE: 101

Cys Ile Asp Ile Gly Ser Gly Ser Thr Tyr Tyr Thr Ser Trp Ala Lys
1               5                   10                  15

Asp

<210> SEQ ID NO 102
<211> LENGTH: 16
<212> TYPE: PRT
<213> ORGANISM: Oryctolagus cuniculus

<400> SEQUENCE: 102

Ile Ile Asp Gly Asp Val Ser Pro Tyr Tyr Ala Ser Trp Ala Lys Gly
1               5                   10                  15

<210> SEQ ID NO 103
<211> LENGTH: 16
<212> TYPE: PRT
<213> ORGANISM: Oryctolagus cuniculus

<400> SEQUENCE: 103

Thr Ile Ser Ser Ser Gly Ser Thr Tyr Tyr Ala Thr Trp Val Lys Gly
1               5                   10                  15

<210> SEQ ID NO 104
<211> LENGTH: 16
<212> TYPE: PRT
<213> ORGANISM: Oryctolagus cuniculus

<400> SEQUENCE: 104

Thr Ile Ser Ser Ser Gly Ser Thr Tyr Tyr Ala Thr Trp Val Lys Gly
1               5                   10                  15

<210> SEQ ID NO 105
<211> LENGTH: 16
<212> TYPE: PRT
<213> ORGANISM: Oryctolagus cuniculus

<400> SEQUENCE: 105

Ile Ile Tyr Gly Asp Gly Asn Arg Asp Tyr Ala Asn Trp Ala Lys Gly
1               5                   10                  15

<210> SEQ ID NO 106
<211> LENGTH: 16
<212> TYPE: PRT
<213> ORGANISM: Oryctolagus cuniculus

<400> SEQUENCE: 106

Met Ile Ala Ser Ser Gly Asn Thr Phe Tyr Ala Ser Trp Ala Lys Gly
1               5                   10                  15

<210> SEQ ID NO 107
<211> LENGTH: 16
<212> TYPE: PRT
<213> ORGANISM: Oryctolagus cuniculus

<400> SEQUENCE: 107

Leu Ile Arg Ser Ser Gly Ala Thr Tyr Tyr Ala Ser Trp Ala Lys Gly
1               5                   10                  15

<210> SEQ ID NO 108
<211> LENGTH: 16
<212> TYPE: PRT
<213> ORGANISM: Oryctolagus cuniculus
```

```
<400> SEQUENCE: 108

Ile Ile Gly Ser Ser Gly Ser Ile Phe Tyr Ala Ser Trp Ala Lys Gly
1               5                   10                  15

<210> SEQ ID NO 109
<211> LENGTH: 16
<212> TYPE: PRT
<213> ORGANISM: Oryctolagus cuniculus

<400> SEQUENCE: 109

Phe Ile Ser Ser Ser Gly Ser Thr Tyr Tyr Ala Ser Trp Ala Lys Gly
1               5                   10                  15

<210> SEQ ID NO 110
<211> LENGTH: 16
<212> TYPE: PRT
<213> ORGANISM: Oryctolagus cuniculus

<400> SEQUENCE: 110

Ile Ile Ser Asn Ser Gly Ile Thr Phe Tyr Ala Gly Trp Ala Lys Gly
1               5                   10                  15

<210> SEQ ID NO 111
<211> LENGTH: 16
<212> TYPE: PRT
<213> ORGANISM: Oryctolagus cuniculus

<400> SEQUENCE: 111

Leu Ile Arg Ser Ser Gly Ala Thr Tyr Tyr Ala Ser Trp Ala Lys Gly
1               5                   10                  15

<210> SEQ ID NO 112
<211> LENGTH: 16
<212> TYPE: PRT
<213> ORGANISM: Oryctolagus cuniculus

<400> SEQUENCE: 112

Leu Ile Arg Ser Ser Gly Ala Ala Tyr Asp Ala Pro Trp Ala Lys Gly
1               5                   10                  15

<210> SEQ ID NO 113
<211> LENGTH: 16
<212> TYPE: PRT
<213> ORGANISM: Oryctolagus cuniculus

<400> SEQUENCE: 113

Leu Ile Arg Ser Gly Gly Ala Thr Tyr Tyr Ala Ser Trp Ala Lys Gly
1               5                   10                  15

<210> SEQ ID NO 114
<211> LENGTH: 16
<212> TYPE: PRT
<213> ORGANISM: Oryctolagus cuniculus

<400> SEQUENCE: 114

Ile Ile Arg Gly Ser Gly Ser Ile Tyr Tyr Ala Asn Trp Ala Lys Gly
1               5                   10                  15

<210> SEQ ID NO 115
<211> LENGTH: 16
<212> TYPE: PRT
<213> ORGANISM: Oryctolagus cuniculus

<400> SEQUENCE: 115
```

```
Leu Ile Arg Ser Ser Gly Ala Thr Tyr Tyr Ala Ser Trp Ala Lys Gly
 1               5                  10                  15

<210> SEQ ID NO 116
<211> LENGTH: 16
<212> TYPE: PRT
<213> ORGANISM: Oryctolagus cuniculus

<400> SEQUENCE: 116

Ile Ile Ser Ser Ser Gly Asn Thr Tyr Phe Ala Ser Trp Ala Lys Gly
 1               5                  10                  15

<210> SEQ ID NO 117
<211> LENGTH: 16
<212> TYPE: PRT
<213> ORGANISM: Oryctolagus cuniculus

<400> SEQUENCE: 117

Leu Ile Arg Ser Ser Gly Ala Thr Tyr Tyr Ala Ser Trp Ala Lys Gly
 1               5                  10                  15

<210> SEQ ID NO 118
<211> LENGTH: 16
<212> TYPE: PRT
<213> ORGANISM: Oryctolagus cuniculus

<400> SEQUENCE: 118

Leu Ile Arg Ser Ser Gly Ala Thr Tyr Tyr Ala Ser Trp Ala Lys Gly
 1               5                  10                  15

<210> SEQ ID NO 119
<211> LENGTH: 16
<212> TYPE: PRT
<213> ORGANISM: Oryctolagus cuniculus

<400> SEQUENCE: 119

Thr Ile Ser Ser Ser Gly Ser Thr Tyr Tyr Ala Thr Trp Val Lys Gly
 1               5                  10                  15

<210> SEQ ID NO 120
<211> LENGTH: 16
<212> TYPE: PRT
<213> ORGANISM: Oryctolagus cuniculus

<400> SEQUENCE: 120

Thr Ile Ser Ser Ser Gly Ser Thr Tyr Tyr Ala Thr Trp Val Lys Gly
 1               5                  10                  15

<210> SEQ ID NO 121
<211> LENGTH: 16
<212> TYPE: PRT
<213> ORGANISM: Oryctolagus cuniculus

<400> SEQUENCE: 121

Thr Ile Ser Ser Ser Gly Ser Thr Tyr Tyr Ala Thr Trp Val Lys Gly
 1               5                  10                  15

<210> SEQ ID NO 122
<211> LENGTH: 16
<212> TYPE: PRT
<213> ORGANISM: Oryctolagus cuniculus

<400> SEQUENCE: 122

Ile Ile Arg Pro Gly Gly Asn Thr Tyr Ser Ala Ser Trp Ala Lys Gly
 1               5                  10                  15
```

<210> SEQ ID NO 123
<211> LENGTH: 14
<212> TYPE: PRT
<213> ORGANISM: Oryctolagus cuniculus

<400> SEQUENCE: 123

Val Leu Trp Pro Gly Asp Ile Ala Tyr Ala Tyr His Asn Ile
1               5                   10

<210> SEQ ID NO 124
<211> LENGTH: 11
<212> TYPE: PRT
<213> ORGANISM: Oryctolagus cuniculus

<400> SEQUENCE: 124

Thr Glu Asn Ser Tyr Phe Leu Tyr Phe Thr Ile
1               5                   10

<210> SEQ ID NO 125
<211> LENGTH: 14
<212> TYPE: PRT
<213> ORGANISM: Oryctolagus cuniculus

<400> SEQUENCE: 125

Val Leu Trp Pro Gly Asp Ile Ala Tyr Ala Tyr His Asn Ile
1               5                   10

<210> SEQ ID NO 126
<211> LENGTH: 12
<212> TYPE: PRT
<213> ORGANISM: Oryctolagus cuniculus

<400> SEQUENCE: 126

Asp Asp Ser Ala Arg Asn Trp Phe Tyr Phe Tyr Leu
1               5                   10

<210> SEQ ID NO 127
<211> LENGTH: 14
<212> TYPE: PRT
<213> ORGANISM: Oryctolagus cuniculus

<400> SEQUENCE: 127

Val Leu Trp Ala Gly Tyr Val Ala Tyr Ala Tyr His Asn Ile
1               5                   10

<210> SEQ ID NO 128
<211> LENGTH: 10
<212> TYPE: PRT
<213> ORGANISM: Oryctolagus cuniculus

<400> SEQUENCE: 128

Ser Ser Gly Tyr Pro Tyr Tyr Phe Thr Leu
1               5                   10

<210> SEQ ID NO 129
<211> LENGTH: 4
<212> TYPE: PRT
<213> ORGANISM: Oryctolagus cuniculus

<400> SEQUENCE: 129

Pro Phe Asn Ile
1

<210> SEQ ID NO 130
<211> LENGTH: 14
<212> TYPE: PRT
<213> ORGANISM: Oryctolagus cuniculus

<400> SEQUENCE: 130

Gly Asp Asp Asp Val Ser Asp Tyr Phe Tyr Tyr Phe Pro Ile
1               5                   10

<210> SEQ ID NO 131
<211> LENGTH: 14
<212> TYPE: PRT
<213> ORGANISM: Oryctolagus cuniculus

<400> SEQUENCE: 131

Gly Asp Asp Asp Val Ser Asp Tyr Phe Tyr Tyr Phe Pro Ile
1               5                   10

<210> SEQ ID NO 132
<211> LENGTH: 11
<212> TYPE: PRT
<213> ORGANISM: Oryctolagus cuniculus

<400> SEQUENCE: 132

Gly Thr Thr Ile Trp Ser Asp Tyr Leu Asp Ile
1               5                   10

<210> SEQ ID NO 133
<211> LENGTH: 14
<212> TYPE: PRT
<213> ORGANISM: Oryctolagus cuniculus

<400> SEQUENCE: 133

Val Leu Trp Pro Gly Tyr Ile Ala Tyr Ala Tyr His Asn Ile
1               5                   10

<210> SEQ ID NO 134
<211> LENGTH: 14
<212> TYPE: PRT
<213> ORGANISM: Oryctolagus cuniculus

<400> SEQUENCE: 134

Val Leu Trp Pro Gly Asp Ile Ala Tyr Ala Tyr His Asn Ile
1               5                   10

<210> SEQ ID NO 135
<211> LENGTH: 14
<212> TYPE: PRT
<213> ORGANISM: Oryctolagus cuniculus

<400> SEQUENCE: 135

Val Leu Trp Ala Gly Ser Val Ala Tyr Ala Tyr His Asn Ile
1               5                   10

<210> SEQ ID NO 136
<211> LENGTH: 14
<212> TYPE: PRT
<213> ORGANISM: Oryctolagus cuniculus

<400> SEQUENCE: 136

Asn Tyr Asp Asp Tyr Gly Asp Phe Leu His Tyr Phe Asn Ile
1               5                   10

<210> SEQ ID NO 137
<211> LENGTH: 14

<212> TYPE: PRT
<213> ORGANISM: Oryctolagus cuniculus

<400> SEQUENCE: 137

Ala Leu Trp Ala Gly Tyr Ile Ala Tyr Val Tyr His Asn Ile
1               5                   10

<210> SEQ ID NO 138
<211> LENGTH: 14
<212> TYPE: PRT
<213> ORGANISM: Oryctolagus cuniculus

<400> SEQUENCE: 138

Val Leu Trp Pro Gly Asp Ile Ala Tyr Ala Tyr His Asn Ile
1               5                   10

<210> SEQ ID NO 139
<211> LENGTH: 14
<212> TYPE: PRT
<213> ORGANISM: Oryctolagus cuniculus

<400> SEQUENCE: 139

Val Leu Trp Pro Gly Asp Ile Ala Tyr Ala Tyr His Asn Ile
1               5                   10

<210> SEQ ID NO 140
<211> LENGTH: 14
<212> TYPE: PRT
<213> ORGANISM: Oryctolagus cuniculus

<400> SEQUENCE: 140

Val Leu Trp Pro Gly Asp Ile Ala Tyr Ala Tyr His Asn Ile
1               5                   10

<210> SEQ ID NO 141
<211> LENGTH: 14
<212> TYPE: PRT
<213> ORGANISM: Oryctolagus cuniculus

<400> SEQUENCE: 141

Val Leu Trp Pro Gly Ser Val Ala Tyr Ala Tyr His Asn Ile
1               5                   10

<210> SEQ ID NO 142
<211> LENGTH: 14
<212> TYPE: PRT
<213> ORGANISM: Oryctolagus cuniculus

<400> SEQUENCE: 142

Val Leu Trp Pro Gly Asp Ile Ala Tyr Ala Tyr His Asn Ile
1               5                   10

<210> SEQ ID NO 143
<211> LENGTH: 14
<212> TYPE: PRT
<213> ORGANISM: Oryctolagus cuniculus

<400> SEQUENCE: 143

Val Leu Trp Ala Gly Ser Val Ala Tyr Ala Tyr His Asn Ile
1               5                   10

<210> SEQ ID NO 144
<211> LENGTH: 14
<212> TYPE: PRT
<213> ORGANISM: Oryctolagus cuniculus -continued

<400> SEQUENCE: 144

Val Leu Trp Pro Gly Asp Ile Ala Tyr Ala Tyr His Asn Ile
1               5                   10

<210> SEQ ID NO 145
<211> LENGTH: 14
<212> TYPE: PRT
<213> ORGANISM: Oryctolagus cuniculus

<400> SEQUENCE: 145

Val Leu Trp Pro Gly Glu Ile Ala Tyr Ala Tyr His Asn Ile
1               5                   10

<210> SEQ ID NO 146
<211> LENGTH: 14
<212> TYPE: PRT
<213> ORGANISM: Oryctolagus cuniculus

<400> SEQUENCE: 146

Gly Asp Asp Asp Val Ser Asp Tyr Phe Tyr Tyr Phe Pro Ile
1               5                   10

<210> SEQ ID NO 147
<211> LENGTH: 14
<212> TYPE: PRT
<213> ORGANISM: Oryctolagus cuniculus

<400> SEQUENCE: 147

Gly Asp Asp Asp Val Ser Asp Tyr Phe Tyr Tyr Phe Pro Ile
1               5                   10

<210> SEQ ID NO 148
<211> LENGTH: 14
<212> TYPE: PRT
<213> ORGANISM: Oryctolagus cuniculus

<400> SEQUENCE: 148

Gly Asp Asp Asp Val Ser Asp Tyr Phe Tyr Tyr Phe Pro Ile
1               5                   10

<210> SEQ ID NO 149
<211> LENGTH: 14
<212> TYPE: PRT
<213> ORGANISM: Oryctolagus cuniculus

<400> SEQUENCE: 149

Val Leu Trp Ala Gly Asp Val Ala Tyr Ala Tyr His Asn Ile
1               5                   10

<210> SEQ ID NO 150
<211> LENGTH: 11
<212> TYPE: PRT
<213> ORGANISM: Oryctolagus cuniculus

<400> SEQUENCE: 150

Gln Ala Ser Glu Glu Ile Gly Gly Asn Leu Ala
1               5                   10

<210> SEQ ID NO 151
<211> LENGTH: 11
<212> TYPE: PRT
<213> ORGANISM: Oryctolagus cuniculus

<400> SEQUENCE: 151

Gln Ala Ser Glu Asn Ile Tyr Ser Asn Leu Ala
1               5                   10

<210> SEQ ID NO 152
<211> LENGTH: 11
<212> TYPE: PRT
<213> ORGANISM: Oryctolagus cuniculus

<400> SEQUENCE: 152

Gln Ala Ser Glu Glu Ile Gly Gly Asn Leu Ala
1               5                   10

<210> SEQ ID NO 153
<211> LENGTH: 11
<212> TYPE: PRT
<213> ORGANISM: Oryctolagus cuniculus

<400> SEQUENCE: 153

Gln Ala Ser Gln Asn Ile Tyr Ser Asn Leu Ala
1               5                   10

<210> SEQ ID NO 154
<211> LENGTH: 11
<212> TYPE: PRT
<213> ORGANISM: Oryctolagus cuniculus

<400> SEQUENCE: 154

Gln Ala Ser Glu Asp Ile Gly Ser Asn Leu Ala
1               5                   10

<210> SEQ ID NO 155
<211> LENGTH: 11
<212> TYPE: PRT
<213> ORGANISM: Oryctolagus cuniculus

<400> SEQUENCE: 155

Gln Ala Ser Glu Asn Ile Tyr Ser Leu Leu Ala
1               5                   10

<210> SEQ ID NO 156
<211> LENGTH: 13
<212> TYPE: PRT
<213> ORGANISM: Oryctolagus cuniculus

<400> SEQUENCE: 156

Gln Ala Ser Gln Ser Val Tyr Asn Gly Asp Trp Leu Gly
1               5                   10

<210> SEQ ID NO 157
<211> LENGTH: 11
<212> TYPE: PRT
<213> ORGANISM: Oryctolagus cuniculus

<400> SEQUENCE: 157

Gln Ala Ser Gln Asn Ile Tyr Asn Asn Leu Ala
1               5                   10

<210> SEQ ID NO 158
<211> LENGTH: 11
<212> TYPE: PRT
<213> ORGANISM: Oryctolagus cuniculus

<400> SEQUENCE: 158

Gln Ala Ser Gln Asn Ile Tyr Asn Asn Leu Ala

```
1               5                   10
```

<210> SEQ ID NO 159
<211> LENGTH: 11
<212> TYPE: PRT
<213> ORGANISM: Oryctolagus cuniculus

<400> SEQUENCE: 159

```
Gln Ala Ser Gln Ser Ile His Ser Trp Val Ser
1               5                   10
```

<210> SEQ ID NO 160
<211> LENGTH: 11
<212> TYPE: PRT
<213> ORGANISM: Oryctolagus cuniculus

<400> SEQUENCE: 160

```
Gln Thr Ser Glu Asp Ile Ala Ser Asn Leu Ala
1               5                   10
```

<210> SEQ ID NO 161
<211> LENGTH: 11
<212> TYPE: PRT
<213> ORGANISM: Oryctolagus cuniculus

<400> SEQUENCE: 161

```
Gln Ala Ser Glu Glu Ile Gly Gly Asn Leu Ala
1               5                   10
```

<210> SEQ ID NO 162
<211> LENGTH: 11
<212> TYPE: PRT
<213> ORGANISM: Oryctolagus cuniculus

<400> SEQUENCE: 162

```
Gln Ala Ser Glu Glu Leu Gly Ser Asn Leu Ala
1               5                   10
```

<210> SEQ ID NO 163
<211> LENGTH: 11
<212> TYPE: PRT
<213> ORGANISM: Oryctolagus cuniculus

<400> SEQUENCE: 163

```
Gln Ala Ser Gln His Ile Tyr Ser Asn Leu Ala
1               5                   10
```

<210> SEQ ID NO 164
<211> LENGTH: 11
<212> TYPE: PRT
<213> ORGANISM: Oryctolagus cuniculus

<400> SEQUENCE: 164

```
Gln Ala Ser Glu Asp Ile Gly Ser Asn Leu Ala
1               5                   10
```

<210> SEQ ID NO 165
<211> LENGTH: 11
<212> TYPE: PRT
<213> ORGANISM: Oryctolagus cuniculus

<400> SEQUENCE: 165

```
Gln Ala Ser Glu Glu Ile Gly Gly Asn Leu Ala
1               5                   10
```

<210> SEQ ID NO 166
<211> LENGTH: 11
<212> TYPE: PRT
<213> ORGANISM: Oryctolagus cuniculus

<400> SEQUENCE: 166

Gln Ala Ser Glu Glu Ile Gly Gly Asn Leu Ala
1               5                   10

<210> SEQ ID NO 167
<211> LENGTH: 11
<212> TYPE: PRT
<213> ORGANISM: Oryctolagus cuniculus

<400> SEQUENCE: 167

Gln Ala Ser Glu Glu Ile Gly Asp Asn Leu Ala
1               5                   10

<210> SEQ ID NO 168
<211> LENGTH: 11
<212> TYPE: PRT
<213> ORGANISM: Oryctolagus cuniculus

<400> SEQUENCE: 168

Gln Ala Ser Glu Asp Leu Gly Ser Asn Leu Ala
1               5                   10

<210> SEQ ID NO 169
<211> LENGTH: 11
<212> TYPE: PRT
<213> ORGANISM: Oryctolagus cuniculus

<400> SEQUENCE: 169

Gln Ala Ser Glu Glu Ile Gly Gly Asn Leu Ala
1               5                   10

<210> SEQ ID NO 170
<211> LENGTH: 11
<212> TYPE: PRT
<213> ORGANISM: Oryctolagus cuniculus

<400> SEQUENCE: 170

Gln Ala Ser Glu Glu Ile Gly Ser Asn Leu Ala
1               5                   10

<210> SEQ ID NO 171
<211> LENGTH: 11
<212> TYPE: PRT
<213> ORGANISM: Oryctolagus cuniculus

<400> SEQUENCE: 171

Gln Ala Ser Glu Glu Ile Gly Gly Asn Leu Ala
1               5                   10

<210> SEQ ID NO 172
<211> LENGTH: 11
<212> TYPE: PRT
<213> ORGANISM: Oryctolagus cuniculus

<400> SEQUENCE: 172

Gln Ala Ser Glu Glu Ile Gly Gly Asn Leu Ala
1               5                   10

<210> SEQ ID NO 173

```
<211> LENGTH: 11
<212> TYPE: PRT
<213> ORGANISM: Oryctolagus cuniculus

<400> SEQUENCE: 173

Gln Ala Ser Gln Asn Ile Tyr Asn Asn Leu Ala
1               5                   10

<210> SEQ ID NO 174
<211> LENGTH: 11
<212> TYPE: PRT
<213> ORGANISM: Oryctolagus cuniculus

<400> SEQUENCE: 174

Gln Ala Ser Gln Asn Ile Tyr Asn Asn Leu Ala
1               5                   10

<210> SEQ ID NO 175
<211> LENGTH: 11
<212> TYPE: PRT
<213> ORGANISM: Oryctolagus cuniculus

<400> SEQUENCE: 175

Gln Ala Ser Glu Glu Ile Ala Ser Asn Leu Ala
1               5                   10

<210> SEQ ID NO 176
<211> LENGTH: 11
<212> TYPE: PRT
<213> ORGANISM: Oryctolagus cuniculus

<400> SEQUENCE: 176

Gln Ala Ser Gln Asn Ile Tyr Asn Asn Leu Ala
1               5                   10

<210> SEQ ID NO 177
<211> LENGTH: 7
<212> TYPE: PRT
<213> ORGANISM: Oryctolagus cuniculus

<400> SEQUENCE: 177

Ser Ala Ser Thr Leu Thr Ser
1               5

<210> SEQ ID NO 178
<211> LENGTH: 7
<212> TYPE: PRT
<213> ORGANISM: Oryctolagus cuniculus

<400> SEQUENCE: 178

Gly Ala Ser Ala Leu Pro Ser
1               5

<210> SEQ ID NO 179
<211> LENGTH: 7
<212> TYPE: PRT
<213> ORGANISM: Oryctolagus cuniculus

<400> SEQUENCE: 179

Ser Ala Ser Thr Leu Ala Ser
1               5

<210> SEQ ID NO 180
<211> LENGTH: 7
<212> TYPE: PRT
```

```
<213> ORGANISM: Oryctolagus cuniculus

<400> SEQUENCE: 180

Lys Ala Ser Thr Leu Ala Ser
1               5

<210> SEQ ID NO 181
<211> LENGTH: 7
<212> TYPE: PRT
<213> ORGANISM: Oryctolagus cuniculus

<400> SEQUENCE: 181

Ser Ala Ser Thr Leu Thr Ser
1               5

<210> SEQ ID NO 182
<211> LENGTH: 7
<212> TYPE: PRT
<213> ORGANISM: Oryctolagus cuniculus

<400> SEQUENCE: 182

Ser Ala Ser Asp Leu Ala Ser
1               5

<210> SEQ ID NO 183
<211> LENGTH: 7
<212> TYPE: PRT
<213> ORGANISM: Oryctolagus cuniculus

<400> SEQUENCE: 183

Asp Ala Ser Thr Leu Ala Ser
1               5

<210> SEQ ID NO 184
<211> LENGTH: 7
<212> TYPE: PRT
<213> ORGANISM: Oryctolagus cuniculus

<400> SEQUENCE: 184

Ala Ala Ser Lys Leu Ala Ser
1               5

<210> SEQ ID NO 185
<211> LENGTH: 7
<212> TYPE: PRT
<213> ORGANISM: Oryctolagus cuniculus

<400> SEQUENCE: 185

Ala Ala Ser Lys Leu Ala Ser
1               5

<210> SEQ ID NO 186
<211> LENGTH: 7
<212> TYPE: PRT
<213> ORGANISM: Oryctolagus cuniculus

<400> SEQUENCE: 186

Tyr Ala Ala Thr Leu Ala Ser
1               5

<210> SEQ ID NO 187
<211> LENGTH: 7
<212> TYPE: PRT
<213> ORGANISM: Oryctolagus cuniculus
```

```
<400> SEQUENCE: 187

Glu Ala Ser Lys Leu Ala Ser
1               5

<210> SEQ ID NO 188
<211> LENGTH: 7
<212> TYPE: PRT
<213> ORGANISM: Oryctolagus cuniculus

<400> SEQUENCE: 188

Ser Ala Ser Thr Leu Thr Ser
1               5

<210> SEQ ID NO 189
<211> LENGTH: 7
<212> TYPE: PRT
<213> ORGANISM: Oryctolagus cuniculus

<400> SEQUENCE: 189

Ser Ala Ser Thr Leu Ala Ser
1               5

<210> SEQ ID NO 190
<211> LENGTH: 7
<212> TYPE: PRT
<213> ORGANISM: Oryctolagus cuniculus

<400> SEQUENCE: 190

Ala Ala Ser Lys Leu Ala Ser
1               5

<210> SEQ ID NO 191
<211> LENGTH: 7
<212> TYPE: PRT
<213> ORGANISM: Oryctolagus cuniculus

<400> SEQUENCE: 191

Ser Ala Ser Thr Leu Ala Ser
1               5

<210> SEQ ID NO 192
<211> LENGTH: 7
<212> TYPE: PRT
<213> ORGANISM: Oryctolagus cuniculus

<400> SEQUENCE: 192

Ser Ala Ser Thr Leu Thr Ser
1               5

<210> SEQ ID NO 193
<211> LENGTH: 7
<212> TYPE: PRT
<213> ORGANISM: Oryctolagus cuniculus

<400> SEQUENCE: 193

Ser Ala Ser Thr Leu Thr Ser
1               5

<210> SEQ ID NO 194
<211> LENGTH: 7
<212> TYPE: PRT
<213> ORGANISM: Oryctolagus cuniculus

<400> SEQUENCE: 194
```

Ser Ala Ser Thr Leu Thr Ser
1               5

<210> SEQ ID NO 195
<211> LENGTH: 7
<212> TYPE: PRT
<213> ORGANISM: Oryctolagus cuniculus

<400> SEQUENCE: 195

Ser Ala Ser Thr Leu Thr Ser
1               5

<210> SEQ ID NO 196
<211> LENGTH: 7
<212> TYPE: PRT
<213> ORGANISM: Oryctolagus cuniculus

<400> SEQUENCE: 196

Ser Ala Ser Thr Leu Thr Ser
1               5

<210> SEQ ID NO 197
<211> LENGTH: 7
<212> TYPE: PRT
<213> ORGANISM: Oryctolagus cuniculus

<400> SEQUENCE: 197

Ser Ala Ser Thr Leu Thr Ser
1               5

<210> SEQ ID NO 198
<211> LENGTH: 7
<212> TYPE: PRT
<213> ORGANISM: Oryctolagus cuniculus

<400> SEQUENCE: 198

Ser Ala Ser Thr Leu Thr Ser
1               5

<210> SEQ ID NO 199
<211> LENGTH: 7
<212> TYPE: PRT
<213> ORGANISM: Oryctolagus cuniculus

<400> SEQUENCE: 199

Ser Ala Ser Ser Leu Thr Ser
1               5

<210> SEQ ID NO 200
<211> LENGTH: 7
<212> TYPE: PRT
<213> ORGANISM: Oryctolagus cuniculus

<400> SEQUENCE: 200

Ala Ala Ser Lys Leu Ala Ser
1               5

<210> SEQ ID NO 201
<211> LENGTH: 7
<212> TYPE: PRT
<213> ORGANISM: Oryctolagus cuniculus

<400> SEQUENCE: 201

Ala Ala Ser Lys Leu Ala Ser
1               5

<210> SEQ ID NO 202
<211> LENGTH: 7
<212> TYPE: PRT
<213> ORGANISM: Oryctolagus cuniculus

<400> SEQUENCE: 202

Ser Ala Ser Thr Leu Thr Ser
1               5

<210> SEQ ID NO 203
<211> LENGTH: 7
<212> TYPE: PRT
<213> ORGANISM: Oryctolagus cuniculus

<400> SEQUENCE: 203

Ala Ala Ser Lys Leu Ala Ser
1               5

<210> SEQ ID NO 204
<211> LENGTH: 12
<212> TYPE: PRT
<213> ORGANISM: Oryctolagus cuniculus

<400> SEQUENCE: 204

Gln Tyr Thr Tyr Tyr Gly Phe Thr Tyr Val Gly Pro
1               5                   10

<210> SEQ ID NO 205
<211> LENGTH: 13
<212> TYPE: PRT
<213> ORGANISM: Oryctolagus cuniculus

<400> SEQUENCE: 205

Gln Ser Tyr Phe Tyr Ser Ser Ser Asn Asp Asp Asn Pro
1               5                   10

<210> SEQ ID NO 206
<211> LENGTH: 12
<212> TYPE: PRT
<213> ORGANISM: Oryctolagus cuniculus

<400> SEQUENCE: 206

Gln Tyr Thr Tyr Tyr Gly Phe Ser Tyr Val Gly Pro
1               5                   10

<210> SEQ ID NO 207
<211> LENGTH: 13
<212> TYPE: PRT
<213> ORGANISM: Oryctolagus cuniculus

<400> SEQUENCE: 207

Gln Thr Asn Tyr Tyr Ser Ile Asn Gly Gly Glu Val Thr
1               5                   10

<210> SEQ ID NO 208
<211> LENGTH: 12
<212> TYPE: PRT
<213> ORGANISM: Oryctolagus cuniculus

<400> SEQUENCE: 208

Gln Asp Thr Tyr Tyr Gly Asn Thr Tyr Leu Gly Ala
1               5                   10

```
<210> SEQ ID NO 209
<211> LENGTH: 14
<212> TYPE: PRT
<213> ORGANISM: Oryctolagus cuniculus

<400> SEQUENCE: 209

Gln Ser Tyr Tyr Tyr Ser Gly Ser Ser Ala Asp Thr Gly Ala
1               5                   10

<210> SEQ ID NO 210
<211> LENGTH: 13
<212> TYPE: PRT
<213> ORGANISM: Oryctolagus cuniculus

<400> SEQUENCE: 210

Gln Gly Glu Phe Ser Cys Ser Ser Ala Asp Cys Val Ala
1               5                   10

<210> SEQ ID NO 211
<211> LENGTH: 13
<212> TYPE: PRT
<213> ORGANISM: Oryctolagus cuniculus

<400> SEQUENCE: 211

Gln Ser Tyr Tyr Phe Asp Ser Ser Ser Thr Asp Ala Ala
1               5                   10

<210> SEQ ID NO 212
<211> LENGTH: 13
<212> TYPE: PRT
<213> ORGANISM: Oryctolagus cuniculus

<400> SEQUENCE: 212

Gln Ser Tyr Tyr Phe Asp Ser Ser Ser Thr Asp Ala Ala
1               5                   10

<210> SEQ ID NO 213
<211> LENGTH: 12
<212> TYPE: PRT
<213> ORGANISM: Oryctolagus cuniculus

<400> SEQUENCE: 213

Gln Gln Asp Phe Gly Gly Ser Asp Val Asp Asn Thr
1               5                   10

<210> SEQ ID NO 214
<211> LENGTH: 12
<212> TYPE: PRT
<213> ORGANISM: Oryctolagus cuniculus

<400> SEQUENCE: 214

Gln Tyr Thr Tyr Tyr Gly Ser Ser Tyr Leu Gly Ala
1               5                   10

<210> SEQ ID NO 215
<211> LENGTH: 12
<212> TYPE: PRT
<213> ORGANISM: Oryctolagus cuniculus

<400> SEQUENCE: 215

Gln Tyr Thr Tyr Tyr Gly Phe Thr Tyr Val Gly Pro
1               5                   10

<210> SEQ ID NO 216
<211> LENGTH: 12
```

```
<212> TYPE: PRT
<213> ORGANISM: Oryctolagus cuniculus

<400> SEQUENCE: 216

Gln Tyr Thr Tyr Phe Gly Ser Ser Tyr Leu Gly Ala
1               5                   10

<210> SEQ ID NO 217
<211> LENGTH: 13
<212> TYPE: PRT
<213> ORGANISM: Oryctolagus cuniculus

<400> SEQUENCE: 217

Gln Ser Tyr Tyr Tyr Ser Ser Asp Ser Thr Asp Asn Thr
1               5                   10

<210> SEQ ID NO 218
<211> LENGTH: 12
<212> TYPE: PRT
<213> ORGANISM: Oryctolagus cuniculus

<400> SEQUENCE: 218

Gln Asp Ser Tyr Tyr Gly Asn Ser Tyr Leu Gly Ala
1               5                   10

<210> SEQ ID NO 219
<211> LENGTH: 12
<212> TYPE: PRT
<213> ORGANISM: Oryctolagus cuniculus

<400> SEQUENCE: 219

Gln Tyr Thr Tyr Tyr Gly Phe Ser Tyr Val Gly Pro
1               5                   10

<210> SEQ ID NO 220
<211> LENGTH: 12
<212> TYPE: PRT
<213> ORGANISM: Oryctolagus cuniculus

<400> SEQUENCE: 220

Gln Tyr Thr Tyr Tyr Gly Phe Ser Tyr Val Gly Pro
1               5                   10

<210> SEQ ID NO 221
<211> LENGTH: 12
<212> TYPE: PRT
<213> ORGANISM: Oryctolagus cuniculus

<400> SEQUENCE: 221

Gln Tyr Thr Tyr Tyr Gly Phe Ser Tyr Val Gly Pro
1               5                   10

<210> SEQ ID NO 222
<211> LENGTH: 12
<212> TYPE: PRT
<213> ORGANISM: Oryctolagus cuniculus

<400> SEQUENCE: 222

Gln Asp Thr Tyr Tyr Gly Asn Thr Tyr Leu Gly Ala
1               5                   10

<210> SEQ ID NO 223
<211> LENGTH: 12
<212> TYPE: PRT
<213> ORGANISM: Oryctolagus cuniculus
```

<400> SEQUENCE: 223

Gln Tyr Thr Tyr Tyr Gly Phe Ser Tyr Val Gly Pro
1               5                   10

<210> SEQ ID NO 224
<211> LENGTH: 12
<212> TYPE: PRT
<213> ORGANISM: Oryctolagus cuniculus

<400> SEQUENCE: 224

Gln Tyr Thr Tyr Tyr Gly Phe Asn Tyr Val Gly Pro
1               5                   10

<210> SEQ ID NO 225
<211> LENGTH: 12
<212> TYPE: PRT
<213> ORGANISM: Oryctolagus cuniculus

<400> SEQUENCE: 225

Gln Tyr Pro Tyr Tyr Gly Phe Ser Tyr Val Gly Pro
1               5                   10

<210> SEQ ID NO 226
<211> LENGTH: 12
<212> TYPE: PRT
<213> ORGANISM: Oryctolagus cuniculus

<400> SEQUENCE: 226

Gln Tyr Ser Tyr Tyr Gly Phe Asn Tyr Val Gly Pro
1               5                   10

<210> SEQ ID NO 227
<211> LENGTH: 13
<212> TYPE: PRT
<213> ORGANISM: Oryctolagus cuniculus

<400> SEQUENCE: 227

Gln Ser Tyr Tyr Phe Asp Ser Ser Ser Thr Asp Ala Ala
1               5                   10

<210> SEQ ID NO 228
<211> LENGTH: 13
<212> TYPE: PRT
<213> ORGANISM: Oryctolagus cuniculus

<400> SEQUENCE: 228

Gln Ser Tyr Tyr Phe Asp Ser Ser Ser Thr Asp Ala Ala
1               5                   10

<210> SEQ ID NO 229
<211> LENGTH: 12
<212> TYPE: PRT
<213> ORGANISM: Oryctolagus cuniculus

<400> SEQUENCE: 229

Gln Tyr Thr Tyr Tyr Gly Phe Asn Tyr Val Gly Pro
1               5                   10

<210> SEQ ID NO 230
<211> LENGTH: 13
<212> TYPE: PRT
<213> ORGANISM: Oryctolagus cuniculus

<400> SEQUENCE: 230

```
Gln Ser Tyr Tyr Phe Asp Ser Ser Thr Asp Ala Ala
1               5                   10
```

```
<210> SEQ ID NO 231
<211> LENGTH: 14
<212> TYPE: PRT
<213> ORGANISM: Artificial Sequence
<220> FEATURE:
<223> OTHER INFORMATION: Peptide spacer sequence

<400> SEQUENCE: 231

Glu Gly Lys Ser Ser Gly Ser Gly Ser Glu Ser Lys Val Asp
1               5                   10
```

```
<210> SEQ ID NO 232
<211> LENGTH: 18
<212> TYPE: PRT
<213> ORGANISM: Artificial Sequence
<220> FEATURE:
<223> OTHER INFORMATION: Peptide spacer sequence

<400> SEQUENCE: 232

Lys Glu Ser Gly Ser Val Ser Ser Glu Gln Leu Ala Gln Phe Arg Ser
1               5                   10                  15

Leu Asp
```

```
<210> SEQ ID NO 233
<211> LENGTH: 5
<212> TYPE: PRT
<213> ORGANISM: Artificial Sequence
<220> FEATURE:
<223> OTHER INFORMATION: Peptide spacer sequence

<400> SEQUENCE: 233

Gly Gly Gly Gly Ser
1               5
```